(12) United States Patent
Simon et al.

(10) Patent No.: US 9,126,050 B2
(45) Date of Patent: Sep. 8, 2015

(54) NON-INVASIVE VAGUS NERVE STIMULATION DEVICES AND METHODS TO TREAT OR AVERT ATRIAL FIBRILLATION

(71) Applicants: Bruce J. Simon, Mountain Lakes, NJ (US); Joseph P. Errico, Warren, NJ (US); John T. Raffle, Austin, TX (US)

(72) Inventors: Bruce J. Simon, Mountain Lakes, NJ (US); Joseph P. Errico, Warren, NJ (US); John T. Raffle, Austin, TX (US)

(73) Assignee: Electrocore, LLC, Basking Ridge, NJ (US)

( * ) Notice: Subject to any disclaimer, the term of this patent is extended or adjusted under 35 U.S.C. 154(b) by 0 days.

(21) Appl. No.: 13/736,096

(22) Filed: Jan. 8, 2013

(65) Prior Publication Data

US 2013/0131746 A1 May 23, 2013

Related U.S. Application Data

(63) Continuation-in-part of application No. 13/603,781, filed on Sep. 5, 2012, now Pat. No. 8,983,628, which is a continuation-in-part of application No. 13/222,087, filed on Aug. 31, 2011, which is a continuation-in-part (Continued)

(51) Int. Cl.
*A61N 1/36* (2006.01)
*A61N 1/362* (2006.01)

(52) U.S. Cl.
CPC .............. *A61N 1/3625* (2013.01); *A61N 1/362* (2013.01); *A61N 1/36014* (2013.01); *A61N 1/36053* (2013.01); *A61N 1/36114* (2013.01); *A61N 1/36171* (2013.01); *A61N 1/36178* (2013.01)

(58) Field of Classification Search
CPC ............ A61N 1/3625; A61N 1/36114; A61N 1/36053
See application file for complete search history.

(56) References Cited

U.S. PATENT DOCUMENTS

| | | | |
|---|---|---|---|
| 3,590,810 A * | 7/1971 | Kopecky | 600/396 |
| 4,196,737 A | 4/1980 | Bevilacqua | |
| 5,458,141 A | 10/1995 | Neil | |
| 5,782,874 A * | 7/1998 | Loos | 607/2 |
| 5,983,131 A | 11/1999 | Weaver et al. | |
| 6,341,236 B1 | 1/2002 | Osorio et al. | |
| 6,463,327 B1 | 10/2002 | Lurie et al. | |
| 6,587,719 B1 | 7/2003 | Barrett et al. | |

(Continued)

FOREIGN PATENT DOCUMENTS

| | | |
|---|---|---|
| WO | WO 93/01862 | 2/1993 |
| WO | WO 2009/021080 | 2/2009 |
| WO | WO 2009/135693 | 11/2009 |

OTHER PUBLICATIONS

Greicius et al., Functional connectivity in the resting brain: A network analysis of the default mode hypothesis, PNAS, Jan. 2003, vol. 100, No. 1, pp. 253-258.

(Continued)

*Primary Examiner* — Michael Kahelin
(74) *Attorney, Agent, or Firm* — Dentons US LLP

(57) ABSTRACT

Energy is transmitted noninvasively to a patient using electrode-based stimulation devices or magnetic stimulation devices that are designed to non-invasively stimulate nerves selectively. The devices produce impulses that are used to treat atrial fibrillation, by stimulating a vagus nerve of a patient. The devices are also used to forecast the imminent onset of atrial fibrillation and then avert it by stimulating a vagus nerve.

6 Claims, 11 Drawing Sheets

Related U.S. Application Data of application No. 13/183,765, filed on Jul. 15, 2011, now Pat. No. 8,874,227, and a continuation-in-part of application No. 13/183,721, filed on Jul. 15, 2011, now Pat. No. 8,676,324, and a continuation-in-part of application No. 13/109,250, filed on May 17, 2011, now Pat. No. 8,676,330, and a continuation-in-part of application No. 13/075,746, filed on Mar. 30, 2011, now Pat. No. 8,874,205, and a continuation-in-part of application No. 13/005,005, filed on Jan. 12, 2011, now Pat. No. 8,868,177, which is a continuation-in-part of application No. 12/964,050, filed on Dec. 9, 2010, which is a continuation-in-part of application No. 12/859,568, filed on Aug. 19, 2010, now Pat. No. 9,037,247, said application No. 12/859,568 is a continuation-in-part of application No. 12/612,177, filed on Nov. 4, 2009, now Pat. No. 8,041,428, and a continuation-in-part of application No. 12/408,131, filed on Mar. 20, 2009, now Pat. No. 8,812,112.

(60) Provisional application No. 61/585,668, filed on Jan. 12, 2012, provisional application No. 61/488,208, filed on May 20, 2011, provisional application No. 61/487,439, filed on May 18, 2011, provisional application No. 61/471,405, filed on Apr. 4, 2011, provisional application No. 61/451,259, filed on Mar. 10, 2011, provisional application No. 61/415,469, filed on Nov. 19, 2010.

(56) References Cited

U.S. PATENT DOCUMENTS

| | | | |
|---|---|---|---|
| 6,610,713 | B2 | 8/2003 | Tracey |
| 7,797,041 | B2 | 9/2010 | Libbus et al. |
| 2002/0099417 | A1 | 7/2002 | Naritoku et al. |
| 2002/0183237 | A1 | 12/2002 | Puskas |
| 2004/0138721 | A1 | 7/2004 | Osorio et al. |
| 2004/0243182 | A1 | 12/2004 | Cohen et al. |
| 2004/0249416 | A1 | 12/2004 | Yun et al. |
| 2005/0021092 | A1 | 1/2005 | Yun et al. |
| 2005/0065574 | A1 | 3/2005 | Rezai |
| 2005/0137644 | A1 | 6/2005 | Bojeva et al. |
| 2006/0074284 | A1 | 4/2006 | Juola et al. |
| 2006/0100668 | A1 | 5/2006 | Ben-David et al. |
| 2006/0100671 | A1 | 5/2006 | Ridder |
| 2006/0173510 | A1 | 8/2006 | Besio et al. |
| 2006/0178703 | A1 | 8/2006 | Huston et al. |
| 2007/0027496 | A1 | 2/2007 | Parnis et al. |
| 2007/0123952 | A1 | 5/2007 | Strother et al. |
| 2007/0142886 | A1* | 6/2007 | Fischell et al. ............... 607/103 |
| 2007/0150006 | A1 | 6/2007 | Libbus et al. |
| 2007/0276449 | A1 | 11/2007 | Gunter et al. |
| 2008/0021512 | A1 | 1/2008 | Knudson et al. |
| 2008/0027513 | A1 | 1/2008 | Carbunaru |
| 2008/0045776 | A1 | 2/2008 | Fischell et al. |
| 2008/0051852 | A1 | 2/2008 | Dietrich et al. |
| 2008/0132964 | A1* | 6/2008 | Cohen et al. ............... 607/5 |
| 2008/0177190 | A1 | 7/2008 | Libbus et al. |
| 2008/0208266 | A1 | 8/2008 | Lesser et al. |
| 2008/0306325 | A1 | 12/2008 | Burnett et al. |
| 2009/0157149 | A1 | 6/2009 | Wahlgren et al. |
| 2009/0234419 | A1 | 9/2009 | Maschino et al. |
| 2009/0287035 | A1 | 11/2009 | Dietrich et al. |
| 2010/0286553 | A1 | 11/2010 | Feler et al. |
| 2011/0046432 | A1 | 2/2011 | Simon et al. |
| 2011/0152967 | A1 | 6/2011 | Simon et al. |
| 2011/0213295 | A1 | 9/2011 | Henley et al. |
| 2011/0224749 | A1 | 9/2011 | Ben-David et al. |
| 2011/0230701 | A1 | 9/2011 | Simon et al. |
| 2012/0029601 | A1 | 2/2012 | Simon et al. |
| 2012/0184801 | A1 | 7/2012 | Simon et al. |
| 2012/0283697 | A1 | 11/2012 | Kim et al. |
| 2012/0303080 | A1 | 11/2012 | Ben-David et al. |
| 2013/0131753 | A1 | 5/2013 | Simon et al. |
| 2013/0238050 | A1 | 9/2013 | Simon et al. |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

International Search Report and Written Opinion dated Mar. 25, 2014 in related PCT Application No. PCT/US2014/010589 filed Jan. 8, 2014 (7 pages).

\* cited by examiner

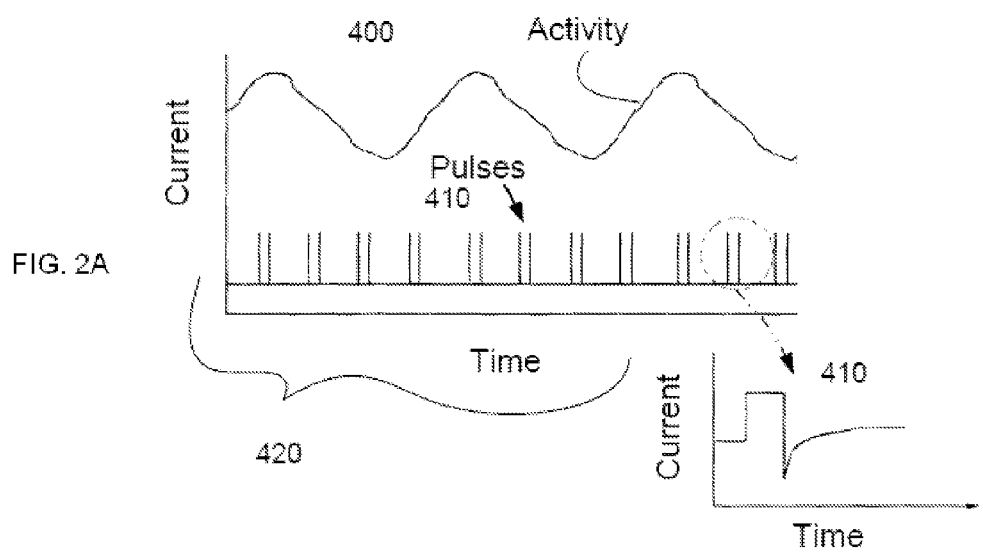
FIG. 2A
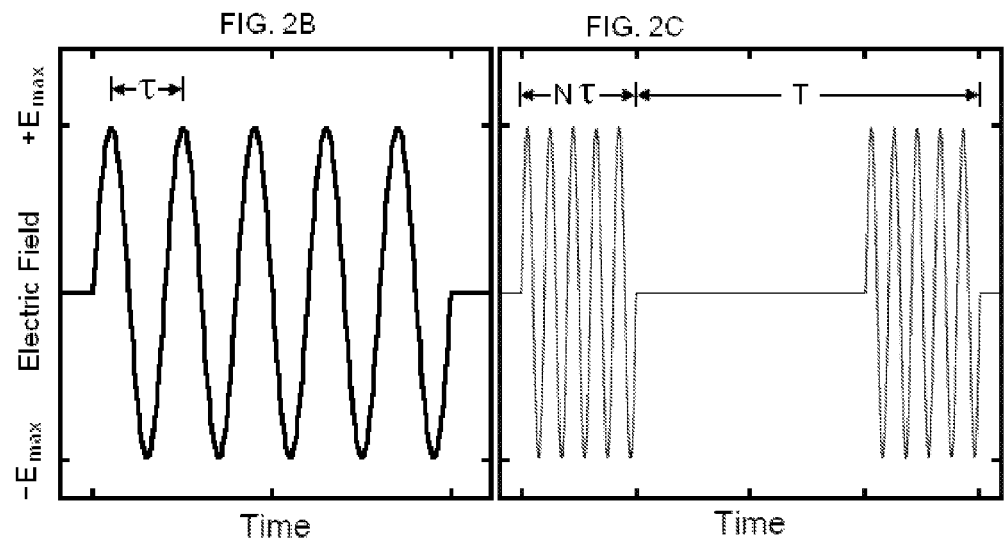
FIG. 2B
FIG. 2C

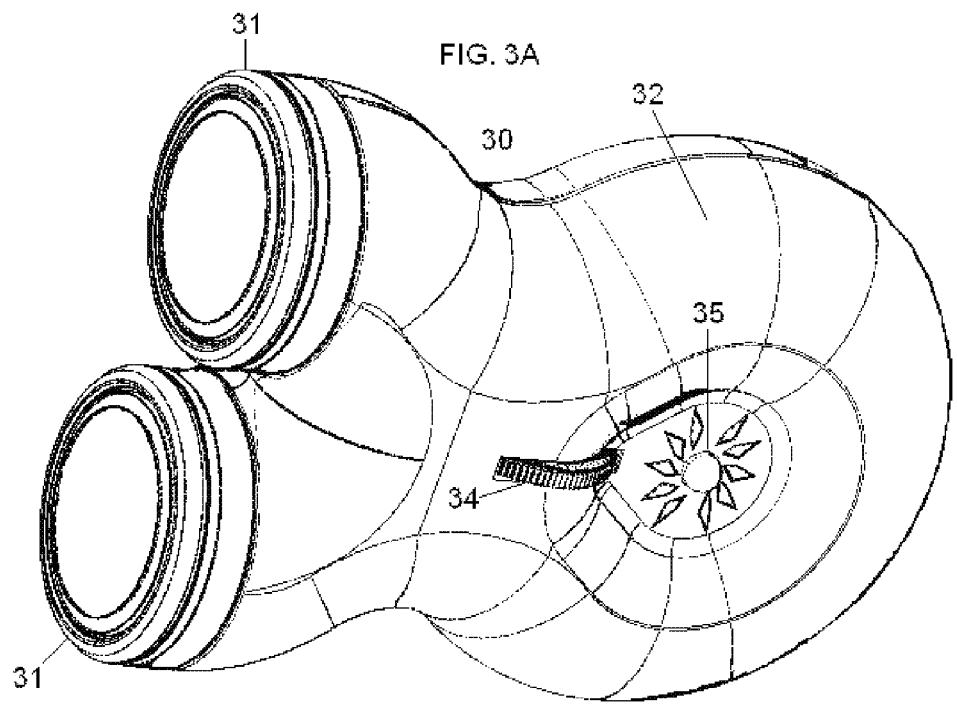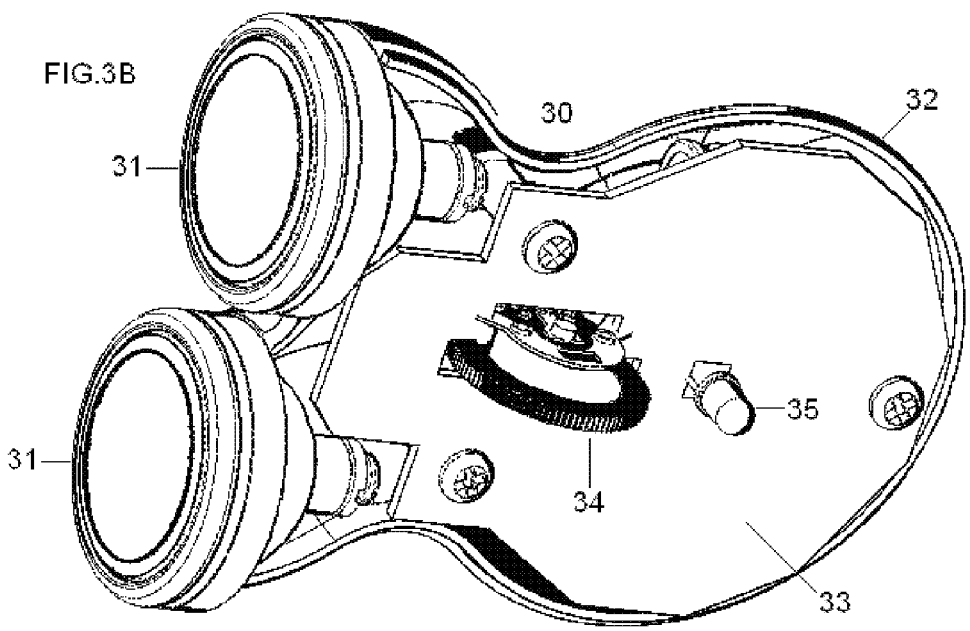

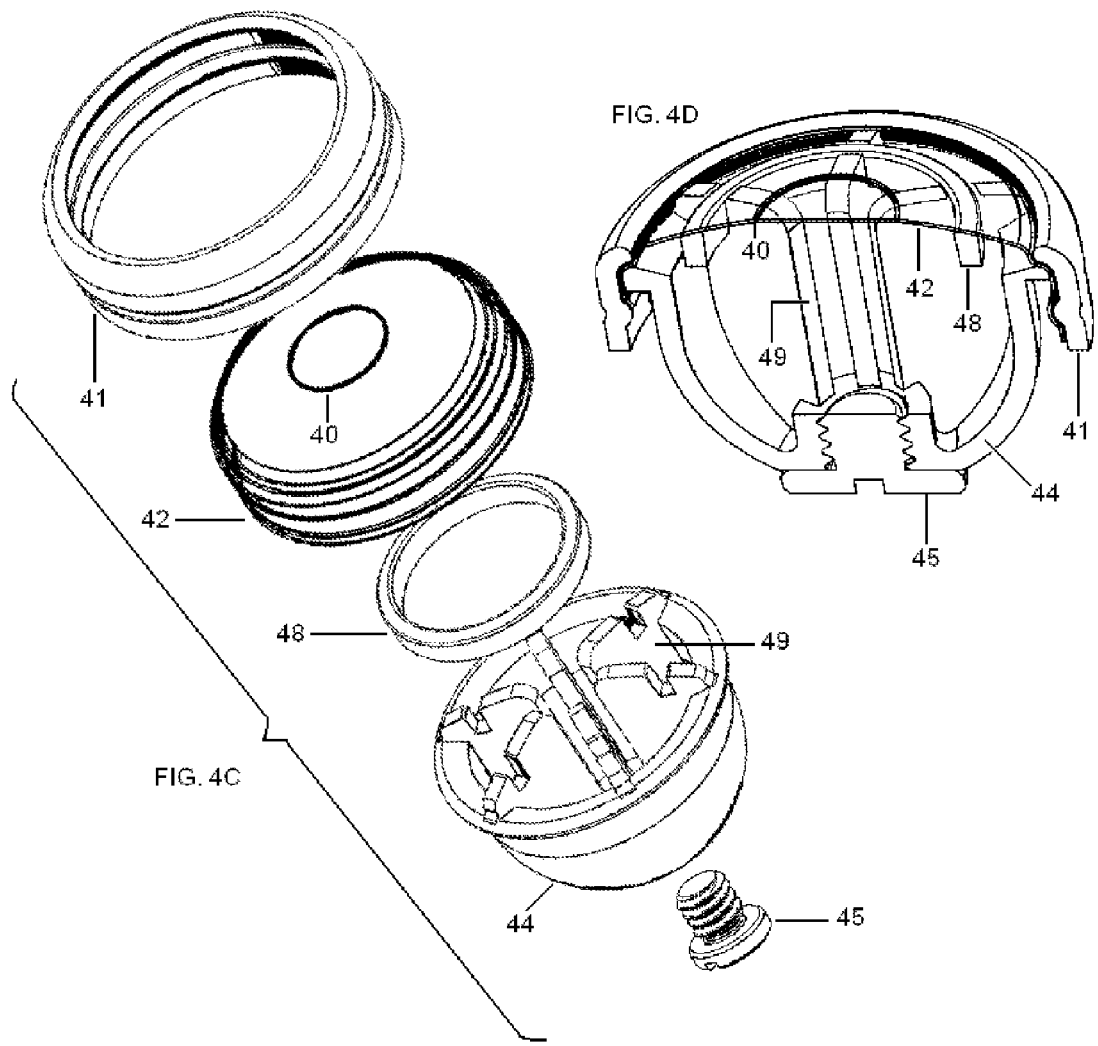

NON-INVASIVE VAGUS NERVE STIMULATION DEVICES AND METHODS TO TREAT OR AVERT ATRIAL FIBRILLATION

CROSS REFERENCE TO RELATED APPLICATIONS

This application claims the benefit of priority of U.S. Provisional Patent Application No. 61/585,668 filed Jan. 12, 2012; which is incorporated herein by reference in its entirety.

BACKGROUND OF THE INVENTION

The field of the present invention relates to the delivery of energy impulses (and/or fields) to bodily tissues for therapeutic or for prophylactic purposes. It relates more specifically to the use of non-invasive devices and methods for transcutaneous electrical nerve stimulation and magnetic nerve stimulation, in order to treat or avert atrial fibrillation (AF) in a patient, using energy that is delivered by such devices. According to the invention, a patient who is experiencing AF, or who is at risk for developing AF, is monitored, preferably using ambulatory or noninvasive sensors; signals from the sensors are analyzed in order to design, produce or adjust parameters of transcutaneous electrical nerve stimulation or magnetic nerve stimulation of a patient, preferably of a vagus nerve; and the stimulation is intended to avert, prevent, delay, abort, shorten, or ameliorate the AF.

The use of electrical stimulation for treatment of medical conditions has been well known in the art for nearly two thousand years. It has been recognized that electrical stimulation of the brain and/or the peripheral nervous system and/or direct stimulation of the malfunctioning tissue holds significant promise for the treatment of many ailments, because such stimulation is generally a wholly reversible and non-destructive treatment.

One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference).

Another application of electrical stimulation of nerves has been the treatment of radiating pain in the lower extremities by stimulating the sacral nerve roots at the bottom of the spinal cord (see U.S. Pat. No. 6,871,099 to WHITEHURST, et al., the disclosure of which is incorporated herein by reference).

Many such therapeutic applications of electrical stimulation involve the surgical implantation of electrodes within a patient. In contrast, devices used for the medical procedures that are disclosed here stimulate nerves by transmitting energy to nerves and tissue non-invasively, thereby offering the patient an option that does not involve surgery. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that invasive procedures do involve inserting a substance or device into or through the skin or into an internal body cavity beyond a body orifice. For example, transcutaneous electrical nerve stimulation (TENS) is non-invasive because it involves attaching electrodes to the surface of the skin (or using a form-fitting conductive garment) without breaking the skin. In contrast, percutaneous electrical stimulation of a nerve is minimally invasive because it involves the introduction of an electrode under the skin, via needle-puncture of the skin (see commonly assigned co-pending US Patent Application 2010/0241188, entitled Percutaneous Electrical Treatment of Tissue to ERRICO et al, which is hereby incorporated by reference in its entirety).

Potential advantages of non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures generally present fewer problems with biocompatibility. In cases involving the attachment of electrodes, non-invasive methods have less of a tendency for breakage of leads, and the electrodes can be easily repositioned if necessary. Non-invasive methods are sometimes painless or only minimally painful and may be performed without the need for even local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be reduced relative to comparable invasive procedures.

Non-invasive transcutaneous electrical nerve stimulation (TENS) electrodes were developed originally for treating different types of pain, including pain in a joint or lower back, cancer pain, post-operative pain, post-traumatic pain, and pain associated with labor and delivery. As TENS was being developed to treat pain, non-invasive electrical stimulation using body-surface electrodes was simultaneously developed for additional therapeutic or diagnostic purposes, which are known collectively as electrotherapy. Neuromuscular electrical stimulation (NMES) stimulates normally innervated muscle in an effort to augment strength and endurance of normal (e.g., athletic) or damaged (e.g., spastic) muscle. Functional electrical stimulation (FES) is used to activate nerves innervating muscle affected by paralysis resulting from spinal cord injury, head injury, stroke and other neurological disorders, or muscle affected by foot drop and gait disorders. FES is also used to stimulate muscle as an orthotic substitute, e.g., replace a brace or support in scoliosis management. Another application of surface electrical stimulation is chest-to-back stimulation of tissue, such as emergency defibrillation and cardiac pacing. Surface electrical stimulation has also been used to repair tissue, by increasing circulation through vasodilation, by controlling edema, by healing wounds, and by inducing bone growth. Surface electrical stimulation is also used for iontophoresis, in which electrical currents drive electrically charged drugs or other ions into the skin, usually to treat inflammation and pain, arthritis, wounds or scars.

Stimulation with surface electrodes may also be used to evoke a response for diagnostic purposes, for example in peripheral nerve stimulation (PNS), which evaluates the ability of motor and sensory nerves to conduct and produce reflexes. Surface electrical stimulation is also used in electroconvulsive therapy to treat psychiatric disorders; electroanesthesia, for example, to prevent pain from dental procedures; and electrotactile speech processing to convert sound into tactile sensation for the hearing impaired. All of the above-mentioned applications of surface electrode stimulation are intended not to damage the patient, but if higher currents are used with special electrodes, electrosurgery may be performed as a means to cut, coagulate, desiccate, or fulgurate tissue [Mark R. PRAUSNITZ. The effects of electric current applied to skin: A review for transdermal drug delivery. Advanced Drug Delivery Reviews 18 (1996): 395-425].

Another form of non-invasive electrical stimulation is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body, inducing at a distance an electric field and electric current within electrically-conducting bodily tissue. The electrical circuits for magnetic stimulators are generally complex, expensive, and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006.

Despite its attractiveness, non-invasive electrical stimulation of a nerve is not always possible or practical. This is primarily because the stimulators may not be able to stimulate a deep nerve selectively or without producing excessive pain, because the stimulation may unintentionally stimulate nerves other than the nerve of interest, including nerves that cause pain. For this reason, forms of electrical stimulation other than TENS may be best suited for the treatment of particular types of pain [Paul F. WHITE, Shitong Li and Jen W. Chiu. Electroanalgesia: Its Role in Acute and Chronic Pain Management. Anesth Analg 92 (2001):505-13]. Accordingly, there remains a long-felt but unsolved need to stimulate nerves totally non-invasively, selectively, and essentially without producing pain.

As compared with what would be experienced by a patient undergoing non-invasive stimulation with conventional TENS or magnetic stimulation methods, the stimulators disclosed herein produce relatively little pain for a given depth of stimulus penetration, but nevertheless stimulate the target nerve to achieve therapeutic results. Or conversely, for a given amount of pain or discomfort on the part of the patient (e.g., the threshold at which such discomfort or pain begins), the stimulators disclosed herein achieve a greater depth of penetration or power of the stimulus under the skin. When some nerves are stimulated electrically, they may produce undesirable responses in addition to the therapeutic effect that is intended. For example, the stimulated nerves may produce unwanted muscle twitches. The stimulators disclosed herein selectively produce only the intended therapeutic effect when they are used to stimulate the target nerve.

The stimulators disclosed here are particularly useful for performing noninvasive stimulation of a vagus nerve in the neck. Invasive vagus nerve stimulation (VNS, also known as vagal nerve stimulation) was developed initially for the treatment of partial onset epilepsy and was subsequently developed for the treatment of depression and other disorders. In those applications, the left vagus nerve is ordinarily stimulated at a location within the neck by first surgically implanting an electrode there, then connecting the electrode to an electrical stimulator [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al and U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042-1060; GROVES DA, Brown V. J. Vagal nerve stimulation: a review of its applications and potential mechanisms that mediate its clinical effects. Neurosci Biobehav Rev (2005) 29:493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3, 2008):E9, pp. 1-4]. An advantage of devices according to the present invention is that they can be used to perform VNS noninvasively on the neck (and other locations) without causing pain or nonselective nerve stimulation.

The devices disclosed here could also be used to treat epilepsy or depression, but the present invention is directed to the use of noninvasive vagus nerve stimulation to treat or prevent a different disorder having a sudden onset, namely, atrial fibrillation (AF). AF is a cardiac rhythm disturbance in which the duration of successive heartbeats (ventricular contractions) is apparently random or "irregularly irregular". In most cases, low-amplitude oscillations (f-waves or fibrillations of the atrium) also appear on the patient's electrocardiogram. In contrast to a normal heart rhythm (normal sinus rhythm), which exhibits variability of heartbeat duration that is due to exercise, respiration, changes in posture, and the like, the duration of a heartbeat in AF is typically independent of the durations of previous and successive heartbeats for many patients. In newly diagnosed AF, an abnormally fast heart rate of 100 to 160 beats per minute is also common.

Although AF is not an immediately life-threatening arrhythmia, and some 30-40% of patients with AF may not complain of any symptoms, many patients with AF may experience considerable discomfort, with complaints of a racing heart rate, palpitations or chest pain, shortness of breath especially on exertion, fatigue, and/or light-headedness. More than 2.3 million individuals experience AF in the United States. Its prevalence increases with age, such that approximately 10% of all individuals over the age of 80 have AF. The total cost for hospital admissions and office visits for AF in the United States in 2005 was 6.65 billion dollars, which is projected to increase along with the increasing number of elderly individuals in the population.

The greatest danger to the AF patient is the significantly increased likelihood of a stroke, due to the tendency of clots to form in their poorly contracting atria. It is estimated that 20-25% of all strokes are caused by AF, and they are more severe than those caused by other factors. Other than strokes, the greatest risk to the AF patient is that rapid heart rate caused by AF can lead to cardiomyopathy and left ventricular dysfunction, which in turn can promote AF in a vicious cycle. Thus, more than 40% of individuals who experience AF will also experience congestive heart failure sometime in their lives. Even after accounting for such coexisting cardiovascular conditions, an individual with AF has an increased likelihood of premature death.

The AF of some patients may have a recognized cause that is temporary, correctable or avoidable, such as alcohol consumption or hyperthyroidism. However, most cases of AF cannot be attributed to a particular set of causes and are treated accordingly. Currently, major goals in the treatment of AF are the prevention of stroke, usually with the aid of anti-coagulation medications, and the relief of symptoms such as rapid heart rate. This is preferably accomplished by terminating the AF, or treating the symptoms if conversion to normal sinus rhythm is not successful.

If a decision is made to attempt to convert AF into a normal heart rhythm, noninvasive pharmacological and transthoracic electrical shock methods have been developed to do so. In more than 90 percent of cases, a normal heart rhythm can be restored shortly with such a cardioversion. However, more than 70 percent of the patients will again experience AF within a year of the cardioversion if they are not placed on antiarrhythmic drugs for heart rhythm control, and even then a significant number of patients relapse into AF. Furthermore, the potential benefit of maintaining normal heart rhythm with antiarrhythmic drugs is negated by potential adverse effects of those drugs, including increased mortality. Therefore, invasive methods for terminating the AF have also been developed, for patients with recurrent or persistent AF that cannot be treated adequately by noninvasive pharmacological or electrical cardioversion. These invasive methods include radiofrequency catheter ablation of ectopic foci within the atria that may be responsible for the AF, and the placement of multiple surgical lesions in the atrium to compartmentalize the atria into regions that cannot support AF [Fred MORADY and Douglas P. Zipes. Atrial Fibrillation: Clinical Features, Mechanisms, and Management. Chapter 40 in: Braunwald's Heart Disease—A Textbook of Cardiovascular Medicine, 9th ed. (2011), Robert O. Bonow, Douglas L. Mann, Douglas P. Zipes and Peter Libby, eds. Philadelphia: Saunders, pp. 825-844].

Partial denervation of the vagus or other autonomic nerves has sometimes also been used to treat AF, ordinarily in conjunction with invasive ablation on or around an ectopic focus, e.g., circumferential isolation of the pulmonary vein. Electrical stimulation of the vagus nerve has been proposed as another treatment for AF, which would have an advantage over vagus denervation in that effects of stimulation would generally not be irreversible. However, vagus nerve stimulation as an intervention for AF has only been attempted invasively and only in animal experiments that may not be a good model of AF in humans.

At one time, electrical stimulation of the vagus nerve (especially the right vagus nerve) was considered to invariably exacerbate the dangers of AF. In fact, electrical stimulation of a vagus nerve has long been used to induce AF in animals. However, data from recent animal experiments indicate that vagus nerve stimulation might also be protective against AF, provided that parameters of the nerve stimulation are properly selected [ZHANG Y, Mazgalev T N. Arrhythmias and vagus nerve stimulation. Heart Fail Rev 16(2, 2011):147-61]. Such animal experiments demonstrate that if the intensity of right or bilateral vagus nerve stimulation is below that which would ordinarily produce a slowing of the normal heart rate, the stimulation might prevent or terminate AF, and it may even inhibit or reverse progressive changes in the heart that are associated with the progression from paroxysmal to permanent AF [LI S, Scherlag B J, Yu L, Sheng X, Zhang Y, Ali R, Dong Y, Ghias M, Po S S. Low-level vagosympathetic stimulation: a paradox and potential new modality for the treatment of focal atrial fibrillation. Circ Arrhythm Electrophysiol 2(6, 2009):645-51; SHA Y, Scherlag B J, Yu L, Sheng X, Jackman W M, Lazzara R, Po S S. Low-Level Right Vagal Stimulation: Anticholinergic and Antiadrenergic Effects. J Cardiovasc Electrophysiol 22(10, 2011):1147-53; SHENG X, Scherlag B J, Yu L, Li S, Ali R, Zhang Y, Fu G, Nakagawa H, Jackman W M, Lazzara R, Po S S. Prevention and reversal of atrial fibrillation inducibility and autonomic remodeling by low-level vagosympathetic nerve stimulation. J Am Coll Cardiol 57(5, 2011):563-71; YU L, Scherlag B J, Li S, Sheng X, Lu Z, Nakagawa H, Zhang Y, Jackman W M, Lazzara R, Jiang H, Po S S. Low-level vagosympathetic nerve stimulation inhibits atrial fibrillation inducibility: direct evidence by neural recordings from intrinsic cardiac ganglia. J Cardiovasc Electrophysiol 22(4, 2011):455-63; ZHANG Y, Ilsar I, Sabbah H N, Ben David T, Mazgalev T N. Relationship between right cervical vagus nerve stimulation and atrial fibrillation inducibility: therapeutic intensities do not increase arrhythmogenesis. Heart Rhythm. 6(2, 2009):244-50].

The present invention is intended to address several impediments to the development of those observations from animal experimentation into a useful AF treatment for humans. First, it increases the number and types of individuals for whom vagus nerve stimulation might be undertaken as a potential treatment for AF, for the following reasons. Some patients in whom a vagus nerve electrode has already been implanted in connection with the treatment of epilepsy or depression might also be candidates for treatment of AF by vagus nerve stimulation. Although the patient's electrode would ordinarily have been implanted to stimulate the left vagus nerve, rather than the right vagus nerve that may be more suitable for treatment of AF, stimulation of the previously implanted electrode may nevertheless be effective for treating AF, provided that parameters of the stimulation protocol are selected according to methods that are disclosed here. However, the general population of AF patients would prefer non-invasive vagus nerve stimulation to the surgical implantation of a vagus nerve stimulator, especially if the non-invasive stimulator produces little or no pain and does not generate unwanted side effects, but nevertheless stimulates the vagus nerve to achieve the intended therapeutic results. Individuals with paroxysmal AF may be particularly disinclined to undergo the implantation of a vagus nerve stimulator solely for the treatment of a medical problem that arises only intermittently. Furthermore, the present invention contemplates the use of non-invasive vagal nerve stimulation as a prophylaxis against imminent AF, rather than only treating AF that is in progress. Thus, an individual who is disinclined to undergo the implantation of a vagus nerve stimulator for purposes of AF treatment would be even more disinclined to undergo its implantation only for purposes of AF prophylaxis.

Second, the present invention addresses the problem of selecting nerve stimulation parameters on an individualized basis for the treatment of AF. For example, in the above-cited animal experiments, vagus nerves were stimulated at a fixed frequency (20 Hz). However, as disclosed herein, it may be more effective to stimulate the vagus nerve at a frequency that is motivated by the frequency of fibrillation of the patient's atria, as reflected in f-waves in the patient's electrocardiogram. Furthermore, because the frequency of fibrillation of the atria may fluctuate, the present invention contemplates the use of feedback and feed-forward methods to continuously adapt the parameters of the stimulation to the changing electrophysiological properties of the patient's heart.

A third problem that the present invention addresses is the avoidance of episodes of AF in patients who are at risk for experiencing them. Methods have been described for predicting that an episode of AF may be imminent, but specific proposed uses for such knowledge have been limited to those involving implanted atrial pacemakers [G B MOODY, A L Goldberger, S McClennen, S P Swiryn. Predicting the onset of paroxysmal atrial fibrillation: the Computers in Cardiology Challenge 2001. Computers in Cardiology 28 (2001):113-116]. Accordingly, the present invention discloses noninvasive methods to avert AF that may be suitable for use with the general population of AF patients, namely, noninvasive vagal nerve stimulation, along with disclosed nerve stimulation parameters that might be used for that purpose. Original onset-of-AF forecasting methods are also disclosed, which are based upon the automatic analysis of physiological and/or environmental signals that are provided preferably by non-invasive sensors situated on, about, or near the patient. Such sensors may comprise those used in conventional Holter and bedside monitoring applications, for monitoring heart rate, ECG, respiration, core temperature, hydration, blood pressure, brain function, oxygenation, and skin temperature. The sensors may also be embedded in garments or placed in sports wristwatches, as currently used in programs that monitor the physiological status of soldiers [G. A. Shaw, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141].

SUMMARY OF THE INVENTION

In one aspect of the invention, devices and methods are described to produce therapeutic or prophylactic effects in a patient by utilizing an energy source that transmits energy non-invasively to nervous tissue. In particular, the disclosed devices can transmit energy to, or in close proximity to, a vagus nerve in the neck of the patient, in order to temporarily stimulate, block and/or modulate electrophysiological signals in that nerve. The methods that are disclosed here comprise stimulating a vagus nerve with particular stimulation waveform parameters, preferably using the nerve stimulator devices that are also described herein.

A novel stimulator device is used to modulate electrical activity of a vagus nerve or other nerves or tissue. The stimulator comprises a source of electrical power and two or more remote electrodes that are configured to stimulate a deep nerve relative to the nerve axis. The device also comprises continuous electrically conducting media with which the electrodes are in contact. The conducting medium is also in contact with an interface element that makes physical contact with the patient's skin. The interface element may be electrically insulating (dielectric) material, such as a sheet of Mylar, in which case electrical coupling of the device to the patient is capacitive. In other embodiments, the interface element is electrically conducting material, such as an electrically conducting or permeable membrane, in which case electrical coupling of the device to the patient is ohmic. The interface element may have a shape that conforms to the contour of a target body surface of a patient when the medium is applied to the target body surface. In another aspect of the invention, a non-invasive magnetic stimulator device is used to modulate electrical activity of a vagus nerve or other nerves or tissue, without actually introducing a magnetic field into the patient.

For the present medical applications, the electrode-based device or a magnetic stimulation device is ordinarily applied to the vicinity of the patient's neck. In one embodiment of the electrode-based invention, the stimulator comprises two electrodes that lie side-by-side within separate stimulator heads, wherein the electrodes are separated by electrically insulating material. Each electrode is in continuous contact with an electrically conducting medium that extends from the interface element of the stimulator to the electrode. The interface element also contacts the patient's skin when the device is in operation. The conducting media for different electrodes are also separated by electrically insulating material.

In another embodiment of the invention, a non-invasive magnetic stimulator device is ordinarily applied to the vicinity of the patient's neck. In a preferred embodiment of the magnetic stimulator, the stimulator comprises two toroidal windings that lie side-by-side within separate stimulator heads, wherein the toroidal windings are separated by electrically insulating material. Each toroid is in continuous contact with an electrically conducting medium that extends from the patient's skin to the toroid.

A source of power supplies a pulse of electric charge to the electrodes or magnetic stimulator coil, such that the electrodes or magnetic stimulator produce an electric current and/or an electric field within the patient. The electrical or magnetic stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m and an electrical field gradient of greater than 2 V/m/mm.

Current passing through an electrode may be about 0.01 to 40 mA, with voltage across the electrodes of 0.01 to 30 volts. The current is passed through the electrodes in bursts of pulses. There may be 1 to 20 pulses per burst, preferably five pulses. Each pulse within a burst has a duration of 20 to 1000 microseconds, preferably 200 microseconds. A burst followed by a silent inter-burst interval repeats at 1 to 5000 bursts per second (bps), preferably at 15-50 bps. The preferred shape of each pulse is a full sinusoidal wave. The preferred stimulator shapes an elongated electric field of effect that can be oriented parallel to a long nerve, such as a vagus nerve in a patient's neck. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves that produce pain. The suitable waveform and parameters are also selected so that when the target nerve is stimulated, only desired therapeutic or prophylactic effects are preferentially produced.

The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses as described above, shaping an elongated electrical field of effect as with the electrode-based stimulator.

The stimulation is performed with a sinusoidal burst waveform as described above, followed by silent inter-burst period, which repeats itself with a period of T. For example, the sinusoidal period τ may be 200 microseconds; the number of pulses per burst may be N=5; and the whole pattern of burst followed by silent inter-burst period may have a period of T=40000 microseconds, which is comparable to 25 Hz stimulation.

More generally, there may be 1 to 20 pulses per burst, preferably five pulses. Each pulse within a burst has a duration of 20 to 1000 microseconds, preferably 200 microseconds. A burst followed by a silent inter-burst interval repeats at 1 to 5000 bursts per second (bps), preferably at 5 to 50 bps, more preferably 10 to 25 bps stimulation (comparable to 10-25 Hz), and even more preferably at 20 bps. Although the preferred shape of each pulse is a full sinusoidal wave, triangular or other shapes known in the art may be used as well. The stimulation is performed typically for 30 minutes. Treatment may be performed on the right or both or left vagus nerves, and it may be performed alternately on the left and right vagus nerves.

Teachings of the present invention demonstrate how to treat a patient, by positioning the disclosed noninvasive stimulator devices against body surfaces, particularly at a location in the vicinity of the patient's neck where a vagus nerve is located under the skin. In particular, the disclosure teaches methods for treating atrial fibrillation with the disclosed stimulators.

The disclosure also teaches methods for the forecasting of an imminent episode of atrial fibrillation and using the disclosed stimulators to avert the fibrillation. Models for making the forecast of imminent AF may be grey-box models that incorporate knowledge of the heart's anatomy and mechanisms. They may also be black box models, particularly models that make use of support vector machines. Data for making the forecasts are from physiological and/or environmental signals from sensors located on or about the patient. In particular, data extracted from an electrocardiogram is used to make the forecasts.

Treating or averting of an episode of atrial fibrillation is implemented within the context of control theory. A controller comprising, for example, the disclosed vagus nerve stimulator, a PID, and a feedforward model, provides input to the nerves of the heart via stimulation of one or both of the patient's vagus nerves. For a patient in AF, output from the patient's heart is monitored using sensors, such output comprising indices characterizing one or more peaks within the spectrum of the patient's atrial electrocardiogram. The output may be used to produce feedback by the controller, which uses the output to set parameters of the vagus nerve stimulation, preferably in such a way as to capture peaks within the spectrum of the atrial electrocardiogram and to then reduce the characteristic frequencies of the peaks, until the AF is no longer able to sustain itself.

For patients who are in normal sinus rhythm, but who are at risk for the onset of an episode of atrial fibrillation, the controller also tracks output from the patient's heart, the output comprising heart rate variability indices of parasympathetic and sympathetic tone; indices of P-wave morphology, duration and dispersion; and the frequency of atrial premature beats. In closed-loop mode, the controller continuously selects parameters for the vagus nerve stimulation, in such a way as to maintain fluctuations of the indices in the vicinity of their normal values. Otherwise, the controller may be used to forecast imminence of the onset of AF, using continuously acquired values of the indices to make the forecast. Upon warning by the controller of the imminent onset of AF, the patient or a caregiver then applies the vagus nerve stimulator, using stimulation parameters that previously had been selected when the controller was tuned for use in closed-loop mode.

However, it should be understood that application of the methods and devices is not limited to the examples that are given. The novel systems, devices and methods for treating conditions using the disclosed stimulator or other non-invasive stimulation devices are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 2A illustrates an exemplary electrical voltage/current profile for the present invention.

FIG. 2B illustrates an exemplary waveform for modulating impulses that are applied to a nerve according to the present invention.

FIG. 2C illustrates another exemplary waveform for modulating impulses that are applied to a nerve according to the present invention.

FIG. 3A is a perspective view of a dual-electrode stimulator according to another embodiment of the present invention.

FIG. 3B is a cut-a-way view of the stimulator of FIG. 3A.

FIG. 4C is a perspective view of an alternative embodiment of the head of the stimulator of FIG. 3A.

FIG. 4D is a cut-a-way view of the head of FIG. 4C.

DETAILED DESCRIPTION OF THE PREFERRED EMBODIMENTS

Figure 1A:
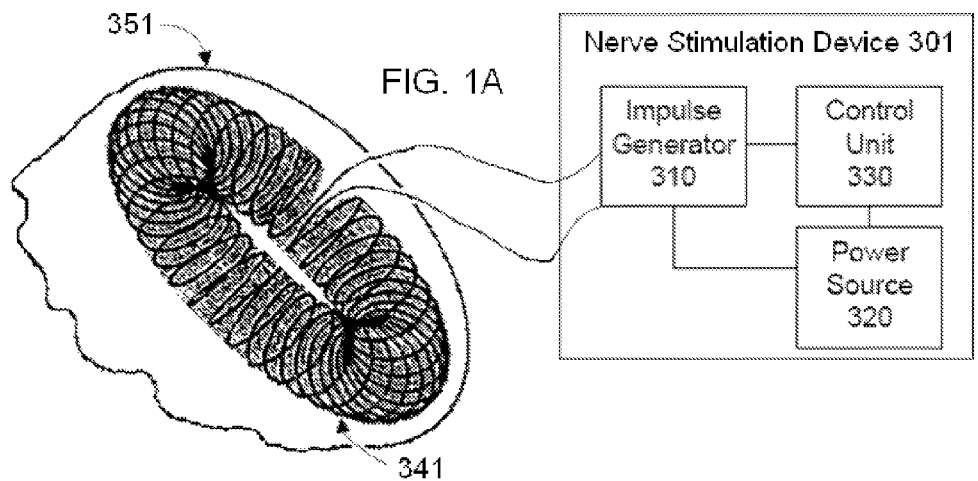
FIG. 1A is a schematic view of a nerve modulating device according to the present invention which supplies controlled pulses of electrical current to a magnetic stimulator coil.

In the present invention, energy is transmitted non-invasively to a patient using novel electrode-based and/or magnetic stimulation devices that are designed to meet a long-felt but unsolved need to stimulate nerves electrically, totally non-invasively, selectively, and essentially without producing pain. The invention is also designed to produce electrical impulses that interact with the signals of one or more target nerves to achieve a therapeutic result. In particular, the devices and methods are intended to stimulate a vagus nerve non-invasively at a location in a patient's neck, in order to treat atrial fibrillation, or to detect and avert the onset of an imminent episode of atrial fibrillation.

Atrial fibrillation (AF) is a cardiac rhythm disturbance in which the duration of successive heartbeats (ventricular contractions of the heart) is apparently random or "irregularly irregular". In most cases, low-amplitude oscillations (f-waves due to fibrillatory quivering of the heart's atria) also appear on the patient's electrocardiogram. In contrast to a normal heart rhythm (normal sinus rhythm), which exhibits variability of heartbeat duration that is associated with autonomic and humoral influences due to exercise, respiration, changes in posture, and the like, the duration of a heartbeat in AF is typically independent of the durations of previous and successive heartbeats for many patients [HORAN L G, Kistler J C. Study of ventricular response in atrial fibrillation. Circ Res 9 (1961):305-11; John M RAWLES and Edward Rowland. Is the pulse in atrial fibrillation irregularly irregular? Br Heart J 56:4-11; U Rajendra ACHARYA, Paul Joseph K, Kannathal N, Lim C M, Suri J S. Heart rate variability: a review. Med Biol Eng Comput 44(12, 2006):1031-51].

Heartbeat intervals in AF often have a statistical distribution (e.g., approximately gaussian) with a mean that is significantly smaller than the heartbeat duration that is experienced when the patient has a normal sinus rhythm. Thus, during AF, a tachycardic heartrate of 100 to 160 beats per minute is common. If the AF patient has an even higher heart rate, the randomness of the inter-beat interval may be difficult to discern, in which case the AF could be confused with another form of supraventricular tachycardia.

Some AF patients may exhibit heart rhythms that alternate spontaneously between AF and normal sinus rhythm, in which case the AF is known as paroxysmal AF. For such patients, the episodes of AF may persist for seconds to a few days. Paroxysmal AF is sometimes subclassified as vagotonic versus adrenergic, if the paroxysms of AF consistently occur respectively when the patient is at rest or asleep, versus after strenuous exercise. However, most patients with paroxysmal AF have no consistent pattern of onset. If the AF persists for seven or more days, it is known as persistent AF. In patients with predominantly persistent AF, interventions may be performed in an attempt to terminate the AF, as described below. For patients with year-long persistent AF in whom the interventions have been unsuccessful or foregone, the AF may be termed permanent or longstanding, respectively.

AF is a progressive disorder. In its early stage, many episodes of AF may be asymptomatic and rapidly self-terminating. Over decades, however, the episodes become longer and more frequent, and without treatment, the AF may eventually become permanent. The progression is partly caused by AF itself, because AF produces electrophysiological, biochemical, and structural changes to the heart (remodeling) that promote longer and more frequent episodes of AF. Examples of changes that may occur during remodeling are: reduction of transient outward K current and L-type Ca current in myocytes, calcium handling abnormalities, superoxide production, fibrosis over the long term, and increased innervation of the atrial sympathetic nervous system.

In fewer than 10% of cases, AF is observed in the absence of underlying structural or physiological abnormalities (termed "lone AF" for patients under 60 years of age). Patients who experience the arrhythmia known as atrial flutter very often experience AF, and vice versa, which is understandable considering that the underlying pathophysiologies of these two arrhythmias are related. Thus, the f-waves seen in the electrocardiogram of a patient with atrial flutter are constant in rate and morphology, whereas the f-waves for an AF patient are variable in shape, rate, and amplitude [Albert L. WALDO. The interrelationship between atrial fibrillation and atrial flutter. Progress in Cardiovascular Diseases 48(1, 2005):41-56]. Paroxysmal atrial fibrillation may also occur frequently in patients with paroxysmal supraventricular tachycardia [CHEN Y J, Chen S A, Tai C T, Wen Z C, Feng A N, Ding Y A, Chang M S. Role of atrial electrophysiology and autonomic nervous system in patients with supraventricular tachycardia and paroxysmal atrial fibrillation. J Am Coll Cardiol 32(3, 1998):732-8].

The progression of AF may reflect changes in the structure of the heart and cardiovascular system that accompany other diseases. Thus, hypertension, vascular disease, heart failure, valvular heart disease (especially mitral valve disease), diabetes mellitus, and thyroid disease are all risk factors for the development of AF. More subtle structural changes that accompany aging, such as atrial dilation, myocyte hypertrophy, loss of sarcomeres, accumulation of glycogen, mitochondrial abnormalities, and interstitial fibrosis, may also be unobserved risk factors. Consequently, advancing age is also a significant risk factor for AF. A simple scoring test is available to predict the likelihood that an individual will develop AF, based upon the existence of such predisposing factors [SCHNABEL R B, Sullivan L M, Levy D, Pencina M J, Massaro J M, D'Agostino R B Sr, Newton-Cheh C, Yamamoto J F, Magnani J W, Tadros T M, Kannel W B, Wang T J, Ellinor P T, Wolf P A, Vasan R S, Benjamin E J. Development of a risk score for atrial fibrillation (Framingham Heart Study): a community-based cohort study. Lancet 373(9665, 2009):739-45].

Although AF is not an immediately life-threatening arrhythmia, and some 30-40% of patients with AF may not complain of any symptoms, many patients with AF may experience considerable discomfort and complain of a racing heart rate, palpitations or chest pain, shortness of breath especially on exertion, fatigue, and/or light-headedness. The greatest risk to the AF patient is the significantly increased likelihood of a stroke, due to the tendency of clots to form in their poorly contracting atria. In that regard, patients with paroxysmal and permanent AF have similar risks for experiencing strokes, which is a risk 3 to 5 times that of an individual without AF. It is estimated that 20-25% of all strokes are caused by AF, and they are more severe than those caused by other factors. Other than strokes, the most significant risk to the AF patient is that rapid heart rate caused by AF can lead to cardiomyopathy and left ventricular dysfunction, which in turn can promote AF in a vicious cycle. Thus, more than 40% of individuals who experience AF will also experience congestive heart failure sometime in their lives. Even after accounting for such coexisting cardiovascular conditions, an individual with AF has an increased likelihood of premature death [TSANG T S, Miyasaka Y, Barnes M E, Gersh R E Epidemiological profile of atrial fibrillation: a contemporary perspective. Prog Cardiovasc Dis. 48(1, 2005):1-8; BENJAMIN E J, Wolf PA, D'Agostino R B, Silbershatz H, Kannel W B, Levy D. Impact of atrial fibrillation on the risk of death: the Framingham Heart Study. Circulation 98(10, 1998):946-52].

More than 2.3 million individuals experience AF in the United States. Its prevalence increases with each decade of age, so that approximately 10% of all individuals over the age of 80 have AF. For individuals greater than 40 years of age, the risk of eventually experiencing AF is 1 in 6 in individuals without predisposing factors and 1 in 4 among all individuals. Males are more likely to experience AF than females. There are more hospital admissions for AF than for any other arrhythmia. The total cost for hospital admissions and office visits for AF in the United States in 2005 was 6.65 billion dollars, or an average of $3600 per AF patient [KANNEL W B, Benjamin E J. Current perceptions of the epidemiology of atrial fibrillation. Cardiol Clin. 27(1, 2009):13-24].

The mechanism by which AF produces apparently random or "irregularly irregular" ventricular contractions is understood as follows. The mammalian heart has four chambers, consisting of left and right atria and ventricles. The muscle surrounding all chambers of the heart contracts in a coordinated manner to pump the blood, in which the atria contract before the ventricles. Earlier contraction of the atria is due to the fact that the heart muscle is electrically excitable tissue, and its contraction is coupled to the passage of electrical waves that normally begin in the pacemaker region of the sino-atrial (SA) node of the right atrium. The electrical wave that is initiated at the SA node passes across the atrium to the atrioventricular (AV) node in the lower right atrium, which is delayed there before being conducted to the ventricles through the Bundle of His. Once the electrical wave is conducted to the ventricles, they complete the cardiac cycle by contracting, and then recover to make possible a subsequent contraction.

In a normal electrocardiogram (ECG), this sequence of electrical excitation and contraction corresponds to a series of structures in the ECG. The P wave corresponds to an electrical wave passing from the SA node across the right atrium to the AV node and to the left atrium. This is followed by a QRS complex corresponding to depolarization of both ventricles, which is then followed by a T wave, corresponding to repolarization of the ventricles. In atrial fibrillation, the electrical waves that are initiated by the SA node are overwhelmed by disorganized electrical waves that originate elsewhere in the atria, often near the roots of the pulmonary veins. Such waves may occur at a high rate, but most of them do not result in contraction of the ventricles. This is because once such a wave reaches the AV node to initiate contraction of the ventricles, subsequent waves reaching the AV node cannot initiate a ventricular contraction until conduction of the earlier wave through the AV node is complete. Thus, although patients with AF may experience a high heart rate, the rate of ventricular contraction is limited by the electrical gatekeeping role of the AV node and associated fibers that conduct impulses from the atria to the ventricles. However, because the successfully conducted waves reach the AV node at irregular intervals, the time between heart beats (e.g., time between QRS complexes associated with ventricular contraction) of an AF patient appears to be random or chaotic, and the atria themselves quiver (fibrillate). Furthermore, the electrical activity associated with the quivering results in low-amplitude oscillations (f-waves) on the AF patient's electrocardiogram, and the P wave that would correspond to the coordinated electrical activity of normally contracting atria is absent.

It is generally agreed that AF is produced by localized or multiple non-localized sources of electrical waves that are generally distant from the heart's normal pacemaker region [NATTEL S. New ideas about atrial fibrillation 50 years on. Nature 415(6868, 2002):219-26; JALIFE J, Berenfeld O, Mansour M. Mother rotors and fibrillatory conduction: a mechanism of atrial fibrillation. Cardiovasc Res 54(2, 2002): 204-16; VEENHUYZEN G D, Simpson C S, Abdollah H. Atrial fibrillation. CMAJ 171(7, 2004):755-60; NATTEL S, Shiroshita-Takeshita A, Brundel B J, Rivard L. Mechanisms of atrial fibrillation: lessons from animal models. Prog Cardiovasc Dis 48(1, 2005):9-28; ORAL H. Mechanisms of atrial fibrillation: lessons from studies in patients. Prog Cardiovasc Dis 48(1, 2005):29-40; IWASAKI Y K, Nishida K, Kato T, Nattel S. Atrial fibrillation pathophysiology: implications for management. Circulation 124(20, 2011):2264-74; SCHOTTEN U, Verheule S, Kirchhof P, Goette A. Pathophysiological mechanisms of atrial fibrillation: a translational appraisal. Physiol Rev 91(1, 2011):265-325; Sanjiv M. NARAYAN and David E. Krummen. Dynamics Factors Preceding the Initiation of Atrial Fibrillation in Humans. Heart Rhythm 5(6 Suppl, 2008): S22-S25]. The localized source may be an ectopic focal discharge, or it may be a localized reentrant circuit, wherein the atrial tissue propagates action potentials in such a way that the action potentials loop around so as to reactivate themselves (reentry). The focal discharge may occur in myocytes that can act as automatic pacemakers, but in which the automatic rate has become abnormally high; in myocytes that are not ordinarily automatic pacemakers but have become so; or in myocytes that are triggered to exhibit extra action potentials (delayed afterdepolarizaiton, early afterpolarizations). The reentry circuits may be stable (mother waves) of different sizes that may be determined by anatomical features (circus movements around obstacles) or minimal paths without obstacles (leading circle movements). For leading circle movements, the minimal path of reentrant movement (i.e., the wavelength) is the product of the conduction velocity and the refractory period during which a new action potential may not be initiated. Reentrant circuits may also be unstable but nevertheless able to sustain AF if they continuously reform, provided that at least one such circuit always exists. Reentry may also be due to fixed or wandering rotors, which are spiral- or scroll-shaped micro-reentrant vortices that rotate rapidly around an excitable but unexcited core.

AF due to multiple nonlocalized sources may be due to multiple wavelets that propagate randomly or chaotically throughout the atrium, such that some wavelets may be propagating while others remain fully or partially refractory as the result of a preceding activation. According to this mechanism, AF is a turbulent and self-sustaining process that is made possible by inhomogeneous atrial repolarization, acting independently of its initiating mechanism. High resolution electrode mapping indicates that for this mechanism to sustain AF, there must be at least four to six wavelets simultaneously propagating randomly across the atrium. The smaller the wavelength is (due to conduction slowing, refractory period shortening, or both), then the greater the possible number of wavelets, and consequently, the more easily AF is induced and maintained.

The existence of AF is easily diagnosed from an electrocardiogram, for example, from the irregularity of the time interval between heart beats, the absence of a P wave, and/or the presence of baseline fibrillatory activity (f-waves). Computer-based automatic AF-detection algorithms also search an electrocardiogram for such features [DASH S, Chon K H, Lu S, Raeder E A. Automatic real time detection of atrial fibrillation. Ann Biomed Eng 37(9, 2009):1701-9]. However, the state of the noninvasive clinical diagnostic art is such that detailed characterization of a patient's AF in terms of particular ectopic foci or reentrant movements is not currently possible. The present invention advances the noninvasive diagnostic art by disclosing methods that may be used to obtain such a detailed characterization, in connection with methods for forecasting the time-course of a patient's AF, as described below. Otherwise, methods have been developed to partially quantify a patient's AF. The simplest method is to measure the size in millivolts of the f-waves in leads $V_1$ and lead II of an electrocardiogram, the values of which correlate with the ability to terminate AF [I NAULT et al. Clinical value of fibrillatory wave amplitude on surface ECG in patients with persistent atrial fibrillation. J Interv Card Electrophysiol 26(1, 2009):11-9].

A more powerful group of methods has as its goal the extraction, from a surface electrocardiogram, that portion of the electrocardiogram that is due to atrial electrical activity, separated from the much larger ventricular electrical activity. This may be accomplished, for example, by identifying different types of QRST complexes, averaging those complexes over multiple beats, then subtracting the corresponding averaged QRST complex from the electrocardiogram, so as to extract an atrial electrocardiogram. Alternatively, methods involving principal component analysis may be used to extract the atrial waveform without explicitly subtracting a ventricular waveform, or extraction may be performed during the T-Q interval when no ventricular waveform need be subtracted [BOLLMANN A, Husser D, Mainardi L, Lombardi F, Langley P, Murray A, Rieta J J, Millet J, Olsson S B, Stridh M, Sörnmo L. Analysis of surface electrocardiograms in atrial fibrillation: techniques, research, and clinical applications. Europace 8(11, 2006):911-26; STRIDH M, Bollmann A, Olsson S B, Sörnmo L. Detection and feature extraction of atrial tachyarrhythmias. A three stage method of time-frequency analysis. IEEE Eng Med Biol Mag 25(6, 2006):31-9.; D. A. CORINO, Roberto Sassi, Luca T. Mainardi, Sergio Cerutti. Signal processing methods for information enhancement in atrial fibrillation: spectral analysis and non-linear parameters. Biomedical Signal Processing and Control 1(4, 2006):271-281; Mathieu LEMAY. Data processing techniques for the characterization of atrial fibrillation. 2007 thesis. Ecole Polytechnique Federale de Lausanne. Lausanne, Switzerland. pp. 1-134; R SASSI, VDA Corino, L T Mainardi. Analysis of surface atrial signals using spectral methods for time series with missing data. Computers in Cardiology 34 (2007):153-156; SORNMO L, Stridh M, Husser D, Bollmann A, Olsson S B. Analysis of atrial fibrillation: from electrocardiogram signal processing to clinical management. Philosophical Transactions. Series A, Mathematical, Physical, and Engineering Sciences 367(1887, 2009): 235-53; ABACHERLI R, Leber R, Lemay M, Vesin J M, van Oosterom A, Schmid H J, Kappenberger L. Development of a toolbox for electrocardiogram-based interpretation of atrial fibrillation. J Electrocardiol 42(6, 2009):517-21].

Once an extracted atrial electrocardiogram is available, possibly corresponding preferentially to one or more selected regions of the atria, the cardiogram may then be analyzed in order to partially characterize the patient's AF. For example, construction of the Fourier transform of the atrial electrocardiogram reveals that many patients have single, narrow-banded fibrillatory frequency spectra, with a fibrillatory rate that varies greatly between individuals (typically in the range 4 to 9 Hz). Transforms other than the Fourier transform may also be used [CIACCIO E J, Biviano A B, Whang W, Coromilas J, Garan H. A new transform for the analysis of complex fractionated atrial electrograms. Biomed Eng Online 10 (2011):35]. Patients with persistent AF generally exhibit a peak in their atrial electrocardiogram spectrum at a higher frequency than patients with paroxysmal AF, so that the peak frequency observed in a patient on successive days might serve as an indicator of progressive atrial remodeling or response to a therapy. The width of the frequency spectrum band may be used as an indicator of the dispersion of fibrillation rates, either from the presence of multiple wavelets or from spatiotemporal organization of waves propagating from an ectopic focus to the rest of the atria. In patients who have been treated with anti-arrhythmic drugs, both the peak frequency and the width of the frequency spectrum band have been observed to decrease [HUSSER D, Stridh M, Sornmo L, Platonov P, Olsson S B, Bollmann A. Analysis of the surface electrocardiogram for monitoring and predicting antiarrhythmic drug effects in atrial fibrillation. Cardiovasc Drugs Ther 18(5, 2004):377-86; HUSSER D, Stridh M, Sornmo L, Olsson S B, Bollmann A. Frequency analysis of atrial fibrillation from the surface electrocardiogram. Indian Pacing Electrophysiol J 4(3, 2004):122-36].

The frequency spectrum of the extracted atrial electrocardiogram is generally not stationary, so that it may be useful to plot a spectrogram and/or compare the spectrum over a succession of short time intervals (time-frequency analysis). Thus, over some time periods, the spectrum may briefly exhibit multiple peaks, or the dominant peak may briefly increase its modal frequency. The maximum peak frequency that is observed among the spectra at different times is thought to correlate closely with atrial refractoriness [BOLLMANN A, Husser D, Stridh M, Soernmo L, Majic M, Klein H U, Olsson S B. Frequency measures obtained from the surface electrocardiogram in atrial fibrillation research and clinical decision-making. J Cardiovasc Electrophysiol 14(10 Suppl, 2003):S154-61].

The electrical activity of the atria may exhibit regional differences that may attributable in part to the location of the reentrant loops and/or ectopic foci that give rise to AF. By selecting particular electrocardiographic leads for analysis, it is possible to preferentially extract electrophysiological characteristics of the corresponding portions of the atria. Thus, ECG leads I, $V_5$ and aVL preferentially characterize left atrial activity; leads II, III and $aV_F$ preferentially characterize activity of the inferior atrial surface or coronary sinus; and leads $V_1$, $V_2$, and aVR preferentially characterize right atrial activity [RAVI K C, Krummen D E, Tran A J, Bullinga J R, Narayan S M. Electrocardiographic measurements of regional atrial fibrillation cycle length. Pacing Clin Electrophysiol 32(Suppl 1, 2009):566-71]. Such a regional characterization of the atrium during AF may be augmented using methods that use ultrasound imaging in conjunction with the electrocardiogram [DUYTSCHAEVER M, Heyse A, de Sutter J, Crijns H, Gillebert T, Tavernier R, Tieleman R. Transthoracic tissue Doppler imaging of the atria: a novel method to determine the atrial fibrillation cycle length. J Cardiovasc Electrophysiol. 17(11, 2006):1202-9]. The spatial properties of AF may also be analyzed after constructing vectorcardiogram loops synthesized from 12-lead electrocardiograms [RICHTER U, Stridh M, Bollmann A, Husser D, Sörnmo L. Spatial characteristics of atrial fibrillation electrocardiograms. Electrocardiol 41(2, 2008):165-72]. Such noninvasive measurements may reveal regional heterogeneity that could otherwise be identified only by invasive electrode mapping methods [SANDERS P, Berenfeld O, Hocini M, Jaïs P, Vaidyanathan R, Hsu L F, Garrigue S, Takahashi Y, Rotter M, Sacher F, Scavée C, Ploutz-Snyder R, Jalife J, Haïssaguerre M. Spectral analysis identifies sites of high-frequency activity maintaining atrial fibrillation in humans. Circulation 112 (6, 2005):789-97].

Methods of treating AF have developed continuously for many years [KHASNIS A, Thakur R K. Atrial fibrillation: a historical perspective. Med Clin North Am 92(1, 2008):1-15]. The AF of some patients may have a recognized cause that is temporary, correctable or avoidable [DEVOS C B, Nieuwlaat R, Crijns H J, Camm A J, LeHeuzey J Y, Kirchhof O, Capucci A, Breithardt G, Vardas P E, Pisters R, Tieleman R G. Autonomic trigger patterns and anti-arrhythmic treatment of paroxysmal atrial fibrillation: data from the Euro Heart Survey. Eur Heart J 29(5, 2008):632-9]. Temporary causes include excessive alcohol consumption and recent surgery or infections. The most common correctable cause of AF is hyperthyroidism. Other potential causes of AF, such as hypertension, would be treated, but such treatment may not necessarily bring about a conversion to normal sinus rhythm. However, most cases of AF cannot be attributed to a particular set of causes and are treated accordingly. Currently, major goals in the treatment of AF are the prevention of stroke and the relief of symptoms such as rapid heart rate. This is preferably accomplished by terminating the AF, or treating the symptoms if conversion to normal sinus rhythm is not successful [V FUSTER et al. ACC/AHA/ESC 2006 guidelines for the management of patients with atrial fibrillation—executive summary. Circulation 114 (2006):700-752; LS WANN et al. 2011 ACCF/AHA/HRS focused update on the management of patients with atrial fibrillation (updating the 2006 guideline). Heart Rhythm 8(1, 2011):157-76; A. J. CAMM et al. Guidelines for the management of atrial fibrillation: the Task Force for the Management of Atrial Fibrillation of the European Society of Cardiology (ESC). European Heart Journal 31 (2010):2369-2439; Fred MORADY and Douglas P. Zipes. Atrial Fibrillation: Clinical Features, Mechanisms, and Management. Chapter 40 in: Braunwald's Heart Disease—A Textbook of Cardiovascular Medicine, 9th ed. (2011), Robert O. Bonow, Douglas L. Mann, Douglas P. Zipes and Peter Libby, eds. Philadelphia: Saunders, pp. 825-844].

If the AF patient is seen in the emergency room, it is most likely because of a high heart rate, which may be treated with intravenous diltiazem or esmolol. If the patient is experiencing a first episode of AF, or if the patient previously had normal sinus rhythm for an extended period of time, it is then appropriate to consider promptly attempting to convert the AF to normal sinus rhythm (cardioversion). In part, this is because AF-induced remodeling of the heart may make cardioversion at a later time more difficult. However, if there is reason to believe that the AF would self-terminate, or if the AF may have a temporary or correctable cause, it is appropriate to defer an attempted cardioversion.

Methods are available to predict the spontaneous termination of atrial fibrillation using surface electrocardiograms, so that unnecessary treatment of self-terminating AF may be avoided. Such prediction has even been the subject of a competition [G B MOODY. Spontaneous Termination of Atrial Fibrillation: A Challenge from PhysioNet and Computers in Cardiology 2004. Computers in Cardiology 31 (2004):101-104]. Methods involving the analysis of dominant frequencies in f-waves are used most often, but other methods have been described as well [CHIARUGI F, Varanini M, Cantini F, Conforti F, Vrouchos G. Noninvasive ECG as a tool for predicting termination of paroxysmal atrial fibrillation. IEEE Trans Biomed Eng. 54(8, 2007):1399-406; J D DIAZ, C Gonzales, O Escalona. A support vector machine for predicting spontaneous termination of paroxysmal atrial fibrillation episodes. Computers in Cardiology 33 (2006): 949-952; HAYN D, Kollmann A, Schreier G. Predicting initiation and termination of atrial fibrillation from the ECG. Biomed Tech 52(1, 2007):5-10; NILSSON F, Stridh M, Bollmann A, Sörnmo L. Predicting spontaneous termination of atrial fibrillation using the surface ECG. Med Eng Phys. 28(8, 2006): 802-808; PETRUTIU S, Sahakian A V, Swiryn S. Abrupt changes in fibrillatory wave characteristics at the termination of paroxysmal atrial fibrillation in humans. Europace 9(7, 2007):466-70; VAYA C, Rieta J J. Time and frequency series combination for non-invasive regularity analysis of atrial fibrillation. Med Biol Eng Comput 47(7, 2009):687-96].

If a decision is made to attempt to convert AF into a normal sinus rhythm, pharmacological and electrical methods have been developed to do so [KIM S S, Knight B P. Electrical and pharmacologic cardioversion for atrial fibrillation. Med Clin North Am 92(1, 2008):101-20]. Pharmacological cardioversion is unlikely to succeed if an AF episode has lasted more than 7 days. For episodes that have lasted only a few days, the AF might be terminated by intravenous administration of ibutilide, procainamide, or amiodarone. For patients without structural heart disease, the AF might also be terminated by oral administration of propafenone or flecainide. If the patient has no adverse reaction to the oral drug, the patient may then be a candidate for episodic self-administration of the drug on an outpatient basis.

If pharmacological cardioversion does not succeed, or if the patient's AF has persisted more than 7 days, the AF might be terminated by applying one or more transthoracic electrical shocks, possibly in combination with infused ibutilide. The shocks are painful, so the patient needs to be sedated with a drug such as diazepam. However, for approximately 25% of the patients, the electrical cardioversion is either totally unsuccessful, or the AF returns within seconds to hours of normal sinus rhythm having been restored. Furthermore, cardioversion carries risks to the patient. Regardless of whether the cardioversion is performed pharmacologically or electrically, anticoagulation medications should ordinarily be taken for three weeks before the cardioversion, in order to prevent thromboembolic complications [A. J. CAMM et al. Guidelines for the management of atrial fibrillation: the Task Force for the Management of Atrial Fibrillation of the European Society of Cardiology (ESC). European Heart Journal 31 (2010):2369-2439].

An implanted atrial defibrillator may also be used to electrically cardiovert a patient who is experiencing AF. The energy required to do so is considerably less than the energy needed for transthoracic electric cardioversion. However, the internal shocks are quite painful, and because such internal shocks can precipitate ventricular fibrillation, atrial defibrillators are currently only built into conventional implantable cardioverter-defibrillator (ICDs) for patients at risk of sudden cardiac death due to ventricular fibrillation and/or tachycardia.

Additional methods for terminating the AF are also available [Ole-Gunnar ANFINSEN. Non-pharmacological Treatment of Atrial Fibrillation. Indian Pacing Electrophysiol J 2(1, 2002): 4-14]. One method is radiofrequency catheter ablation of the atrioventricular node followed by implantation of a pacemaker. Electrical pacing may also be useful for the prevention or termination of AF, especially in patients with bradycardia [B P KNIGHT et al. Role of permanent pacing to prevent atrial fibrillation. Circulation 111(2, 2005):240-3]. Another method is radiofrequency catheter ablation of localized sources (ectopic foci or localized reentrant circuits) that may be responsible for the AF. Such ablation strategies include: circumferential pulmonary vein isolation; pulmonary vein isolation followed by extensive ablation at many sites within the atria; and electrogram-guided ablation in which potential sources of AF are identified by electrode mapping before ablation [ATIENZA F, Almendral J, Jalife J, Zlochiver S, Ploutz-Snyder R, Torrecilla E G, Arenal A, Kalifa J, Fernandez-Aviles F, Berenfeld O. Real-time dominant frequency mapping and ablation of dominant frequency sites in atrial fibrillation with left-to-right frequency gradients predicts long-term maintenance of sinus rhythm. Heart Rhythm 6(1, 2009):33-40]. Treatment by localized ablation is not possible if the sources are not themselves localized, but AF resulting from multiple nonlocalized sources might be treated by the placement of multiple surgical lesions in the atrium, to compartmentalize the atria into regions that cannot support the propagation of multiple wavelets [GILLINOV A M, Saltman A E. Surgical approaches for atrial fibrillation. Med Clin North Am 92(1, 2008):203-15]. Surgical ablation methods are ordinarily not performed as stand-alone operations, but are instead performed in conjunction with surgery for coronary artery bypass or valve repair/replacement. A related surgical procedure is the excision or closure of the left atrial appendage, in order to prevent arterial thrombi from forming.

Because of the risks and expense associated with such catheter or surgical ablation methods, they are usually not attempted unless attempts are first made to control the patient's high heart rate, without necessarily converting the AF to normal sinus rhythm. The potential benefit of maintaining sinus rhythm with anti-arrhythmic drugs is negated by potential adverse effects of those drugs, including increased mortality. Therefore, a strategy that attempts only to control the high heart rate of AF patients may be preferable to a rhythm-control strategy or a combined rhythm/rate control strategy, especially in asymptomatic patients or in patients for whom previous cardioversion only temporarily terminated the AF.

Partial denervation of the vagus or other autonomic nerves has sometimes been used to treat AF, which is ordinarily done only in conjunction with ablation to circumferentially isolate the pulmonary vein [CHOU C C, Chen P S. New concepts in atrial fibrillation: neural mechanisms and calcium dynamics. Cardiol Clin 27(1, 2009):35-43]. TAN and colleagues suggest that ablation of extracardiac autonomic nerves may be an effective alternative to ablation of intracardiac autonomic nerves for the treatment of AF. They found that decentralization, rather than denervation, is the anti-arrhythmic mechanism of stellate ganglion and vagus nerve denervation [TAN A Y, Zhou S, Ogawa M, Song J, Chu M, Li H, Fishbein M C, Lin S F, Chen L S, Chen P S. Neural mechanisms of paroxysmal atrial fibrillation and paroxysmal atrial tachycardia in ambulatory canines. Circulation 118(9, 2008):916-25].

Electrical stimulation of the vagus nerve has also been proposed as another treatment for atrial fibrillation, which would have an advantage over vagus denervation in that effects of stimulation would generally not be irreversible. However, vagus nerve stimulation has been attempted only invasively in animal experiments. At one time, electrical stimulation of the vagus nerve (especially the right vagus nerve) was considered to invariably exacerbate rather than ameliorate the dangers of AF. In fact, electrical stimulation of a vagus nerve has long been used to induce and maintain AF. For example, bilateral vagus nerve stimulation at 20 Hz, at a level sufficient to induce a 50% decrease in sinus heart rate, increases inducibility of AF, an effect that is blocked by ablation of ganglionated plexi of the intrinsic cardiac autonomic nervous system [LU Z, Cui B, He B, Hu X, Wu W, Huang C, Jiang H. Effects of autonomic interventions on atrial restitution properties. J Cardiovasc Electrophysiol 22(1, 2011):84-90]. In a rabbit model, right vagus nerve stimulated at 20 Hz, 0.2 ms, 150-200 microamp, at a level sufficient to produce a sinus rhythm heart rate reduction rate of 50%, induces atrial fibrillation [OLIVEIRA M, da Silva M N, Geraldes V, Xavier R, Laranjo S, Silva V, Postolache G, Ferreira R, Rocha I. Acute vagal modulation of electrophysiology of the atrial and pulmonary veins increases vulnerability to atrial fibrillation. Exp Physiol 96(2, 2011):125-33]. SIH et al. induced non-sustained AF by vagus nerve stimulation with two sets of parameters: stimulation sufficient to cause a 10 to 20 percent reduction in sinus rate (bipolar square pulses at 6-8 Hz, 10 V, 4 millisecond pulses), and stimulation sufficient to cause 5 seconds of asystole (10-15 Hz, 12 V, 4 millisecond pulses). The two sets of stimulation parameters resulted in atrial fibrillation frequencies of 7.8 and 10.1, respectively, with the former waveforms being more organized, as indicated by the mean square error in a linear prediction algorithm [SIH H J, Zipes D P, Berbari E J, Olgin J E. A high-temporal resolution algorithm for quantifying organization during atrial fibrillation. IEEE Trans Biomed Eng 46(4, 1999):440-50].

Nevertheless, it is now thought that vagal nerve stimulation (VNS) might also be protective against AF, provided that parameters of the nerve stimulation are properly selected [ZHANG Y, Mazgalev T N. Arrhythmias and vagus nerve stimulation. Heart Fail Rev 16(2, 2011):147-61]. Although treatment of AF with VNS has not been attempted in humans, there is reason to believe that it is feasible. For example, VNS has been used to treat epilepsy and depression in many patients, without producing AF, except for one case of transient AF that may have been due to temporary injury to the vagus nerve during surgical implantation [SRINIVASAN B, Awasthi A. Transient atrial fibrillation after the implantation of a vagus nerve stimulator. Epilepsia 45(12, 2004):1645; SPUCK S, Tronnier V, Orosz I, Schonweiler R, Sepehrnia A, Nowak G, Sperner J. Operative and technical complications of vagus nerve stimulator implantation. Neurosurgery 67(2 Suppl Operative, 2010):489-94].

It may well be that the stimulation parameters that are typically used in therapeutic VNS for conditions such as epilepsy are not suitable for the induction of AF, and/or that because VNS is ordinarily performed on the left vagus nerve, induction of AF is not likely. Invasive vagal nerve stimulation typically uses square wave pulse signals. The typical waveform parameter values for VNS therapy for epilepsy and depression are: a current between 1 and 2 mA, a frequency of between 20 and 30 Hz, a pulse width of 250-500 microseconds, and a duty cycle of 10% (signal ON time of 30 s, and a signal OFF time to 5 min). Output current is gradually increased from 0.25 mA to the maximum tolerable level (maximum, 3.5 mA), with typical therapeutic settings ranging from 1.0 to 1.5 mA. Greater output current is associated with increased side effects, including voice alteration, cough, a feeling of throat tightening, and dyspnea. Frequency is typically 20 Hz in depression and 30 Hz in epilepsy. The therapy is adjusted in a gradual, systematic fashion to individualize therapy for each patient. To treat migraine headaches, typical VNS parameters are a current of 0.25 to 1 mA, a frequency of 30 Hz, a pulse width of 500 microseconds, and an 'ON' time of 30 s every 5 min. To treat migraine plus epilepsy, typical parameters are 1.75 mA, a frequency of 20 Hz, a pulse width of 250 microseconds, and 'ON' time of 7 s followed by an 'OFF' time of 12 s. To treat mild to moderate Alzheimer's disease, typical VNS waveform parameters are: a current of 0.25 to 0.5 mA, a frequency of 20 Hz, a pulse width of 500 microseconds, and an 'ON' time of 30 s every 5 min [ANDREWS, A. J., 2003. Neuromodulation. I. Techniques-deep brain stimulation, vagus nerve stimulation, and transcranial magnetic stimulation. Ann. N.Y. Acad. Sci. 993, 1-13; LABINER, D. M., Ahern, G. L., 2007. Vagus nerve stimulation therapy in depression and epilepsy: therapeutic parameter settings. Acta. Neurol. Scand. 115, 23-33; G. C. ALBERT, C. M. Cook, F. S. Prato, A. W. Thomas. Deep brain stimulation, vagus nerve stimulation and transcranial stimulation: An overview of stimulation parameters and neurotransmitter release. Neuroscience and Biobehavioral Reviews 33 (2009) 1042-1060]. However, if a patient in whom a vagus nerve stimulator had already been implanted did develop AF, and if the AF terminated after the stimulation parameters were changed, it would not be clear whether the termination was due to the absence of previous parameters that promoted AF, or to the presence of new parameters that inhibit AF.

Information suggesting the potentially protective effect of vagal nerve stimulation on AF has come from animal experiments involving invasive stimulation, as described below, most of which used dog models. In that regard, it should be noted that the vagus nerves of dogs have a different anatomy than that of humans. Depending on species, sympathetic fibers may run an early course together with vagal fibers, as in the cat and dog (i.e., the vagosympathetic trunk) or be separate as in rabbit and humans. The vagosympathetic trunk runs along the dorsal border of the common carotid artery and is formed by the convergence caudal to the cranial cervical ganglion of the vagus and sympathetic nerves. These nerve cords lose their association only before reaching the thoracic inlet, where they separate. Therefore, unless the vagus nerve is surgically isolated within the vagosympathetic trunk of the dog, is conceivable that results obtained by stimulating the vagosympathetic trunk of the dog may be attributable in part to co-stimulation of sympathetic nerves. Nevertheless, the following publications suggest that low-level stimulation of the vagus nerve may be protective against AF.

ZHANG et al. reported that the arrhythmogenic effect of VNS is intensity dependent and requires a threshold to be manifest. Using 20 Hz, pulse width 0.2 ms, square pulses, they found that moderate VNS producing less than a 40% reduction of sinus cycle length has no effect on AF inducibility [ZHANG Y, Ilsar I, Sabbah H N, Ben David T, Mazgalev T N. Relationship between right cervical vagus nerve stimulation and atrial fibrillation inducibility: therapeutic intensities do not increase arrhythmogenesis. Heart Rhythm 6(2, 2009):244-50].

LI et al. performed VNS by applying 20 Hz, 0.1-ms duration, square wave pulses for 3 hours to both vagosympathetic trunks in dogs. One volt lower than the threshold of VNS required to lower the sinus rate was defined to be low-level VNS. At this low level, VNS caused an increase in the threshold of high frequency stimulation needed to induce AF, which was said to be not dependent on the activation of afferent vagal nerve fibers that project to the brain. They interpret their findings as indicating complex interactions between the extrinsic and intrinsic cardiac autonomic nervous system [LI S, Scherlag B J, Yu L, Sheng X, Zhang Y, Ali R, Dong Y, Ghias M, Po S S. Low-level vagosympathetic stimulation: a paradox and potential new modality for the treatment of focal atrial fibrillation. Circ Arrhythm Electrophysiol 2(6, 2009):645-51].

SHA et al. performed similar stimulation experiments with 20 Hz, 0.1-ms duration, square wave pulses, except that only the right vagus nerve was stimulated, and low level VNS was defined to be 50% of voltage needed to lower the sinus rate. Their results were similar to the above-mentioned results of LI et al. In addition, sinus rate slowing or acceleration that could be induced by stimulation of the superior left ganglionated plexi and right stellate ganglion, respectively, were inhibited by the vagal stimulation. They interpret the results as indicating that VNS suppresses both sympathetic and parasympathetic components of the intrinsic cardiac autonomic nervous system [SHA Y, Scherlag B J, Yu L, Sheng X, Jackman W M, Lazzara R, Po S S. Low-Level Right Vagal Stimulation: Anticholinergic and Antiadrenergic Effects. J Cardiovasc Electrophysiol 22(10, 2011):1147-53].

SHENG et al applied low-level 20 Hz, 0.1-ms duration, square wave pulses to both vagosympathetic trunks in dogs and found that the stimulation can prevent or reverse remodeling of the heart that is due to experimentally induced AF. They attributed these observations to the inhibition of the intrinsic cardiac autonomic nervous system by VNS [SHENG X, Scherlag B J, Yu L, Li S, Ali R, Zhang Y, Fu G, Nakagawa H, Jackman W M, Lazzara R, Po S S. Prevention and reversal of atrial fibrillation inducibility and autonomic remodeling by low-level vagosympathetic nerve stimulation. J Am Coll Cardiol 57(5, 2011):563-71].

YU et al applied low-level 20 Hz, 0.1-ms duration, square wave pulses to both vagosympathetic trunks in dogs, and by recording electrical signals from cardiac ganglia, they found that the stimulation inhibits the intrinsic cardiac autonomic nervous system [YU L, Scherlag B J, Li S, Sheng X, Lu Z, Nakagawa H, Zhang Y, Jackman W M, Lazzara R, Jiang H, Po S S. Low-level vagosympathetic nerve stimulation inhibits atrial fibrillation inducibility: direct evidence by neural recordings from intrinsic cardiac Ganglia. J Cardiovasc Electrophysiol 22(4, 2011):455-63].

Applicant is not aware of any patent or patent application that disclosed or suggested the use of noninvasive nerve stimulation for the treatment or prevention of atrial fibrillation or its sequelae. The only related patents or applications are those dealing with the use of an implanted electrode or other invasive technique, for example, the following patents. U.S. Pat. No. 6,668,191, entitled Apparatus and method for electrical stimulation adjunct (add-on) therapy of atrial fibrillation, inappropriate sinus tachycardia, and refractory hypertension with an external stimulator, to BOVEJA, discloses a method of atrial fibrillation therapy involving neuromodulation of the vagus nerve using an implantable lead-receiver. Exemplary stimulator parameters are 1.0 mA current output, 0.2 msec pulse width, 15 Hz frequency, 15 sec on-time, 1.0 min off-time, in repeating cycles. U.S. Pat. No. 7,321,793, entitled Vagal stimulation for atrial fibrillation therapy, to BEN-EZRA et al, discloses the maintenance of atrial fibrillation (prevention of the return to normal sinus rhythm) using an electrode device, which is applied to a portion of a vagus nerve that innervates the heart of the patient, specifically "an electrode device, adapted to be coupled to a vagus nerve of the subject." The treatment methods contemplate stimulating action potentials in some nerve fibers and inhibiting action potentials in others. Exemplary signal parameters to maintain spontaneous AF for at least about 24 hours include an amplitude of about 3 milliamps, a pulse width of about 1 millisecond, and a frequency of about 5 Hz. Patent application publication US20050131467, entitled Method and apparatus for electrical stimulation therapy for at least one of atrial fibrillation, congestive heart failure, inappropriate sinus tachycardia, and refractory hypertension, to BOVEJA, discloses vagal nerve stimulation for the treatment of atrial fibrillation using a method using implantable components. Exemplary stimulus parameters are—current output: 0.75 milliAmps; Pulse width: 0.20 msec; Pulse frequency: 20 Hz; Cycles: 20 sec. on-time and 2.0 min. off-time in repeating cycles. Patent application publication US20080091241, entitled Vagal stimulation for cardioversion of atrial fibrillation, to BEN-EZRA et al, discloses apparatus for treating a subject suffering from spontaneous atrial fibrillation that includes an electrode device adapted to be coupled to a site of the subject selected from the list consisting of: a vagus nerve of the subject, an epicardial fat pad of the subject, a pulmonary vein of the subject, etc. Exemplary stimulation parameters to prevent the return to normal sinus rhythm are an amplitude of about 3 milliamps, a pulse width of about 1 millisecond, and a frequency of about 5 Hz. U.S. Pat. No. 8,060,197, entitled Parasympathetic stimulation for termination of non-sinus atrial tachycardia, to BEN-DAVID et al, describes methods for treating a patient with atrial fibrillation that includes an electrode device, configured to be coupled to a baroreceptor site of a subject. Exemplary stimulus parameters are a duration of between about 2 and about 5 seconds, a frequency of between about 50 and about 100 Hz and/or between about 50 and about 200 pulses per second, and/or an amplitude of between about 5 and about 30 mA, e.g., about 10 mA.

Applicant is also unaware of any patent or patent application that disclosed or suggested the use of noninvasive nerve stimulation for the prevention of atrial fibrillation. The only relevant patents or applications are those related to the use of an implanted electrode or other invasive technique, for example, the following. U.S. Pat. No. 5,522,854, entitled Method and apparatus for the prevention of arrhythmia by nerve stimulation to prevent arrhythmia, to IDEKER et al., discloses an implantable apparatus wherein risk of ventricular tachycardia is based on the ratio of sympathetic nerve activity to parasympathetic nerve activity, and nerves including a vagus nerve may be stimulated. Patent application number US20070179543, entitled Techniques for prevention of atrial fibrillation, to BEN-DAVID et al, and U.S. Pat. No. 8,005,545 Parasympathetic stimulation for prevention and treatment of atrial fibrillation, to BEN-DAVID et al, disclose methods of reducing a risk of an occurrence of an episode of the atrial fibrillation by applying an electrical current to a site of the subject containing parasympathetic nervous tissue, such as a vagus nerve, an epicardial fat pad, a sinoatrial (SA) node fat pad, an atrioventricular (AV) node fat pad, etc. The methods involve the invasive application of at least one electrode device to such a site of the subject. Timing of the stimulation is, for example, a pulse initiated at about 100 milliseconds after an R-wave, with pulse duration of between about 100 microseconds and about 2.5 milliseconds, e.g., about 1 millisecond, with pulse amplitude of between about 0.1 and about 9 mA, e.g., about 2.5 mA. U.S. Pat. No. 5,578,061, entitled Method and apparatus for cardiac therapy by stimulation of a physiological representative of the parasympathetic nervous system, to STROETMANN et al. discloses invasive methods for treating impending or imminent tachycardia by vagal nerve stimulation, but makes no mention of atrial fibrillation. U.S. Pat. No. 5,658,318, entitled Method and apparatus for detecting a state of imminent cardiac arrhythmia in response to a nerve signal from the autonomic nerve system to the heart, and for administrating anti-arrhythmia therapy in response thereto, to STROETMANN et al, discloses invasive methods to detect imminent arrhythmia using a sensor that directly senses activity in a nerve, wherein the sensor is in direct contact with the nerve. The nerve may be a vagus nerve, which may also be stimulated by the device. The patent makes no mention of atrial fibrillation.

Applicant is also unaware of any patent or patent application that disclosed or suggested the use of noninvasive nerve stimulation for preventing atrial fibrillation sequelae, such as strokes caused by emboli. The only relevant patents or applications are those related to the use of an implanted electrode or other invasive technique, for example, the following. U.S. Pat. No. 7,885,711, entitled Vagal stimulation for anti-embolic therapy, to BEN-EZRA, discloses applying an electrical current to a vagus nerve of a subject suffering from spontaneous atrial fibrillation, comprising an electrode device, adapted to be coupled to a nerve of a subject. U.S. Pat. No. 8,005,542, entitled Therapeutic maintenance of atrial fibrillation by electrical stimulation, to BEN-DAVID et al, discloses applying an electrical current to a vagus nerve of a subject suffering from spontaneous atrial fibrillation, involving at least one electrode device which is applied to a vagus nerve. Patent application US20080125825, entitled Therapeutic maintenance of atrial fibrillation by electrical stimulation, to BEN-EZRA et al, discloses an electrode device, adapted to be coupled to tissue of the subject, configured to maintain spontaneous AF for at least about 24 hours, so as to treat the subject by modifying blood flow to reduce the risk of thromboembolic events. The electrode is said to be placed: (a) around vagus nerve, (b) around vagus nerve and the carotid artery or (c) inside the carotid artery in a position suitable for vagal stimulation. Patent application US20080091245, entitled Combined parasympathetic stimulation and cardiac pacing, to BEN-EZRA et al, discloses an electrode device, coupled to tissue selected from the group consisting of: a vagus nerve, an epicardial fat pad, and atrial tissue, etc. of a subject suffering from spontaneous atrial fibrillation. The device is configured to maintain spontaneous AF for at least about 24 hours, so as to modify blood flow within the atria and reduce risk of thromboembolic events.

The present invention addresses a significant impediment to the development of the above-mentioned animal experiment observations into useful AF treatment for humans. That impediment is the unavailability of a non-invasive nerve stimulator that produces little or no pain and that does not generate unwanted side effects, but nevertheless can stimulate the vagus nerve to achieve therapeutic results. The availability of such a noninvasive stimulator will increase the number and types of individuals with whom vagal nerve stimulation might be undertaken as a potential treatment for AF, as described in the introductory section of this application. The paragraphs that follow disclose such noninvasive stimulation devices. After the devices are described, their use to treat and/or avert atrial fibrillation will be disclosed.

Transcutaneous electrical stimulation with electrodes, as well as with magnetic stimulators, can be unpleasant or painful, in the experience of patients that undergo such procedures. The quality of sensation caused by stimulation depends strongly on current and frequency, such that currents barely greater than the perception threshold generally cause painless sensations described as tingle, itch, vibration, buzz, touch, pressure, or pinch, but higher currents can cause sharp or burning pain. As the depth of penetration of the stimulus under the skin is increased, any pain will generally begin or increase. Strategies to reduce the pain include: use of anesthetics placed on or injected into the skin near the stimulation and placement of foam pads on the skin at the site of stimulation [Jeffrey J. BORCKARDT, Arthur R. Smith, Kelby Hutcheson, Kevin Johnson, Ziad Nahas, Berry Anderson, M. Bret Schneider, Scott T. Reeves, and Mark S. George. Reducing Pain and Unpleasantness During Repetitive Transcranial Magnetic Stimulation. Journal of ECT 2006; 22:259-264], use of nerve blockades [V. HAKKINEN, H. Eskola, A. Yli-Hankala, T. Nurmikko and S. Kolehmainen. Which structures are sensitive to painful transcranial stimulation? Electromyogr. clin. Neurophysiol. 1995, 35:377-383], the use of very short stimulation pulses [V. SUIHKO. Modelling the response of scalp sensory receptors to transcranial electrical stimulation. Med. Biol. Eng. Comput., 2002, 40, 395-401], decreasing current density by increasing electrode size [Kristof VERHOEVEN and J. Gert van Dijk. Decreasing pain in electrical nerve stimulation. Clinical Neurophysiology 117 (2006) 972-978], using a high impedance electrode [N. SHA, L. P. J. Kenney, B. W. Heller, A. T. Barker, D. Howard and W. Wang. The effect of the impedance of a thin hydrogel electrode on sensation during functional electrical stimulation. Medical Engineering & Physics 30 (2008): 739-746] and providing patients with the amount of information that suits their personalities [Anthony DELITTO, Michael J Strube, Arthur D Shulman, Scott D Minor. A Study of Discomfort with Electrical Stimulation. Phys. Ther. 1992; 72:410-424]. U.S. Pat. No. 7,614,996, entitled Reducing discomfort caused by electrical stimulation, to RIEHL discloses the application of a secondary stimulus to counteract what would otherwise be an uncomfortable primary stimulus. Other methods of reducing pain are intended to be used with invasive nerve stimulation [U.S. Pat. No. 7,904,176, entitled Techniques for reducing pain associated with nerve stimulation, to BEN-EZRA et al].

Additional considerations related to pain resulting from the stimulation are as follows. When stimulation is repeated over the course of multiple sessions, patients may adapt to the pain and exhibit progressively less discomfort. Patients may be heterogeneous with respect to their threshold for pain caused by stimulation, including heterogeneity related to gender and age. Electrical properties of an individual's skin vary from day to day and may be affected by cleaning, abrasion, and the application of various electrode gels and pastes. Skin properties may also be affected by the stimulation itself, as a function of the duration of stimulation, the recovery time between stimulation sessions, the transdermal voltage, the current density, and the power density. The application of multiple electrical pulses can result in different perception or pain thresholds and levels of sensation, depending on the spacing and rate at which pulses are applied. The separation distance between two electrodes determines whether sensations from the electrodes are separate, overlap, or merge. The limit for tolerable sensation is sometimes said to correspond to a current density of 0.5 $mA/cm^2$, but in reality the functional relationship between pain and current density is very complicated. Maximum local current density may be more important in producing pain than average current density, and local current density generally varies under an electrode, e.g., with greater current densities along edges of the electrode or at "hot spots." Furthermore, pain thresholds can have a thermal and/or electrochemical component, as well as a current density component. Pulse frequency plays a significant role in the perception of pain, with muscle contraction being involved at some frequencies and not others, and with the spatial extent of the pain sensation also being a function of frequency. The sensation is also a function of the waveform (square-wave, sinusoidal, trapezoidal, etc.), especially if pulses are less than a millisecond in duration [Mark R. PRAUSNITZ. The effects of electric current applied to skin: A review for transdermal drug delivery. Advanced Drug Delivery Reviews 18 (1996): 395-425].

Considering that there are so many variables that may influence the likelihood of pain during non-invasive electrical stimulation (detailed stimulus waveform, frequency, current density, electrode type and geometry, skin preparation, etc.), considering that these same variables must be simultaneously selected in order to independently produce a desired therapeutic outcome by nerve stimulation, and considering that one also wishes to selectively stimulate the nerve (e.g., avoid stimulating a nearby nerve), it is understandable that prior to the present disclosure, no one has described devices and methods for stimulating a nerve electrically, totally non-invasively, selectively, and without causing substantial pain.

Applicant discovered the disclosed electrode-based devices and methods in the course of experimentation with a magnetic stimulation device that was disclosed in Applicant's commonly assigned co-pending U.S. patent application Ser. No. 12/964,050, entitled Magnetic Stimulation Devices and Methods of Therapy, to SIMON et al. Thus, combined elements in the electrode-based invention do not merely perform the function that the elements perform separately (viz., perform therapeutic electrical stimulation or neuromodulation, minimize stimulation pain, or stimulate the nerve selectively), and one of ordinary skill in the art would not have combined the claimed elements by known methods because the archetypal magnetic stimulator was known only to Applicant. That stimulator used a magnetic coil, embedded in a safe and practical conducting medium that was in direct contact with arbitrarily-oriented skin of a patient, which had not been described in its closest art [Rafael CARBUNARU and Dominique M. Durand. Toroidal coil models for transcutaneous magnetic stimulation of nerves. IEEE Transactions on Biomedical Engineering 48 (4, 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999. (UMI Microform Number: 9940153, UMI Company, Ann Arbor Mich.)]. Existing magnetic stimulators are complex and expensive, use high currents that overheat and limit the possible duration of stimulation, and can produce stimulation pain. In contrast to existing magnetic stimulators, the stimulator that was disclosed in Applicant's above-cited co-pending patent application is relatively simple to construct and operates with low currents. Furthermore, the device confines the magnetic field to within the device itself, so that magnetic fields do not enter the patient's body. As a result, this design makes it possible to stimulate the patient's nerve over an extended period of time selectively and without producing pain.

FIG. 1A is a schematic diagram of Applicant's above-mentioned magnetic nerve stimulating/modulating device 301 for delivering impulses of energy to nerves for the treatment of medical conditions. As shown, device 301 may include an impulse generator 310; a power source 320 coupled to the impulse generator 310; a control unit 330 in communication with the impulse generator 310 and coupled to the power source 320; and a magnetic stimulator coil 341 coupled via wires to impulse generator coil 310. The stimulator coil 341 is toroidal in shape, due to its winding around a toroid of core material.

Although the magnetic stimulator coil 341 is shown in FIG. 1A to be a single coil, in practice the coil may also comprise two or more distinct coils, each of which is connected in series or in parallel to the impulse generator 310. Thus, the coil 341 that is shown in FIG. 1A represents all the magnetic stimulator coils of the device collectively. In a preferred embodiment that is discussed in connection with FIG. 5D below, coil 341 actually contains two coils that may be connected either in series or in parallel to the impulse generator 310.

The item labeled in FIG. 1A as 351 is a volume, surrounding the coil 341, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 351 corresponds also to sinuousness or curvature on the surface of the body, against which the conducting medium 351 is applied, so as to make the medium and body surface contiguous. As time-varying electrical current is passed through the coil 341, a magnetic field is produced, but because the coil winding is toroidal, the magnetic field is spatially restricted to the interior of the toroid. An electric field and eddy currents are also produced. The electric field extends beyond the toroidal space and into the patient's body, causing electrical currents and stimulation within the patient. The volume 351 is electrically connected to the patient at a target skin surface in order to significantly reduce the current passed through the coil 341 that is needed to accomplish stimulation of the patient's nerve or tissue. In a preferred embodiment of the magnetic stimulator that is discussed below in connection with FIG. 5D, the conducting medium with which the coil 341 is in contact need not completely surround the toroid.

The design of the magnetic stimulator 301, which is adapted herein for use with surface electrodes, makes it possible to shape the electric field that is used to selectively stimulate a relatively deep nerve such as a vagus nerve in the patient's neck. Furthermore, the design produces significantly less pain or discomfort (if any) to a patient than stimulator devices that are currently known in the art. Conversely, for a given amount of pain or discomfort on the part of the patient (e.g., the threshold at which such discomfort or pain begins), the design achieves a greater depth of penetration of the stimulus under the skin.

Figure 1B:
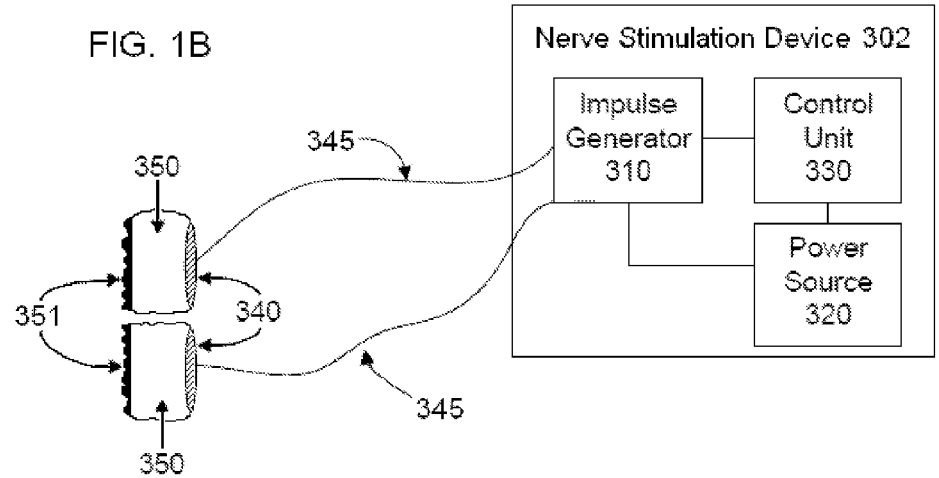
FIG. 1B is a schematic view of a nerve modulating device according to the present invention which supplies controlled pulses of electrical current to surface electrodes.

FIG. 1B is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either the magnetic stimulator 301 or the electrode-based stimulator 302, allowing the user to change parameter settings depending on whether coils 341 or the electrodes 340 are attached.

Although a pair of electrodes 340 is shown in FIG. 1B, in practice the electrodes may also comprise three or more distinct electrode elements, each of which is connected in series or in parallel to the impulse generator 310. Thus, the electrodes 340 that are shown in FIG. 1B represent all electrodes of the device collectively.

The item labeled in FIG. 1B as 350 is a volume, contiguous with an electrode 340, that is filled with electrically conducting medium. As described below in connection with embodiments of the invention, conducting medium in which the electrode 340 is embedded need not completely surround an electrode. As also described below in connection with a preferred embodiment, the volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's coils or electrodes. The signals are selected to be suitable for amelioration of a particular medical condition, when the signals are applied non-invasively to a target nerve or tissue via the coil 341 or electrodes 340. It is noted that nerve stimulating/modulating device 301 or 302 may be referred to by its function as a pulse generator. Patent application publications US20050075701 and US20050075702, both to SHAFER, both of which are incorporated herein by reference, relating to stimulation of neurons of the sympathetic nervous system to attenuate an immune response, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard and computer mouse as well as any externally supplied physiological signals (see FIG. 9), analog-to-digital converters for digitizing externally supplied analog signals (see FIG. 9), communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes or coils, as well as the spatial distribution of the electric field that is produced by the electrodes or coils. The rise time and peak energy are governed by the electrical characteristics of the stimulator and electrodes or coils, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurto, Przemystaw Ptonecki, Jacek Starzynski, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, 105 Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

FIG. 2A illustrates an exemplary electrical voltage/current profile for a stimulating, blocking and/or modulating impulses applied to a portion or portions of selected nerves in accordance with an embodiment of the present invention. For the preferred embodiment, the voltage and current refer to those that are non-invasively produced within the patient by the stimulator coils or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the coil 341 or electrodes 340 that deliver the stimulating, blocking and/or modulating impulse 410 to the nerve. Nerve stimulating/modulating device 301 or 302 may be externally powered and/or recharged or may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulses to the electrodes or coils, the device disclosed in patent publication No. US20050216062, entitled Multi-functional electrical stimulation system, to HERBST, may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type the user wishes, who can then observe the effect of this signal on a substance being treated.

The stimulating, blocking and/or modulating impulse signal 410 preferably has a frequency, an amplitude, a duty cycle, a pulse width, a pulse shape, etc. selected to influence the therapeutic result, namely, stimulating, blocking and/or modulating some or all of the transmission of the selected nerve. For example, the frequency may be about 1 Hz or greater, such as between about 15 Hz to 50 Hz, more preferably around 25 Hz. The modulation signal may have a pulse width selected to influence the therapeutic result, such as about 20 microseconds or greater, such as about 20 microseconds to about 1000 microseconds. For example, the electric field induced by the device within tissue in the vicinity of a nerve is 10 to 600 V/m, preferably around 300 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz.

An objective of the disclosed stimulators is to provide both nerve fiber selectivity and spatial selectivity. Spatial selectivity may be achieved in part through the design of the electrode or coil configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J. Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder; U.S. Pat. No. 7,778,703, entitled Selective nerve fiber stimulation for treating heart conditions, to Gross et al]. However, bursts of sinusoidal pulses are a preferred stimulation waveform, as shown in FIGS. 2B and 2C. As seen there, individual sinusoidal pulses have a period of $\tau$, and a burst consists of N such pulses. This is followed by a period with no signal (the inter-burst period). The pattern of a burst followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds (a much smaller value of T is shown in FIG. 2C to make the bursts discernable). When these exemplary values are used for T and $\tau$, the waveform contains significant Fourier components at higher frequencies (1/200 microseconds=5000/sec), as compared with those contained in transcutaneous nerve stimulation waveforms, as currently practiced.

Applicant is unaware of such a waveform having been used with therapeutic nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters $\tau$, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10 (1989):187-191; Alex R WARD, Nataliya Shkuratova. Russian Electrical Stimulation The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008):1167-1176; Alex R WARD. Electrical Stimulation Using Kilohertz-Frequency Alternating Current. Physical Therapy 89 (2, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2B and 2C may have an $E_{max}$ value of 17 V/m, which is sufficient to stimulate the nerve but is significantly lower than the threshold needed to stimulate surrounding muscle.

A preferred embodiment of the electrode-based stimulator is shown in FIG. 3A. A cross-sectional view of the stimulator along its long axis is shown in FIG. 3B. As shown, the stimulator (30) comprises two heads (31) and a body (32) that joins them. Each head (31) contains a stimulating electrode. The body of the stimulator (32) contains the electronic components and battery (not shown) that are used to generate the signals that drive the electrodes, which are located behind the insulating board (33) that is shown in FIG. 3B. However, in other embodiments of the invention, the electronic components that generate the signals that are applied to the electrodes may be separate, but connected to the electrode head (31) using wires. Furthermore, other embodiments of the invention may contain a single such head or more than two heads.

Heads of the stimulator (31) are applied to a surface of the patient's body, during which time the stimulator may be held in place by straps or frames (not shown), or the stimulator may be held against the patient's body by hand. In either case, the level of stimulation power may be adjusted with a wheel (34) that also serves as an on/off switch. A light (35) is illuminated when power is being supplied to the stimulator. An optional cap may be provided to cover each of the stimulator heads (31), to protect the device when not in use, to avoid accidental stimulation, and to prevent material within the head from leaking or drying. Thus, in this embodiment of the invention, mechanical and electronic components of the stimulator (impulse generator, control unit, and power source) are compact, portable, and simple to operate.

Construction of different embodiments of the stimulator head is shown in more detail in FIG. 4. Referring now to the exploded view shown in FIG. 4A, the electrode head is assembled from a snap-on cap (41) that serves as a tambour for a dielectric or conducting membrane (42), a disc without fenestration (43) or alternatively with fenestration (43'), the head-cup (44), and the electrode which is also a screw (45). Two embodiments of the disc (43) are shown. The preferred embodiment (43) is a solid, ordinarily uniformly conducting disc (e.g., metal such as stainless steel), which is possibly flexible in some embodiments. An alternate embodiment of the disc (43') is also shown, which is a non-conducting (e.g., plastic) aperture screen that permits electrical current to pass through its apertures. The electrode (45, also 340 in FIG. 1) seen in each stimulator head has the shape of a screw that is flattened on its tip. Pointing of the tip would make the electrode more of a point source, such that equations for the electrical potential may have a solution corresponding more closely to a far-field approximation. Rounding of the electrode surface or making the surface with another shape will likewise affect the boundary conditions. Completed assembly of the stimulator head is shown in FIG. 4B, which also shows how the head is attached to the body of the stimulator (47).

The membrane (42) ordinarily serves as the interface shown as 351 in FIG. 1. For example, the membrane (42) may be made of a dielectric (non-conducting) material, such as a thin sheet of Mylar (biaxially-oriented polyethylene terephthalate, also known as BoPET). In other embodiments, it may be made of conducting material, such as a sheet of Tecophilic material from Lubrizol Corporation, 29400 Lakeland Boulevard, Wickliffe, Ohio 44092. In one embodiment shown in FIG. 4A, apertures of the alternate disc (43') may be open, or they may be plugged with conducting material, for example, KM10T hydrogel from Katecho Inc., 4020 Gannett Ave., Des Moines Iowa 50321. If the apertures are so-plugged, and the membrane (42) is made of conducting material, the membrane becomes optional, and the plug serves as the interface 351 shown in FIG. 1.

The head-cup (44) is filled with conducting material (350 in FIG. 1), for example, SIGNAGEL Electrode Gel from Parker Laboratories, Inc., 286 Eldridge Rd., Fairfield N.J. 07004. The snap-on cap (41), aperture screen disc (43'), head-cup (44) and body of the stimulator are made of a non-conducting material, such as acrylonitrile butadiene styrene. The depth of the head-cup from its top surface to the electrode may be between one and six centimeters. The head-cup may have a different curvature than what is shown in FIG. 4, or it may be tubular or conical or have some other inner surface geometry that will affect the Neumann boundary conditions of the corresponding electrical field equations.

Figure 4A:
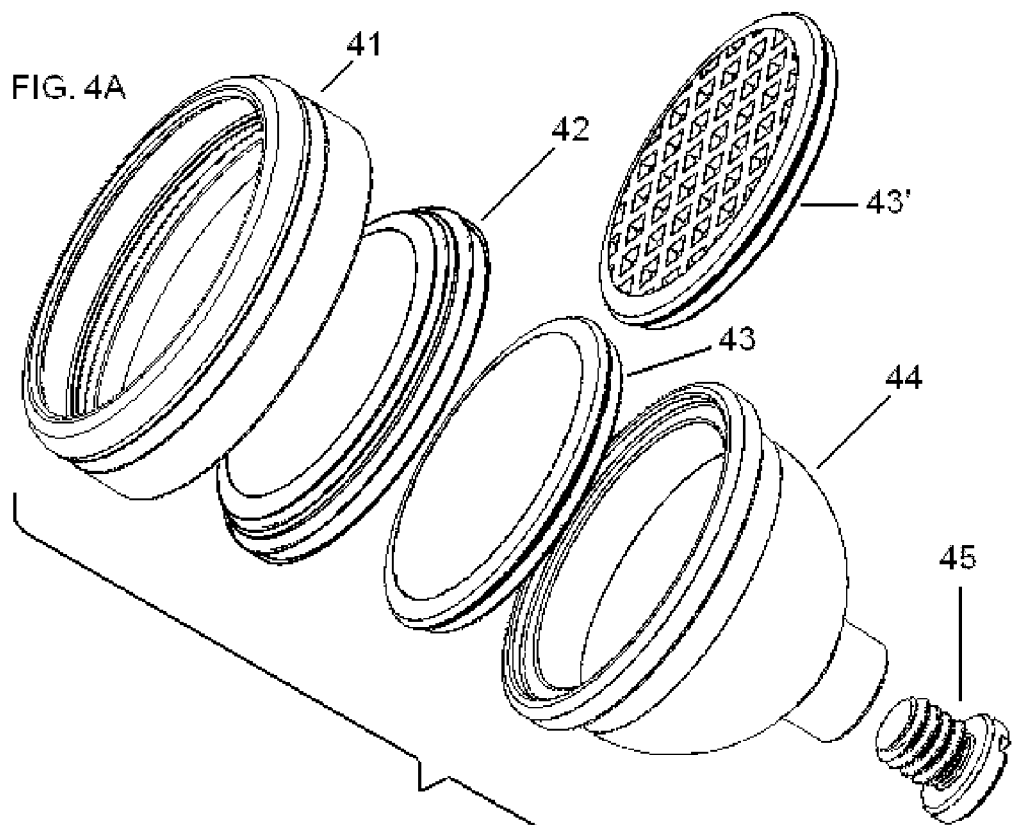
FIG. 4A illustrates a head of the stimulator of FIG. 3A.
Figure 4B:
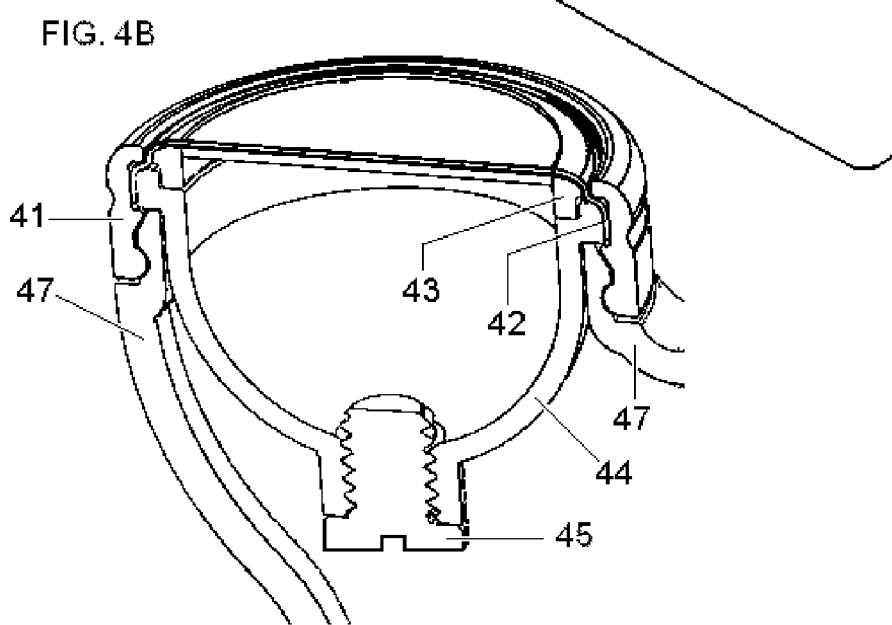
FIG. 4B is a cut-a-way view of the head of FIG. 4A

The alternate embodiment of the stimulator head that is shown in FIG. 4C also contains a snap-on cap (41), membrane (42) that is made of a dielectric or a conducting material, the head-cup (44), and the electrode which is also a screw (45). This alternate embodiment differs from the embodiment shown in FIGS. 4A and 4B in regard to the mechanical support that is provided to the membrane (42). Whereas the disc (43) or (43') had provided mechanical support to the membrane in the other embodiment, in the alternate embodiment a reinforcing ring (40) is provided to the membrane. That reinforcement ring rests on non-conducting struts (49) that are placed in the head-cup (44), and a non-conducting strut-ring (48) is placed within notches in the struts (49) to hold the struts in place. An advantage of the alternate embodiment is that without a disc (43) or (43'), current flow may be less restricted through the membrane (42), especially if the membrane is made of a conducting material. Furthermore, although the struts and strut-ring are made of non-conducting material in this alternate embodiment, the design may be adapted to position additional electrode or other conducting elements within the head-cup for other more specialized configurations of the stimulator head, the inclusion of which will influence the electric fields that are generated by the device. Completed assembly of the alternate stimulator head is shown in FIG. 4D, without showing its attachment to the body of the stimulator. In fact, it is possible to insert a lead under the head of the electrode (45), and many other methods of attaching the electrode to the signal-generating electronics of the stimulator are known in the art.

Figure 4E:
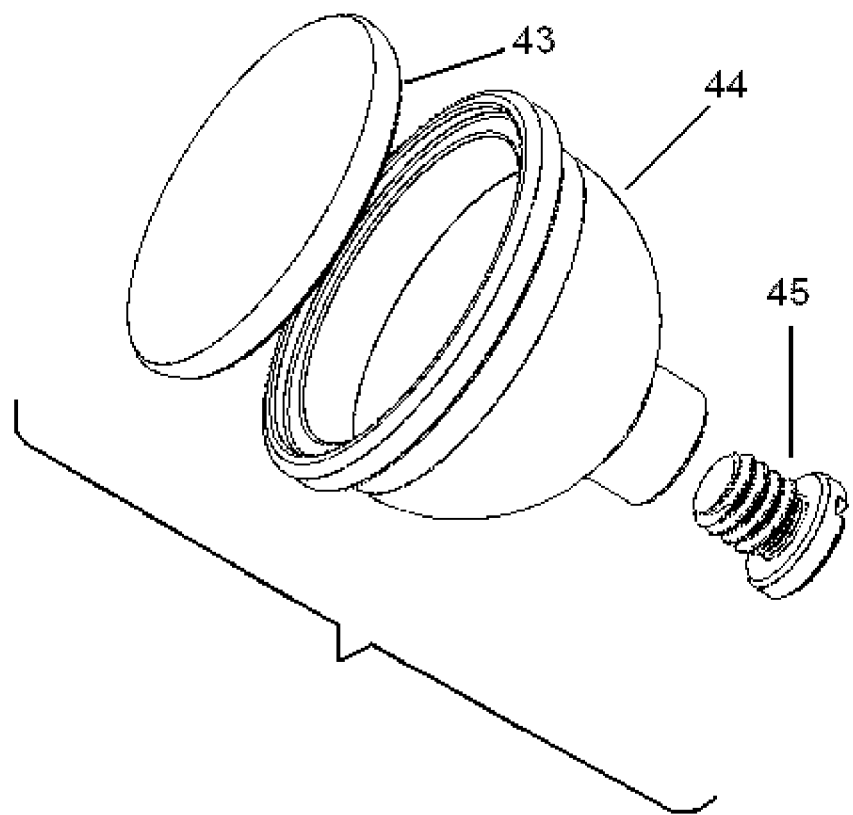
FIG. 4E is a perspective view of yet another embodiment of the head of the stimulator of FIG. 3A.
Figure 4F:
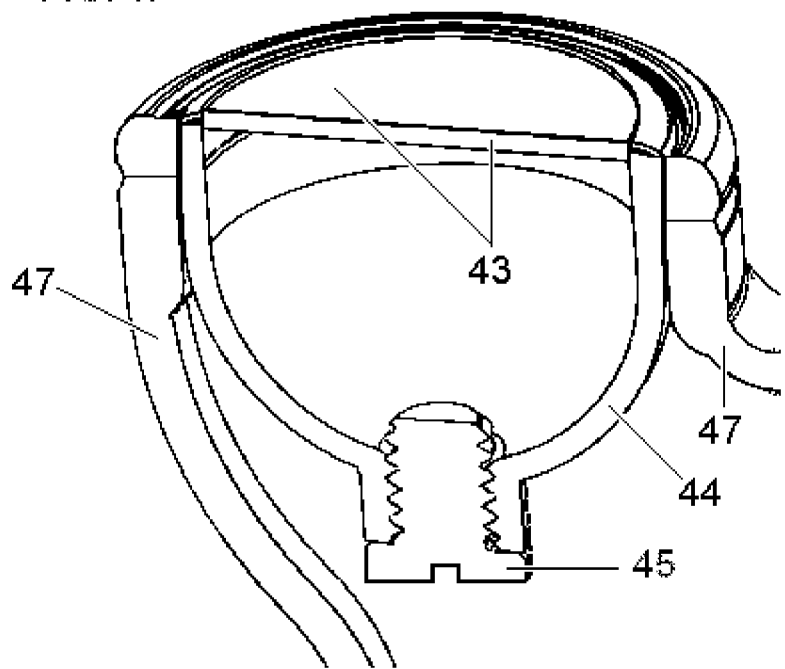
FIG. 4F is a cut-a-way view of the head of FIG. 4E.

If the membrane (42) is made of conducting materials, and the disc (43) in FIG. 4A is made of solid conducting materials such as stainless steel, the membrane becomes optional, and the disc serves as the interface 351 shown in FIG. 1. Thus, an embodiment without the membrane is shown in FIGS. 4E and 4F. FIG. 4E shows that this version of the device comprises a solid (but possibly flexible in some embodiments) conducting disc that cannot absorb fluid (43), the non-conducting stimulator head (44) into or onto which the disc is placed, and the electrode (45), which is also a screw. It is understood that the disc (43) may have an anisotropic material or electrical structure, for example, wherein a disc of stainless steel has a grain, such that the grain of the disc should be rotated about its location on the stimulator head, in order to achieve optimal electrical stimulation of the patient. As seen in FIG. 4F, these items are assembled to become a sealed stimulator head that is attached to the body of the stimulator (47). The disc (43) may screw into the stimulator head (44), it may be attached to the head with adhesive, or it may be attached by other methods that are known in the art. The chamber of the stimulator head-cup is filled with a conducting gel, fluid, or paste, and because the disc (43) and electrode (45) are tightly sealed against the stimulator head-cup (44), the conducting material within the stimulator head cannot leak out.

In some embodiments, the interface and/or its underlying mechanical support comprise materials that will also provide a substantial or complete seal of the interior of the device. This inhibits any leakage of conducting material, such as gel, from the interior of the device and also inhibits any fluids from entering the device. In addition, this feature allows the user to easily clean the outer surface of the device (e.g., with isopropyl alcohol or similar disinfectant), avoiding potential contamination during subsequent uses of the device.

In some embodiments, the interface comprises a fluid permeable material that allows for passage of current through the permeable portions of the material. In these embodiments, a conductive medium (such as a gel) is preferably situated between the electrode(s) and the permeable interface. The conductive medium provides a conductive pathway for electrons to pass through the permeable interface to the outer surface of the interface and to the patient's skin.

In other embodiments of the present invention, the interface (351 in FIG. 1, or 42 in FIG. 4) is made from a very thin material with a high dielectric constant, such as material used to make capacitors. For example, it may be Mylar having a submicron thickness (preferably in the range 0.5 to 1.5 microns) having a dielectric constant of about 3. Because one side of Mylar is slick, and the other side is microscopically rough, the present invention contemplates two different configurations: one in which the slick side is oriented towards the patient's skin, and the other in which the rough side is so-oriented. Thus, at stimulation Fourier frequencies of several kilohertz or greater, the dielectric interface will capacitively couple the signal through itself, because it will have an impedance comparable to that of the skin. Thus, the dielectric interface will isolate the stimulator's electrode from the tissue, yet allow current to pass. In one embodiment of the present invention, non-invasive electrical stimulation of a nerve is accomplished essentially substantially capacitively, which reduces the amount of ohmic stimulation, thereby reducing the sensation the patient feels on the tissue surface. This would correspond to a situation, for example, in which at least 30%, preferably at least 50%, of the energy stimulating the nerve comes from capacitive coupling through the stimulator interface, rather than from ohmic coupling. In other words, a substantial portion (e.g., 50%) of the voltage drop is across the dielectric interface, while the remaining portion is through the tissue.

The selection of the material for the dielectric constant involves at least two important variables: (1) the thickness of the interface; and (2) the dielectric constant of the material. The thinner the interface and/or the higher the dielectric constant of the material, the lower the voltage drop across the dielectric interface (and thus the lower the driving voltage required). For example, with Mylar, the thickness could be about 0.5 to 5 microns (preferably about 1 micron) with a dielectric constant of about 3. For a piezoelectric material like barium titanate or PZT (lead zirconate titanate), the thickness could be about 100-400 microns (preferably about 200 microns or 0.2 mm) because the dielectric constant is >1000.

One of the novelties of the embodiment that is a noninvasive capacitive stimulator (hereinafter referred to more generally as a capacitive electrode) arises in that it uses a low voltage (generally less than 100 volt) power source, which is made possible by the use of a suitable stimulation waveform, such as the waveform that is disclosed herein (FIGS. 2B and 2C). In addition, the capacitive electrode allows for the use of an interface that provides a more adequate seal of the interior of the device. The capacitive electrode may be used by applying a small amount of conductive material (e.g., conductive gel as described above) to its outer surface. In some embodiments, it may also be used by contacting dry skin, thereby avoiding the inconvenience of applying an electrode gel, paste, or other electrolytic material to the patient's skin and avoiding the problems associated with the drying of electrode pastes and gels. Such a dry electrode would be particularly suitable for use with a patient who exhibits dermatitis after the electrode gel is placed in contact with the skin [Ralph J. COSKEY. Contact dermatitis caused by ECG electrode jelly. Arch Dermatol 113 (1977): 839-840]. The capacitive electrode may also be used to contact skin that has been wetted (e.g., with tap water or a more conventional electrolyte material) to make the electrode-skin contact (here the dielectric constant) more uniform [A L ALEXELONESCU, G Barbero, F C M Freire, and R Merletti. Effect of composition on the dielectric properties of hydrogels for biomedical applications. Physiol. Meas. 31 (2010) S169-S182].

As described below, capacitive biomedical electrodes are known in the art, but when used to stimulate a nerve noninvasively, a high voltage power supply is currently used to perform the stimulation. Otherwise, prior use of capacitive biomedical electrodes has been limited to invasive, implanted applications; to non-invasive applications that involve monitoring or recording of a signal, but not stimulation of tissue; to non-invasive applications that involve the stimulation of something other than a nerve (e.g., tumor); or as the dispersive electrode in electrosurgery.

Evidence of a long-felt but unsolved need, and evidence of failure of others to solve the problem that is solved by the this embodiment of the present invention (low-voltage, non-invasive capacitive stimulation of a nerve), is provided by KELLER and Kuhn, who review the previous high-voltage capacitive stimulating electrode of GEDDES et al and write that "Capacitive stimulation would be a preferred way of activating muscle nerves and fibers, when the inherent danger of high voltage breakdowns of the dielectric material can be eliminated. Goal of future research could be the development of improved and ultra-thin dielectric foils, such that the high stimulation voltage can be lowered." [L. A. GEDDES, M. Hinds, and K. S. Foster. Stimulation with capacitor electrodes. Medical and Biological Engineering and Computing 25 (1987): 359-360; Thierry KELLER and Andreas Kuhn. Electrodes for transcutaneous (surface) electrical stimulation. Journal of Automatic Control, University of Belgrade 18(2, 2008):35-45, on page 39]. It is understood that in the United States, according to the 2005 National Electrical Code, high voltage is any voltage over 600 volts. U.S. Pat. No. 3,077,884, entitled Electro-physiotherapy apparatus, to BARTROW et al, U.S. Pat. No. 4,144,893, entitled Neuromuscular therapy device, to HICKEY and U.S. Pat. No. 7,933,648, entitled High voltage transcutaneous electrical stimulation device and method, to TANRISEVER, also describe high voltage capacitive stimulation electrodes. U.S. Pat. No. 7,904,180, entitled Capacitive medical electrode, to JUOLA et al, describes a capacitive electrode that includes transcutaneous nerve stimulation as one intended application, but that patent does not describe stimulation voltages or stimulation waveforms and frequencies that are to be used for the transcutaneous stimulation. U.S. Pat. No. 7,715,921, entitled Electrodes for applying an electric field in-vivo over an extended period of time, to PALTI, and U.S. Pat. No. 7,805,201, entitled Treating a tumor or the like with an electric field, to PALTI, also describe capacitive stimulation electrodes, but they are intended for the treatment of tumors, do not disclose uses involving nerves, and teach stimulation frequencies in the range of 50 kHz to about 500 kHz.

This embodiment of the present invention uses a different method to lower the high stimulation voltage than developing ultra-thin dielectric foils, namely, to use a suitable stimulation waveform, such as the waveform that is disclosed herein (FIGS. 2B and 2C). That waveform has significant Fourier components at higher frequencies than waveforms used for transcutaneous nerve stimulation as currently practiced. Thus, one of ordinary skill in the art would not have combined the claimed elements, because transcutaneous nerve stimulation is performed with waveforms having significant Fourier components only at lower frequencies, and noninvasive capacitive nerve stimulation is performed at higher voltages. In fact, the elements in combination do not merely perform the function that each element performs separately. The dielectric material alone may be placed in contact with the skin in order to perform pasteless or dry stimulation, with a more uniform current density than is associated with ohmic stimulation, albeit with high stimulation voltages [L. A. GEDDES, M. Hinds, and K. S. Foster. Stimulation with capacitor electrodes. Medical and Biological Engineering and Computing 25 (1987): 359-360; Yongmin KIM, H. Gunter Zieber, and Frank A. Yang. Uniformity of current density under stimulating electrodes. Critical Reviews in Biomedical Engineering 17(1990, 6): 585-619]. With regard to the waveform element, a waveform that has significant Fourier components at higher frequencies than waveforms currently used for transcutaneous nerve stimulation may be used to selectively stimulate a deep nerve and avoid stimulating other nerves, as disclosed herein for both noncapacitive and capacitive electrodes. But it is the combination of the two elements (dielectric interface and waveform) that makes it possible to stimulate a nerve capacitively without using the high stimulation voltage as is currently practiced.

Another embodiment of the electrode-based stimulator is shown in FIG. 5, showing a device in which electrically conducting material is dispensed from the device to the patient's skin. In this embodiment, the interface (351 in FIG. 1) is the conducting material itself. FIGS. 5A and 5B respectively provide top and bottom views of the outer surface of the electrical stimulator 50. FIG. 5C provides a bottom view of the stimulator 50, after sectioning along its long axis to reveal the inside of the stimulator.

Figure 5A:
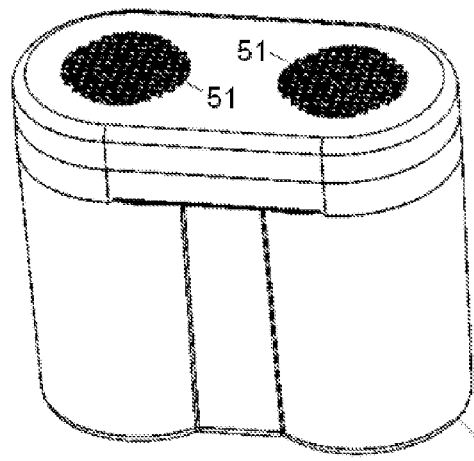
FIG. 5A is a perspective view of the top of a dual-electrode stimulator according to yet another embodiment of the present invention.
Figure 5B:
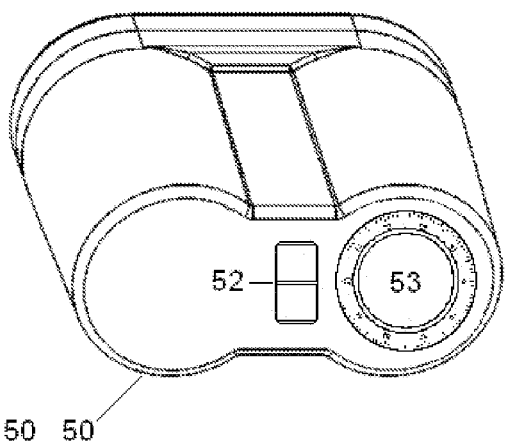
FIG. 5B is a perspective view of the bottom of the stimulator of FIG. 5B.
Figure 5C:
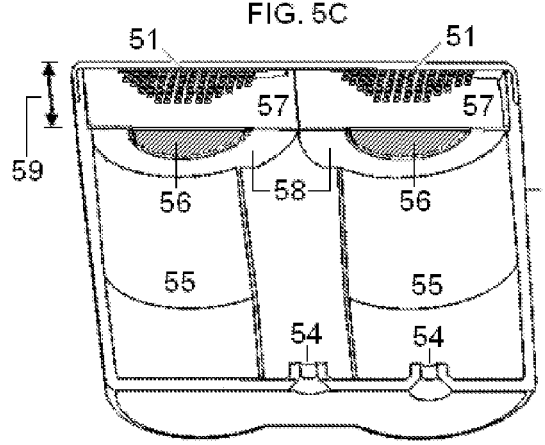
FIG. 5C is a cut-a-way view of the stimulator of FIG. 5A.

FIGS. 5A and 5C show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 5A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

FIGS. 5B and 5C show the bottom of the self-contained stimulator 50. An on/off switch 52 is attached through a port 54, and a power-level controller 53 is attached through another port 54. The switch is connected to a battery power source (320 in FIG. 1B), and the power-level controller is attached to the control unit (330 in FIG. 1B) of the device. The power source battery and power-level controller, as well as the impulse generator (310 in FIG. 1B) are located (but not shown) in the rear compartment 55 of the housing of the stimulator 50.

Individual wires (not shown) connect the impulse generator (310 in FIG. 1B) to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel (350 in FIG. 1B) to each head compartment 57. An optional non-conducting variable-aperture iris diaphragm may be placed in front of each of the electrodes within the head compartment 57, in order to vary the effective surface area of each of the electrodes. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another. Although the embodiment in FIG. 5 is shown to be a non-capacitive stimulator, it is understood that it may be converted into a capacitive stimulator by replacing the mesh openings 51 with a dielectric material, such as a sheet of Mylar, or by covering the mesh openings 51 with a sheet of such dielectric material.

In a preferred embodiment, the magnetic stimulator coil 341 in FIG. 1A has a body that is similar to the electrode-based stimulator shown in FIG. 5C. To compare the electrode-based stimulator with the magnetic stimulator, refer to FIG. 5D, which shows the magnetic stimulator 530 sectioned along its long axis to reveal its inner structure. As described below, it reduces the volume of conducting material that must surround a toroidal coil, by using two toroids, side-by-side, and passing electrical current through the two toroidal coils in opposite directions. In this configuration, the induced electrical current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

Figure 5D:
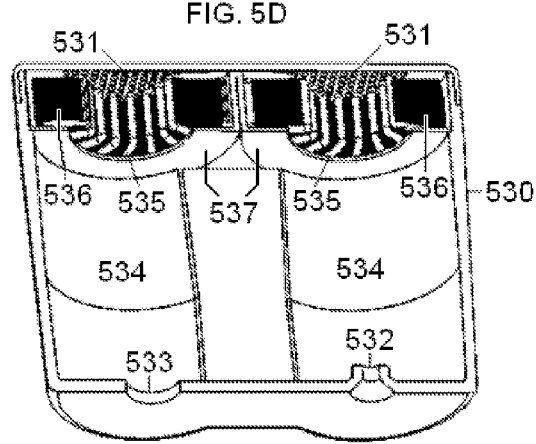
FIG. 5D is a cut-a-way view of the stimulator of FIG. 5B.

As seen in FIG. 5D, a mesh 531 has openings that permit a conducting gel (within 351 in FIG. 1A) to pass from the inside of the stimulator to the surface of the patient's skin at the location of nerve or tissue stimulation. Thus, the mesh with openings 531 is the part of the magnetic stimulator that is applied to the skin of the patient.

FIG. 5D also shows openings at the opposite end of the magnetic stimulator 530. One of the openings is an electronics port 532 through which wires pass from the stimulator coil(s) to the impulse generator (310 in FIG. 1A). The second opening is a conducting gel port 533 through which conducting gel (351 in FIG. 1A) may be introduced into the magnetic stimulator 530 and through which a screw-driven piston arm may be introduced to dispense conducting gel through the mesh 531. The gel itself is contained within cylindrical-shaped but interconnected conducting medium chambers 534 that are shown in FIG. 5D. The depth of the conducting medium chambers 534, which is approximately the height of the long axis of the stimulator, affects the magnitude of the electric fields and currents that are induced by the magnetic stimulator device [Rafael CARBUNARU and Dominique M. Durand. Toroidal coil models for transcutaneous magnetic stimulation of nerves. IEEE Transactions on Biomedical Engineering. 48 (4, 2001): 434-441].

FIG. 5D also show the coils of wire 535 that are wound around toroidal cores 536, consisting of high-permeability material (e.g., Supermendur). Lead wires (not shown) for the coils 535 pass from the stimulator coil(s) to the impulse generator (310 in FIG. 1A) via the electronics port 532. Different circuit configurations are contemplated. If separate lead wires for each of the coils 535 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As also seen in FIG. 5D, the coils 535 and cores 536 around which they are wound are mounted as close as practical to the corresponding mesh 531 with openings through which conducting gel passes to the surface of the patient's skin. As shown, each coil and the core around which it is wound is mounted in its own housing 537, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium. A difference between the structure of the electrode-based stimulator shown in FIG. 5C and the magnetic stimulator shown in FIG. 5D is that the conducting gel is maintained within the chambers 57 of the electrode-based stimulator, which is generally closed on the back side of the chamber because of the presence of the electrode 56; but in the magnetic stimulator, the hole of each toroidal core and winding is open, permitting the conducting gel to enter the interconnected chambers 534.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance. The currents passing through the coils of the magnetic stimulator will saturate the core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described in connection with FIG. 2. Additional disclosure of the magnetic stimulator shown in FIG. 1A is provided in Applicant's commonly assigned co-pending U.S. patent application Ser. No. 12/964,050, entitled Magnetic Stimulation Devices and Methods of Therapy, to SIMON et al., which is hereby incorporated by reference for all purposes.

In preferred embodiments of the electrode-based stimulator shown in FIG. 1B, electrodes are made of a metal, such as stainless steel, platinum, or a platinum-iridium alloy. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18(2, 2008):35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004): 346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20(1, 1994):29-35].

For example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes. Annu. Rev. Biomed. Eng. 2008. 10:275-309; Michael F. NOLAN. Conductive differences in electrodes used with transcutaneous electrical nerve stimulation devices. Physical Therapy 71 (1991):746-751].

Although the electrode may consist of arrays of conducting material, the embodiments shown in FIGS. 3 to 5 avoid the complexity and expense of array or grid electrodes [Ana POPOVIC-BIJELIC, Goran Bijelic, Nikola Jorgovanovic, Dubravka Bojanic, Mirjana B. Popovic, and Dejan B. Popovic. Multi-Field Surface Electrode for Selective Electrical Stimulation. Artificial Organs 29 (6, 2005):448-452; Dejan B. POPOVIC and Mirjana B. Popovic. Automatic determination of the optimal shape of a surface electrode: Selective stimulation. Journal of Neuroscience Methods 178 (2009) 174-181; Thierry KELLER, Marc Lawrence, Andreas Kuhn, and Manfred Morari. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197]. This is because the designs shown in FIGS. 3 to 5 provide a uniform surface current density, which would otherwise be a potential advantage of electrode arrays, and which is a trait that is not shared by most electrode designs [Kenneth R. BRENNEN. The Characterization of Transcutaneous Stimulating Electrodes. IEEE Transactions on Biomedical Engineering BME-23 (4, 1976): 337-340; Andrei PATRICIU, Ken Yoshida, Johannes J. Struijk, Tim P. DeMonte, Michael L. G. Joy, and Hans Stødkilde-Jørgensen. Current Density Imaging and Electrically Induced Skin Burns Under Surface Electrodes. IEEE Transactions on Biomedical Engineering 52 (12, 2005): 2024-2031; R. H. GEUZE. Two methods for homogeneous field defibrillation and stimulation. Med. and Biol. Eng. and Comput. 21 (1983), 518-520; J. PETROFSKY, E. Schwab, M. Cuneo, J. George, J. Kim, A. Almalty, D. Lawson, E. Johnson and W. Remigo. Current distribution under electrodes in relation to stimulation current and skin blood flow: are modern electrodes really providing the current distribution during stimulation we believe they are? Journal of Medical Engineering and Technology 30 (6, 2006): 368-381; Russell G. MAUS, Erin M. McDonald, and R. Mark Wightman. Imaging of Nonuniform Current Density at Microelectrodes by Electrogenerated Chemiluminescence. Anal. Chem. 71 (1999): 4944-4950]. In fact, patients found the design shown in FIGS. 3 to 5 to be less painful in a direct comparison with a commercially available grid-pattern electrode [UltraStim grid-pattern electrode, Axelggard Manufacturing Company, 520 Industrial Way, Fall brook CA, 2011]. The embodiment of the electrode that uses capacitive coupling is particularly suited to the generation of uniform stimulation currents [Yongmin KIM, H. Gunter Zieber, and Frank A. Yang. Uniformity of current density under stimulating electrodes. Critical Reviews in Biomedical Engineering 17(1990, 6): 585-619].

The electrode-based stimulator designs shown in FIGS. 3 to 5 situate the electrode remotely from the surface of the skin within a chamber, with conducting material placed in the chamber between the skin and electrode. Such a chamber design had been used prior to the availability of flexible, flat, disposable electrodes [U.S. Pat. No. 3,659,614, entitled Adjustable headband carrying electrodes for electrically stimulating the facial and mandibular nerves, to Jankelson; U.S. Pat. No. 3,590,810, entitled Biomedical body electode, to Kopecky; U.S. Pat. No. 3,279,468, entitled Electrotherapeutic facial mask apparatus, to Le Vine; U.S. Pat. No. 6,757, 556, entitled Electrode sensor, to Gopinathan et al; U.S. Pat. No. 4,383,529, entitled Iontophoretic electrode device, method and gel insert, to Webster; U.S. Pat. No. 4,220,159, entitled Electrode, to Francis et al. U.S. Pat. Nos. 3,862,633, 4,182,346, and 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing bioelectrode, to Jacobsen et al.] The stimulator designs shown in FIGS. 3 to 5 are also self-contained units, housing the electrodes, signal electronics, and power supply. Portable stimulators are also known in the art, for example, U.S. Pat. No. 7,171,266, entitled Electro-acupuncture device with stimulation electrode assembly, to Gruzdowich. One of the novelties of the designs shown in FIGS. 3 to 5 is that the stimulator, along with a correspondingly suitable stimulation waveform, shapes the electric field, producing a selective physiological response by stimulating that nerve, but avoiding substantial stimulation of nerves and tissue other than the target nerve, particularly avoiding the stimulation of nerves that produce pain.

The remaining disclosure will be directed to methods for using the above-disclosed electrode-based and magnetic stimulation devices for treating atrial fibrillation, including methods for detecting imminent AF onset and using the stimulation devices to avert the onset of that AF. The examples involve stimulating the patient on the surface of the patient's neck in order to stimulate one or both of the patient's vagus nerves. However, it will be appreciated that the systems and methods of the present invention might be applied equally well to other nerves of the body, including but not limited to parasympathetic nerves, sympathetic nerves, and spinal or cranial nerves.

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retropharyngeal space on each side of the neck and deep to the sternocleidomastoid muscle. The left vagus nerve is sometimes selected for stimulation because stimulation of the right vagus nerve may produce undesired effects on the heart, but in the present application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The electrodes or magnetic stimulator coils may be centered on such a point, at the level of about the fifth to sixth cervical vertebra.

Figure 6:
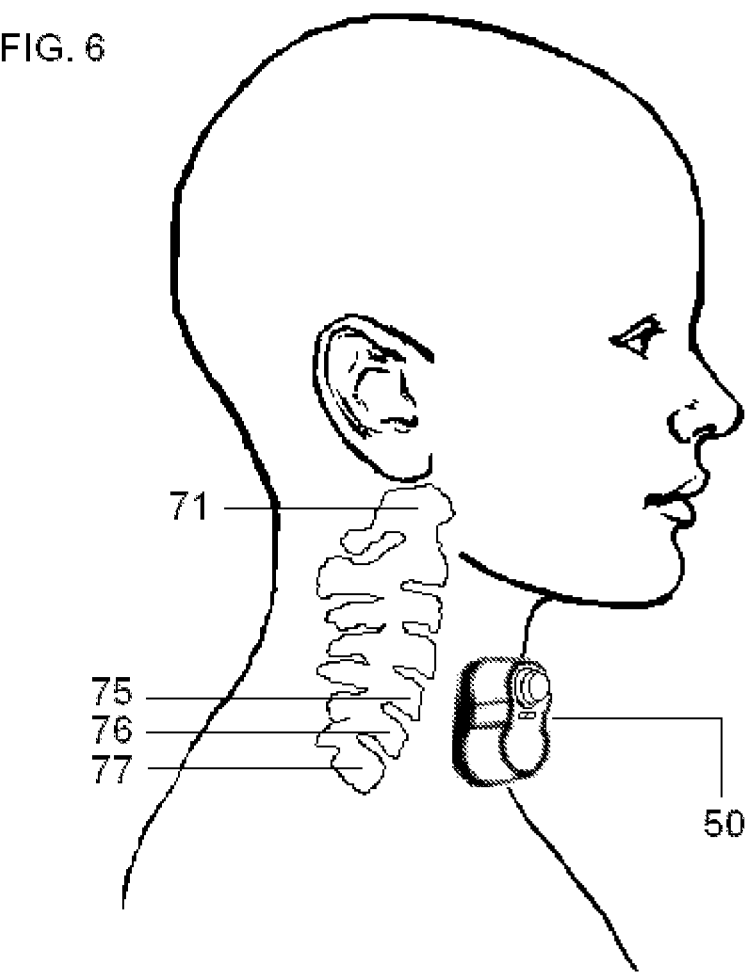
FIG. 6 illustrates the approximate position of the housing of the dual-electrode stimulator according one embodiment of the present invention, when the electrodes are used to stimulate the vagus nerve in the neck of a patient.

FIG. 6 illustrates use of the devices shown in FIGS. 3 to 5 to stimulate the vagus nerve at that location in the neck, in which the stimulator device 50 in FIG. 5 is shown to be applied to the target location on the patient's neck as described above. For reference, locations of the following vertebrae are also shown: first cervical vertebra 71, the fifth cervical vertebra 75, the sixth cervical vertebra 76, and the seventh cervical vertebra 77.

Figure 7:
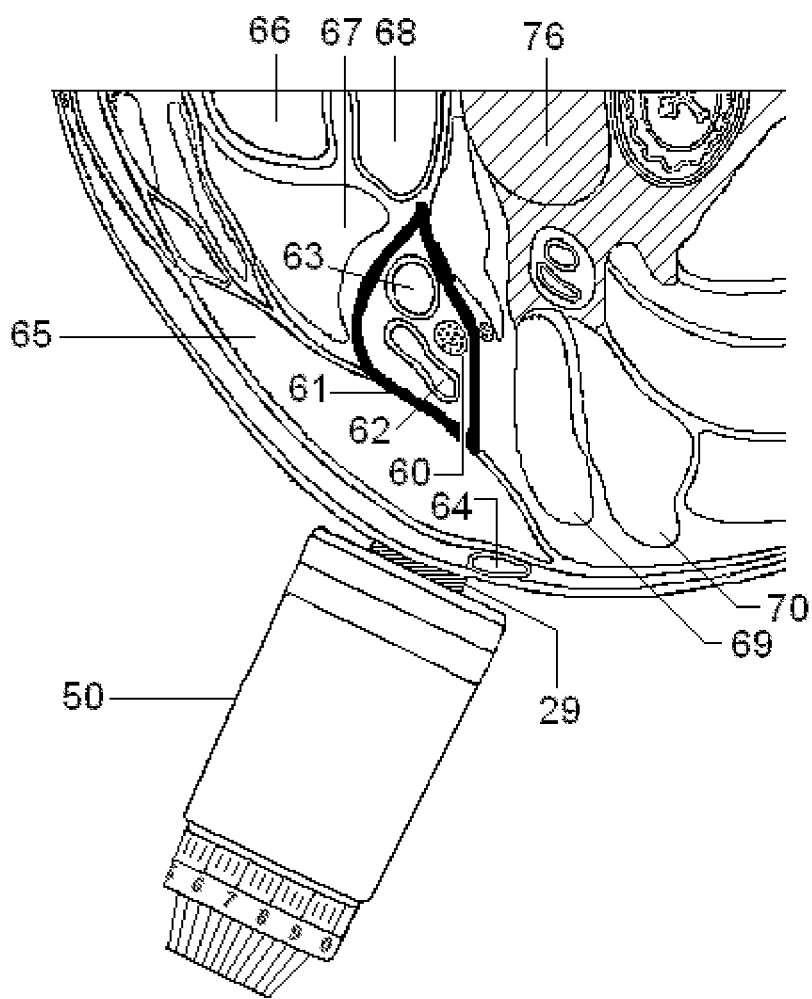
FIG. 7 illustrates the housing of the dual-electrode stimulator according one embodiment of the present invention, as the electrodes are positioned to stimulate a vagus nerve in a patient's neck, such that the stimulator is applied to the surface of the neck in the vicinity of the identified anatomical structures.

FIG. 7 provides a more detailed view of use of the electrical stimulator, when positioned to stimulate the vagus nerve at the neck location that is indicated in FIG. 6. As shown, the stimulator 50 in FIG. 5 touches the neck indirectly, by making electrical contact through conducting gel 29 (or other conducting material) which may be is dispensed through mesh openings (identified as 51 in FIG. 5) of the stimulator or applied as an electrode gel or paste. The layer of conducting gel 29 in FIG. 7 is shown to connect the device to the patient's skin, but it is understood that the actual location of the gel layer(s) may be generally determined by the location of mesh 51 shown in FIG. 5. Furthermore, it is understood that for other embodiments of the invention, the conductive head of the device may not necessitate the use of additional conductive material being applied to the skin.

The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

The position and angular orientation of the device are adjusted about the location indicated in FIGS. 6 and 7 until the patient perceives stimulation when current is passed through the stimulator. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7).

The stimulation is then performed with a sinusoidal burst waveform like that shown in FIG. 2. The pattern of a burst followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds, which is comparable to 25 Hz stimulation. More generally, there may be 1 to 20 pulses per burst, preferably five pulses. Each pulse within a burst has a duration of 20 to 1000 microseconds, preferably 200 microseconds. A burst followed by a silent inter-burst interval repeats at 1 to 5000 bursts per second (bps), preferably at 5-50 bps, and even more preferably 10-25 bps stimulation (10-25 Hz). The preferred shape of each pulse is a full sinusoidal wave, although triangular or other shapes may be used as well. The stimulation is then performed typically for 30 minutes or until the desired therapeutic effect is achieved. However, it is understood that parameters of the stimulation protocol may be varied in response to heterogeneity in the pathophysiology of patients.

The stimulator signal may have a frequency and other parameters that are selected to produce a therapeutic result in the patient, which are adjusted on an individualized basis. The individualized selection of parameters for the nerve stimulation protocol may based on trial and error in order to obtain a beneficial response without the sensation of pain, muscle twitches, or other adverse side effects. Ordinarily, the amplitude of the stimulation signal is set to the maximum that is comfortable for the patient, and to a level that does not cause a vagally-induced slowing of the heart rate for patients who are in sinus rhythm, or would not have caused such slowing, for patients who are already experiencing AF. Then, the other stimulation parameters are adjusted. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10(5, 2004):378-82].

Individualized treatment may also be based on the methods that are described below in connection with the use of control theory to select stimulation parameters, in which stimulation parameters can be varied automatically in response to noninvasive physiological signals that are acquired and analyzed (ECG, particularly analysis of the f-wave in patients experiencing AF; respiration; motion detected by accelerometers, etc). In order to motivate exemplary control rules that are disclosed below, the neural control of the heart by the autonomic nervous system will first be described.

Both parasympathetic and sympathetic components of the autonomic nervous system have significant influences on the onset and maintenance of AF, and the presence of AF may in turn modulate the autonomic nervous system [Philippe COUMEL. Autonomic influences in atrial tachyarrhythmias.

Journal of Cardiovascular Electrophysiology 7(10, 1996): 999-1007; Peng-Sheng CHEN and Alex Y. Tan. Autonomic nerve activity and atrial fibrillation. Heart Rhythm 4(3 Suppl, 2997):S61-S64; OLSHANSKY B. Interrelationships between the autonomic nervous system and atrial fibrillation. Prog Cardiovasc Dis 48(1, 2005):57-78; CHEN J, Wasmund S L, Hamdan M H. Back to the future: the role of the autonomic nervous system in atrial fibrillation. Pacing Clin Electrophysiol 29(4, 2006):413-21]. Vagally-mediated AF occurs more frequently than adrenergically-mediated AF, with the former occurring sufficiently often that an AF patient with enhanced vagal tone may be diagnosed as having "vagal AF" [Yung-Hsin YEH, Kristina Lemola and Stanley Nattel. Vagal atrial fibrillation. Acta Cardiol Sin 23 (2007): 1-12]. Direct infusion of acetylcholine into animal models can almost invariably induce AF, but direct infusion of isoprenaline and adrenaline can induce AF in only approximately one-fourth of such animals. The differential effect of parasympathetic versus sympathetic stimulation in inducing AF may be due to the fact that effects of sympathetic stimulation are much more homogeneous in the atria than those associated with vagal activity [LIU L, Nattel S. Differing sympathetic and vagal effects on atrial fibrillation in dogs: role of refractoriness heterogeneity. Am J Physiol 273(2 Pt 2, 1997):H805-16]. However, changes in the autonomic nervous system that accompany remodeling of the atria may significantly increase the likelihood that sympathetic stimulation induces AF [FURUKAWA T, Hirao K, Horikawa-Tanami T, Hachiya H, Isobe M. Influence of autonomic stimulation on the genesis of atrial fibrillation in remodeled canine atria not the same as in normal atria. Circ. 173(3, 2009):468-75].

Clinical maneuvers that are known to modulate the autonomic nervous system have been shown to influence the presence or characteristics of AF. Carotid sinus massage induces AF in some patients and terminates AF in others [BOLLMANN A, Wodarz K, Esperer H D, Toepffer I, Klein H U. Response of atrial fibrillatory activity to carotid sinus massage in patients with atrial fibrillation. Pacing Clin Electrophysiol 24(9 Pt 1, 2001):1363-8]. Sympathetic activation by exercise may increase or decrease AF fibrillatory frequency in some patients [HUSSER O, Husser D, Stridh M, Sörnmo L, Klein H U, Bollmann A. Exercise testing for non-invasive assessment of atrial electrophysiology in patients with persistent atrial fibrillation. Computers in Cardiology 33 (2006):21-24]. Controlled respiration causes cyclic fluctuations in the AF fibrillatory frequency in patients with AF [HOLMQVIST F, Stridh M, Waktare J E, Brandt J, Sörnmo L, Roijer A, Meurling O. Rapid fluctuations in atrial fibrillatory electrophysiology detected during controlled respiration. Am J Physiol Heart Circ Physiol 289(2, 2005): H754-60]. A head-up tilt test modulates the autonomic nervous system, producing a change in the AF fibrillatory frequency [M INGEMANSSON, M Holm, and S Olsson. Autonomic modulation of the atrial cycle length by the head up tilt test: non-invasive evaluation in patients with chronic atrial fibrillation. Heart 80(1, 1998): 71-76]. Pulsatile neck suction also produces rhythm changes in AF patients and may shorten atrial refractoriness [KNEIP C F, Mallet R T, Williams A G, Hamdan M H, Smith M L. Vagal modulation of heart rate variability during atrial fibrillation in pigs. Exp Biol Med 235(8, 2010):1007-14; PRYSTOWSKY E N, Naccarelli G V, Jackman W M, Rinkenberger R L, Heger J J, Zipes D P. Enhanced parasympathetic tone shortens atrial refractoriness in man. Am J Cardiol 51(1, 1983):96-100]. Sympathetic stimulation induced by intermittent handgrip of submaximal activity, stimulated vagal activity induced by right carotid sinus massage, and pharmacological blockade all influence the properties of AF [OLIVEIRA M, da Silva N, Cunha P, Ramos R, Marques F, Santos S, Rocha I, Silva-Carvalho L, Ferreira R. Effects of acute autonomic modulation on atrial conduction delay and local electrograms duration in paroxysmal atrial fibrillation. Int J Cardiol 149(3, 2011):290-5]. However, such maneuvers may be unwieldy when compared with a vagal nerve stimulation protocol that allows simultaneous fine-control over stimulus amplitude, frequency, pulse width, etc., but those maneuvers may also be used in conjunction with electrical stimulation of the vagus nerve.

Figure 8:
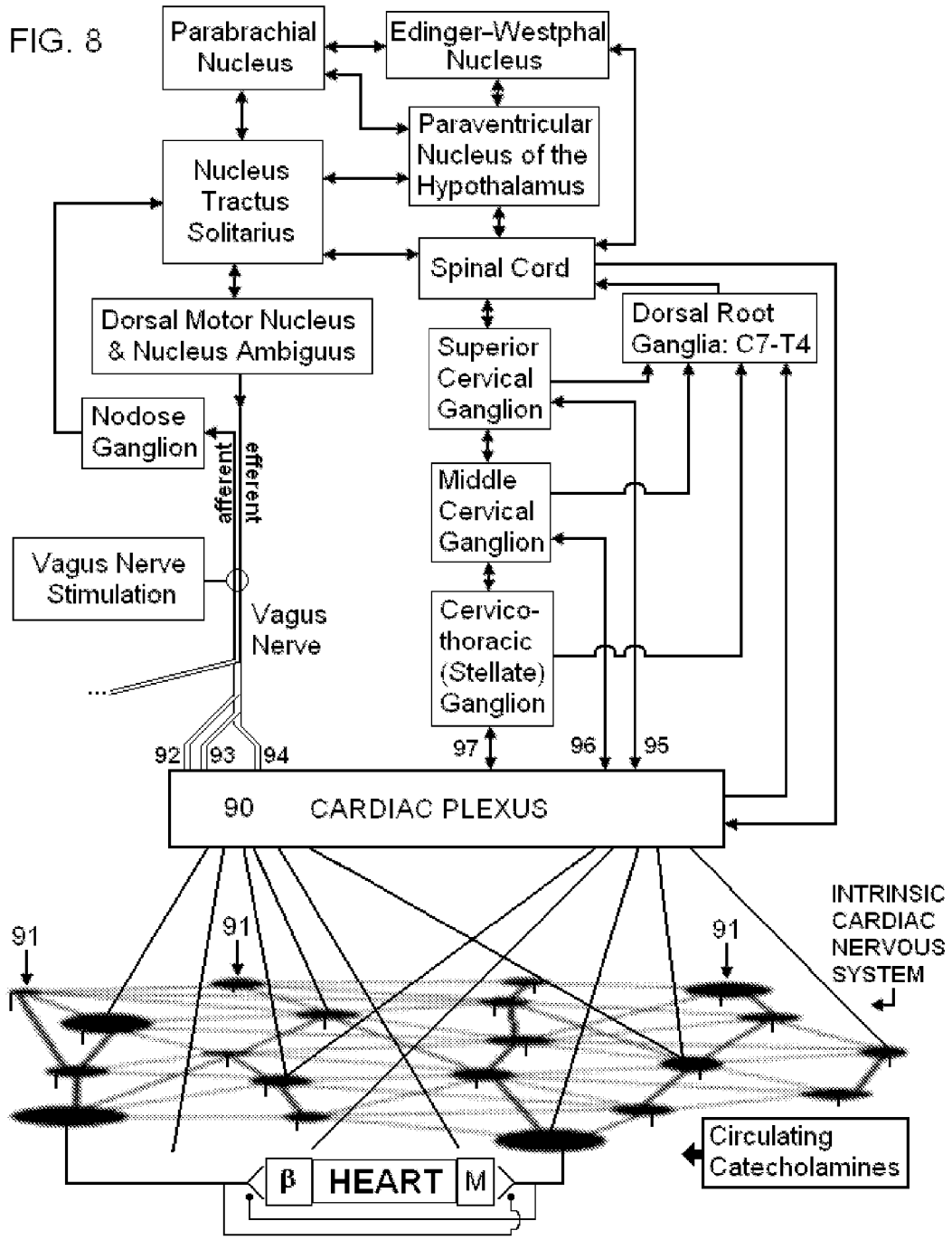
FIG. 8 illustrates intrinsic and extrinsic nerves that control the heart, including the vagus nerve that is stimulated by the disclosed devices.

Control of the heart by the autonomic nervous system is illustrated in FIG. 8. Parasympathetic components, particularly the vagus nerve, are shown primarily on the left side of the figure, and sympathetic components are shown primarily on the right side of the figure. The site of vagus nerve stimulation that is shown in FIG. 8 corresponds to the site illustrated in FIGS. 6 and 7. It is understood that there are left and right vagus nerves, and that the sympathetic trunk also comprises paired bundles of nerve fibers, but for simplicity only one side is shown in FIG. 8. Furthermore, it is understood that the two sides may interact and show asymmetries, for example, such that stimulation of the right vagus nerve may produce effects that differ from those obtained by stimulating the left vagus nerve.

Electrical stimulation of a vagus nerve will produce, inhibit, or modulate action potentials in both its afferent and efferent fibers, unless the nerve stimulation parameters are selected in such a way as to preferentially stimulate particular fibers. Antidromic impulses might also be produced by stimulation of the vagus nerve. Efferent signals arising from stimulation of the vagus nerve may be superimposed upon, or interact with, the vagal efferent signals from the brainstem. The vagal afferent signals from the nerve stimulation, as well as naturally occurring cardiac sympathetic and parasympathetic afferent signals, are conveyed to the brainstem and processed there As described below, this results in the production of both sympathetic and parasympathetic efferent signals from the control and integration centers of the brainstem. Those efferent signals are in turn conveyed through the deep and superficial cardiac plexuses 90, which are then conveyed to the heart and its intrinsic nervous system.

Parasympathetic cells forming efferent fibers of the vagus nerve are located in nuclei of the brainstem, comprising the dorsal nucleus of the vagus and the nucleus ambiguus (and surrounding cells). Vagal efferent B fibers, arising principally from the nucleus ambiguus, and vagal efferent C fibers, arising principally from the dorsal nucleus, are thought to have different functions in controlling the heart. The vagus nerve originating in these nuclei forms successive branches that innervate the heart, comprising the superior cervical vagal cardiac nerve 92, the inferior cervical vagal cardiac nerve 93, and the thoracic vagal cardiac nerve 94 [CHENG Z, Zhang H, Guo S Z, Wurster R, Gozal D. Differential control over postganglionic neurons in rat cardiac ganglia by NA and DmnX neurons: anatomical evidence. Am J Physiol Regul Integr Comp Physiol 286(4, 2004):R625-33].

The cells of the intermediolateral column in the thoracic spinal cord are the source of all the sympathetic efferent nerve fibers. They travel to ganglia before the corresponding postganglionic nerve reaches the target organ, in this case, the heart. Relevant ganglia (and corresponding nerves), some of which are shown in FIG. 8, comprise the superior cervical ganglion (superior cervical cardiac nerve 95); the middle cervical ganglion (middle cervical cardiac nerve 96); the cervocothoracic (stellate) ganglion (inferior cervical cardiac nerve 97); and first through fourth thoracic sympathetic ganglion (thoracic sympathetic cardiac nerves) [Van STEE E W.

Autonomic innervation of the heart. Environ Health Perspect 26 (1978):151-8; Kawashima T. The autonomic nervous system of the human heart with special reference to its origin, course, and peripheral distribution. Anat Embryol 209(6, 2005):425-38; M. P. S. MAURO, F. Patronelli, E. Spinelli, A. Cordero, D. Covello, J. A. Gorostiaga. Nerves of the heart: a comprehensive review with a clinical point of view. Neuroanatomy 8 (2009):26-31].

Nearly all parasympathetic afferent nerve signals reach the nucleus tractus solitarus (NTS or nucleus of the solitary tract) of the central nervous system via the vagus nerve. Like all sensory afferents, the actual cell bodies of the neurons lie just outside the central nervous system in a ganglion, which for the vagus nerve is the nodose ganglion. The central processes of the neurons enter the medulla in the solitary tract and travel a short distance before making a synapse in the surrounding nucleus of the solitary tract. The sympathetic afferents reenter the dorsal horn of the spinal cord from levels C7 to T4, notably at the same level as those from the shoulder region, such that shoulder and cardiac pain is sometimes indistinguishable. Information about the status of the heart is conveyed by these parasympathetic and sympathetic afferent nerves to the brainstem, where it is integrated along with autonomic information about respiration, body temperature, etc., to produce corresponding efferent cardiac signals.

Much of the integration of autonomic information is performed in the NTS, parabrachial nucleus (PBN), and Edinger-Westphal nucleus (EW). As shown in FIG. 8, the NTS projects to the PBN, and the PBN projects to the EW. Within the brain stem, integration of autonomic activity may occur via pathways that project: (a) from EW to PBN; (b) from PBN to NTS; (c) from NTS to the paraventricular nucleus of the hypothalamus (PVN); and (d) from PVN to EW. Pathways that descend from brain stem centers of autonomic integration to the spinal cord originate in the EW, NTS, and PVN [LEOWY, A. D., Burton, H., 1978. Nuclei of the solitary tract: efferent projections to the lower brain stem and spinal cord of the cat. J. Comp. Neurol. 181, 421-449; LEOWY, A. D., Saper, C. B, 1978. Edinger-Westphal nucleus: projections to the brain stem and spinal cord in the cat. Brain Res. 150, 1-27]. Additional integration of sympathetic information may be through local circuits involving feedback via the superior, middle, and/or stellate ganglia, back to the spinal cord through the dorsal root ganglia.

A significant amount of integration of autonomic information also occurs in the intrinsic cardiac autonomic nervous system, which is estimated to contain more than 14,000 neurons. As illustrated in FIG. 8, the intrinsic system is a complex neural network, containing ganglia 91 and their associated axons, which are concentrated within epicardial fat pads in plexi, i.e., ganglionated plexi. In humans, the plexi are observed consistently in five atrial and five ventricular regions, but occasional ganglia of the intrinsic cardiac autonomic nervous system are also located in other atrial and ventricular regions. The ganglia range in size from some containing a few neurons to large ganglia measuring up to 0.5×1 mm [ARMOUR J A, Murphy D A, Yuan B X, Macdonald S, Hopkins D A. Gross and microscopic anatomy of the human intrinsic cardiac nervous system. Anat Rec 247(2, 1997):289-98]. It appears that some left atrial ganglia that are not within a ganglionated plexus may be responsible for the AF that can be induced by stimulation of a vagus nerve [LO L W, Chiou C W, Lin Y J, Lee S H, Chen S A. Neural mechanism of atrial fibrillation: insight from global high density frequency mapping. J Cardiovasc Electrophysiol 22(9, 2011): 1049-56].

Postganglionic parasympathetic and sympathetic cholinergic nerves affect cardiac muscarinic receptors (shown as M in FIG. 8 to represent the five principal types of cardiac muscarinic receptors), which have multiple effects such as activating acetylcholine-regulated potassium current and modifying sympathetic inputs. Also through such ganglia, the sympathetic nervous system activates cardiac adrenergic receptors (shown as β in FIG. 8 to represent the several cardiac α and β adrenergic receptors), which have multiple effects such as modifying parasympathetic inputs and activating second messengers. However, the neurochemistry of the intrinsic cardiac nervous system is complicated by the fact that half of their cholinergic neurons may have a dual cholinergic/noradrenergic phenotype. In addition to nerve transmissions involving acetylcholine and norepinephrine, other modulators such as neuropeptide Y and vasoactive intestinal peptide are also involved [HOARD J L, Hoover D B, Mabe A M, Blakely R D, Feng N, Paolocci N. Cholinergic neurons of mouse intrinsic cardiac ganglia contain noradrenergic enzymes, norepinephrine transporters, and the neurotrophin receptors tropomyosin-related kinase A and p75. Neuroscience 156(1, 2008):129-42; OLSHANSKY B. Interrelationships between the autonomic nervous system and atrial fibrillation. Prog Cardiovasc Dis 48(1, 2005):57-78; GRAY A L, Johnson T A, Lauenstein J M, Newton S S, Ardell J L, Massari V J. Parasympathetic control of the heart. III. Neuropeptide Y-immunoreactive nerve terminals synapse on three populations of negative chronotropic vagal preganglionic neurons. J Appl Physiol 96(6, 2004):2279-87; YANG D, Xi Y, Ai T, Wu G, Sun J, Razavi M, Delapasse S, Shurail M, Gao L, Mathuria N, Elayda M, Cheng J. Vagal stimulation promotes atrial electrical remodeling induced by rapid atrial pacing in dogs: evidence of a noncholinergic effect. Pacing Clin Electrophysiol 34(9, 2011):1092-9].

The intrinsic cardiac autonomic nervous system is not simply a relay station for extrinsic autonomic nerve projections to and from the heart. It is instead a local integrative neural network that can modulate external nervous signals sent to and from the heart [HOU Y, Scherlag B J, Lin J, Zhang Y, Lu Z, Truong K, Patterson E, Lazzara R, Jackman W M, Po S S. Ganglionated plexi modulate extrinsic cardiac autonomic nerve input: effects on sinus rate, atrioventricular conduction, refractoriness, and inducibility of atrial fibrillation. Am Coll Cardiol 50(1, 2007):61-8]. The intrinsic cardiac autonomic nervous system can also act independently and reflexively in response to local cardiac signals, thereby acting as a "little brain on the heart". In fact, in transplanted hearts that have no external innervations until new nerve fibers sprout, the intrinsic cardiac autonomic nervous system nevertheless maintains a degree of control over cardiac functions. In that case, the only remaining sources of external control are humoral, particularly circulating catecholamines. Furthermore, atrial fibrillation can be induced by electrically stimulating only ganglionated plexi of the intrinsic nervous system, or by injecting acetylcholine directly into them [SCHERLAG B J, Po S. The intrinsic cardiac nervous system and atrial fibrillation. Curr Opin Cardiol 21(1, 2006):51-4; B KUKANOVA and B Mravec. Complex intracardiac nervous system. Bratisl Lek Listy 107(3, 2006):45-51; PO SS, Yu L, Scherlag B J. Cardiac autonomic nervous system: a tug of war between the big brain and little brain—friends or foes? Heart Rhythm 6(12, 2009):1780-1; ZHANG Y, Scherlag B J, Lu Z, Niu G D, Yamanashi W S, Hogan C, Fields J, Ghias M, Lazzara R, Jackman W M, Po S. Comparison of atrial fibrillation inducibility by electrical stimulation of either the extrinsic or the intrinsic autonomic nervous systems. Interv Card Electrophysiol 24(1, 2009):5-10; GRAY A L, Johnson T A, Ardell J L, Massari V J. Parasympathetic control of the heart. II. A novel interganglionic intrinsic cardiac circuit mediates neural control of heart rate. J Appl Physiol 96(6, 2004):2273-8].

In summary, the neural control of the heart that is shown in FIG. 8 is hierarchical, with interacting integrative circuits at different levels from the brainstem to the intrinsic cardiac autonomic nervous system. It is no longer thought that thoracic and intrinsic cardiac ganglia simply act as relay stations. Instead, the various populations of neurons constantly interact with one another and with central neurons to form reflexes of varied latency that control spatially determined but overlapping regions of the heart. Short latency (20-40 millisecond) reflexes may involve primarily the intrinsic cardiac ganglia; medium-latency (100-200 millisecond) reflexes may involve thoracic ganglia; and longer-latency reflexes may involve the spinal cord and brainstem [ARMOUR J A. The little brain on the heart. Cleve Clin J Med 74(Suppl 1, 2007): 548-51; ARMOUR J A. Potential clinical relevance of the 'little brain' on the mammalian heart. Exp Physiol 93(2, 2008):165-76; ONDICOVA K, Mravec B. Multilevel interactions between the sympathetic and parasympathetic nervous systems: a minireview. Endocr Regul 44(2, 2010):69-75].

Although particular cardiac regions are subserved by nearby cardiac intrinsic ganglia, the interactions among cardiac ganglia, and interactions with components of the extrinsic nervous system with which they are in communication, are such that it generally may not be possible to modulate a particular cardiac region by stimulating or ablating a small number of particular autonomic nerve fibers. This is because stimulation of many different ganglia of the intrinsic cardiac nervous system may have a significant effect on any particular cardiac region. For example, vagal reflexes involving ganglia around the junction between the left atrium and pulmonary vein are thought to induce and perpetuate AF, but counterintuitively, ablation of nerves at that location increases rather decreases the inducibility of AF [HIROSE M, Leatmanoratn Z, Laurita K R, Carlson M D. Partial vagal denervation increases vulnerability to vagally induced atrial fibrillation. Cardiovasc Electrophysiol 13(12, 2002):1272-9]. This may be due to a problem inherent in the use of ablation, because it necessarily involves the destruction of sympathetic fibers, even when it is desired to ablate only parasympathetic fibers [Demosthenes G KATRITSIS. Autonomic Denervation for the Treatment of Atrial Fibrillation. Indian Pacing Electrophysiol J. 11(6, 2011): 161-166]. Furthermore, the ablation may increase inhomogeneity of refractoriness, which contributes to the inducibility of AF.

However, the failure of such localized ablation may also be attributable in part to the fact that many different ganglia of the heart may have a significant effect on that particular cardiac region. Thus, the majority of neurons in the mammalian heart display cholinergic properties, and branches of vagus nerves are distributed to all parts of both atria, such that stimulation of vagus branches innervating different portions of the intrinsic cardiac nervous system may also affect the portion of the heart nearest nerves that are ablated [LEGER J, Croll R P, Smith F M. Regional distribution and extrinsic innervation of intrinsic cardiac neurons in the guinea pig. Comp Neurol. 407(3, 1999):303-17]. Furthermore, even if ablation of a larger and more dispersed number of ganglia were to reduce the inducibility of AF, this would only be a temporary solution, because the nerves of the heart are capable of rapidly re-innervating the ablated regions [SAKAMOTO S, Schuessler R B, Lee A M, Aziz A, Lall S C, Damiano R J Jr. Vagal denervation and reinnervation after ablation of ganglionated plexi. J Thorac Cardiovasc Surg 139(2, 2010):444-52]. Thus, KAPA et al. write that "... while the intrinsic cardiac nervous system, partly mediated by signals received from the extrinsic cardiac nerves and partly by more local signals received from the heart, may play an integral role in the inducibility and propagation of AF, ways to use the data most appropriately are unclear" [KAPA S, Venkatachalam K L, Asirvatham S J. The autonomic nervous system in cardiac electrophysiology: an elegant interaction and emerging concepts. Cardiol Rev 18(6, 2010):275-84].

Low-level vagus nerve stimulation therefore offers a potentially better therapy for AF than ablation of cardiac ganglia, if it can simultaneously modulate the activities of many interacting ganglia of the intrinsic cardiac nervous system, in such a way that those ganglia collectively modify the electrophysiological properties of the particular regions of the heart in which actual or potential reentrant circuits or ectopic foci exist. In general, an objective of the low-level vagal nerve stimulation is to impede or reverse the electrophysiological changes in the atria that would cause high-level vagal nerve stimulation to induce AF. Such high-level vagal nerve stimulation is thought to shorten conduction velocity, action potential duration (APD), and atrial effective refractory period (ERP) non-uniformly, contributing to spatial ERP dispersion; and enhance ectopic focal firing from sites such as the pulmonary vein, superior vena cava, vein of Marshall, and atrial appendages. The high-level vagal nerve stimulation may also indirectly and reflexly stimulate the sympathetic nervous system to reduce atrial refractoriness and induce trigger activity in ectopic foci.

The present invention discloses methods for selecting parameters of the low-level vagus nerve stimulation in such a way as to achieve objectives listed in the previous paragraph. By low-level, we mean that the amplitude of the stimulus signal shown in FIG. 2 should ordinarily be set to a value less than or equal to a default value that would begin to decrease the heart rate for a patient in normal sinus rhythm. An amplitude higher than the default may also be used, but this is not preferred because it risks inducing or maintaining AF, as indicated in the previous paragraph. An amplitude lower than the default decreases such a risk, but it has the disadvantage that the vagus nerve stimulation may need to be performed in a session having a longer duration than would be the case with the default amplitude, in order to achieve a therapeutic result. However, an advantage of using a lower amplitude than the default may be that it could preferentially stimulate certain nerve fibers (e.g., B versus C fibers).

Parameters of the stimulation are selected to modulate electrophysiological properties of particular regions of the heart in AF, by influencing the amplitude and frequency of fibrillatory waves that may be extracted and measured in the AF patient's electrocardiogram. By selecting particular electrocardiographic leads for analysis, it is possible to preferentially extract electrophysiological characteristics of the corresponding portions of the atria. For example, ECG leads I, $V_5$ and aVL preferentially characterize left atrial activity; leads II, III and $aV_F$ preferentially characterize activity of the inferior atrial surface or coronary sinus; and leads $V_1$, $V_2$, and aVR preferentially characterize right atrial activity [RAVI K C, Krummen D E, Tran A J, Bulling a J R, Narayan S M. Electrocardiographic measurements of regional atrial fibrillation cycle length. Pacing Clin Electrophysiol 32(Suppl 1, 2009):566-71]. The fourier spectrum of the fibrillatory waves extracted from one such set of leads, say corresponding to the left atrium, may be characterized as having a dominant peak centered a particular frequency and having a measurable width. According to a preferred embodiment of the invention, the frequency of the vagus nerve stimulation is set to a multiple of that f-wave peak frequency. For example, if the f-wave frequency corresponding to the dominant left atrial peak is 6.7 cycles per second, the number of bursts per second of the vagal nerve stimulator may be set to approximately 6.7, 13.4, 20.1, or 26.8, etc., in an attempt to entrain the vagal stimulation with the f-wave. This procedure contrasts with previous methods of invasive vagal nerve stimulation, which stimulate at fixed, predetermined frequencies.

Having set the stimulation frequency, the number of sinusoidal impulses per burst (default 5) and the duration of an impulse (default 200 microseconds), may be varied about their default values in an attempt to modulate and preferably capture the dominant peak of the f-wave spectrum. Capturing of the peak will have occurred, for example, when the peak width narrows, and the frequency corresponding to the dominant peak can be decreased by deliberately decreasing the number of bursts per second of the vagus nerve stimulator. Such a decrease in frequency may have to be performed slowly over the course of many minutes, because it may correspond to the AF slowly losing reentrant wavelets one-by-one. At some point, the frequency may be small enough that the AF is unable to sustain itself, at which time the heart would revert to normal sinus rhythm. If the AF terminates, stimulation of the vagus nerve may be stopped, or it may be continued for a period of time to allow the atrium to be remodeled to become a more normal electrophysiological substrate. If continued stimulation is performed, the situation becomes what is described below in connection with the forecasting of the onset of AF. In that situation, there are no f-waves to monitor, but instead heart rate variability indices of parasympathetic and sympathetic tone are measured, along with indices concerning P-wave morphology, duration, and dispersion and indices related to the frequency of atrial premature beats. The stimulation may then be continued until such indices approach values that are considered to be acceptable.

If there are more than one significant peaks in the f-wave spectrum, the procedure may be as described above, with an attempt to capture the peak with the highest frequency followed by an attempt to capture the next-to-the-highest peak, etc. Alternatively, one may attempt to capture the more than one peak simultaneously, by stimulating the vagus nerve with superimposed waveforms like the ones shown in FIG. 2, wherein the superimposed waveforms have different parameter values, e.g., different frequencies corresponding to different peaks of the electrocardiogram's spectrum. The procedure may also be performed successively for spectra corresponding to different sets of ECG leads, in an attempt to capture or modulate the spectral peaks corresponding to successive regions of the atria.

In some embodiments of the invention, the amplitude of the stimulation may also be varied, so as to preferentially stimulate particular vagus nerve fibers, although the maximum allowed amplitude would generally be constrained not to decrease the heart rate of an individual in normal sinus rhythm. For example, this may involve carefully graded increases in stimulus amplitude to activate the largest diameter fibers in the vagus nerve, followed by gradual recruitment of smaller fibers as the amplitude is increased.

In other embodiments of the invention, parameters of the stimulation may be modulated in synchrony with events that are known to influence or be influenced by the autonomic nervous system. Examples of such events involve respiration (e.g., end-of-inspiration, end-of-expiration) or ventricular contraction (e.g., with resetting of the stimulation at a fixed time after each QRS complex of the electrocardiogram).

As shown in FIG. 8, the autonomic nervous system also influences the heart through circulating catecholamines. The electrical field delivered to the vagus nerve by the device(s) of the prevent invention may stimulate the release of hormones into the circulation at concentrations that affect the onset and/or termination of AF, but that have little effect on heart rate or blood pressure. In one embodiment of the present invention, the release of catecholamines is accomplished by generating a parasympathetic, afferent vagal signal to the brain, which then triggers an efferent sympathetic signal to stimulate the release of catecholamines from the adrenal glands. In animal studies demonstrating the effects of vagal stimulation, data have indicated that applicant's device(s) can stimulate such release, even if the vagus nerve is tied off distal to the electrode, and that the effects can be blocked with the β-blocker propranolol. In addition, such stimulation is ineffective in animals that have had their adrenal glands removed (an endogenous source of these catecholamines) [SIMON B J, Emala C W, Lewis L M, Theodoro D, Purim-Shem-Tov Y, Sepulveda P, Hoffmann T J, Staats P. Vagal Nerve Stimulation for Relief of Bronchoconstriction: Preliminary Clinical Data and Mechanism of Action. NANS 13th Meeting, Las Vegas, December, 2009; HOFFMANN T J, Mendez S, Staats, P, Emala C, Guo P. Inhibition of Histamine-Induced Bronchoconstriction in Guinea Pig and Swine by Pulsed Electrical Vagus Nerve Stimulation. Neuromodulation. 2009; 12: 261-269].

Although the methods described above may be performed manually by the operator of the vagus nerve stimulator, they also lend themselves to automatic control. If it is desired to temporarily or permanently maintain a constant stimulation in the vicinity of the vagus nerve, for example, to perform stimulation with the amplitude maintained at the default level as described above, methods of control theory may be employed to modulate the power of the stimulator in order to compensate for patient motion or other mechanisms that would otherwise give rise to variability in the power of stimulation. In the case of stimulation of the vagus nerve, such variability may be attributable in part to the patient's breathing, which may involve contraction and associated change in geometry of the sternocleidomastoid muscle that is situated close to the vagus nerve (identified as 65 in FIG. 7).

Figure 9:
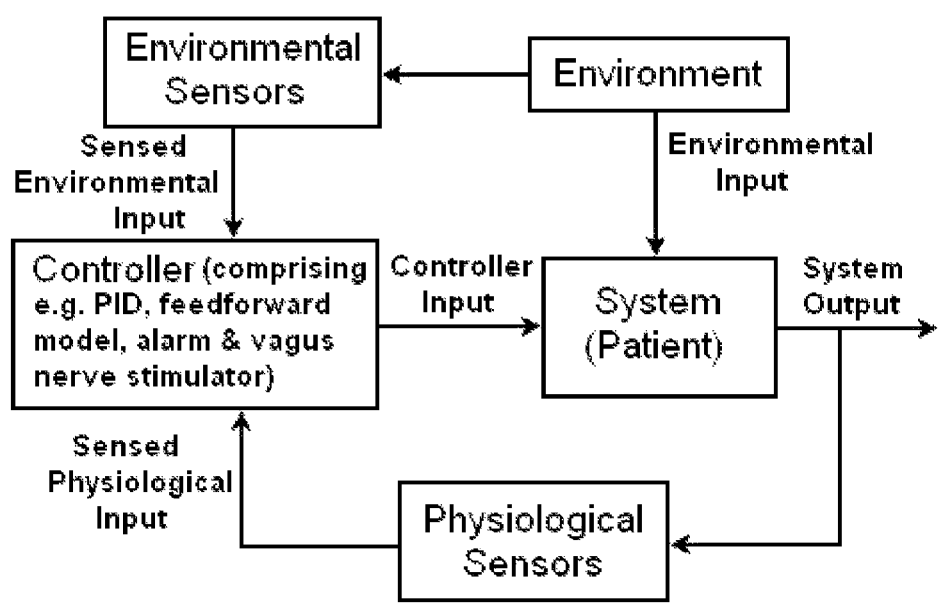
FIG. 9 illustrates connections between the controller and controlled system according to the present invention, their input and output signals, and external signals from the environment.

FIG. 9 is a control theory representation of the disclosed vagus nerve stimulation methods, used not only to maintain constant stimulation amplitude if desired, but also used in connection with the setting of other stimulation parameters, as described below. As shown in FIG. 9, the patient, or the relevant physiological component of the patient (e.g., the heart and its innervation), is considered to be the "System" that is to be controlled. The "System" (patient) receives input from the "Environment." For example, in the case of an individual at risk for developing atrial fibrillation, the environment would include fine particulate air pollution that may trigger AF [Liao D, Shaffer M L, He F, Rodriguez-Colon S, Wu R, Whitsel E A, Bixler E O, Cascio W E. Fine particulate air pollution is associated with higher vulnerability to atrial fibrillation—the APACR study. J Toxicol Environ Health A. 74(11, 2011):693-705]. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. For example, for an individual who is at risk for the development of AF, the alcohol contained within an individual's stomach might be considered to be a relevant portion of the environment, because alcohol consumption is a well-known trigger of AF [Mukamal K J, Tolstrup J S, Friberg J, Jensen G, Grønbaek M. Alcohol consumption and risk of atrial fibrillation in men and women: the Copenhagen City Heart Study. Circulation 112(12, 2005):1736-42]. On the other hand, if it is intended to control the former component to influence the latter component, then both components should be considered part of the "System."

The System also receives input from the "Controller", which in this case may comprise the vagus nerve stimulation device, as well as electronic components that may be used to select or set parameters for the stimulation protocol (amplitude, frequency, pulse width, burst number, etc.) or alert the patient as to the need to use the stimulator (i.e., an alarm). For example, the controller may include the control unit 330 in FIG. 1. Feedback in the schema shown in FIG. 9 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller.

The preferred sensors will be ones ordinarily used for ambulatory monitoring, selected to characterize the heart and the modulation of its function by the autonomic nervous system. For example, the sensors may comprise those used in conventional Holter and bedside monitoring applications, for monitoring heart rate, ECG, respiration, core temperature, hydration, blood pressure, brain function, oxygenation, and skin temperature. The sensors may be embedded in garments or placed in sports wristwatches, as currently used in programs that monitor the physiological status of soldiers [G. A. Shaw, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. The ECG sensors should be adapted to the automatic extraction and analysis of particular features of the ECG, for example, the fibrillatory waves that were described above in connection with the characterization of AF, and for patients in normal sinus rhythm, indices of P-wave morphology, as well as indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. Although AF can be detected from the ECG alone, an event marker may also be included in order for the patient to mark relevant circumstances and sensations.

Let the measured output variables of the system be denoted by $y_i$ (i=1 to Q); let the desired (reference or setpoint) values of $y_i$ be denoted by $r_i$ and let the controller's input to the system consist of variables $u_j$ (j=1 to P). The objective is for a controller to select the input $u_j$ in such a way that the output variables (or a subset of them) closely follows the reference signals $r_i$, i.e., the control error $e_i=r_i-y_i$ is small, even if there is environmental input or noise to the system. Consider the error function $e_i=r_i-y_i$ to be the sensed physiological input to the controller in FIG. 9 (i.e., the reference signals are integral to the controller, which subtracts the measured system values from them to construct the control error signal). The controller will also receive a set of measured environmental signals $v_k$ (k=1 to R), which also act upon the system as shown in FIG. 9.

The functional form of the system's input u(t) is constrained to be as shown in FIG. 2. Ordinarily, a parameter that needs adjusting is the one associated with the amplitude of the signal shown in FIG. 2. As a first example of the use of feedback to control the system, consider the problem of adjusting the input u(t) from the vagus nerve stimulator (i.e., output from the controller) in order to compensate for motion artifacts.

Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999):335-346]. Such motion artifact can be due to movement by the patient (e.g., neck movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) nerve stimulation amplitude that needs continuous adjustment.

Accelerometers can be used to detect all these types of movement, using for example, Model LSM330DL from STMicroelectronics, 750 Canyon Dr #300 Coppell, Tex. 75019. One or more accelerometer is attached to the patient's neck, and one or more accelerometer is attached to the head of the stimulator in the vicinity of where the stimulator contacts the patient. Because the temporally integrated outputs of the accelerometers provide a measurement of the current position of each accelerometer, the combined accelerometer outputs make it possible to measure any movement of the stimulator relative to the underlying tissue.

The location of the vagus nerve underlying the stimulator may be determined preliminarily by placing an ultrasound probe at the location where the center of the stimulator will be placed [Knappertz V A, Tegeler C H, Hardin S J, McKinney W M. Vagus nerve imaging with ultrasound: anatomic and in vivo validation. Otolaryngol Head Neck Surg 118(1, 1998): 82-5]. The ultrasound probe is configured to have the same shape as the stimulator, including the attachment of one or more accelerometer. As part of the preliminary protocol, the patient with accelerometers attached is then instructed to perform neck movements, breathe deeply so as to contract the sternocleidomastoid muscle, and generally simulate possible motion that may accompany up to several hours of stimulation with the stimulator. This would include possible slippage or movement of the stimulator relative to an initial position on the patient's neck. While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve position data as a function of accelerometer position data.

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion Moore. Electrical Stimulation for pain suppression: mathematical and physical models. Thesis, School of Engineering, Cornell University, 2007; Bartosz SAWICKI, Robert Szmurto, Przemystaw Ptonecki, Jacek Starzynski, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

As another example of automatic control, we disclose adjustment of the parameters of the vagus nerve stimulation in such a way as to control the frequency of the dominant peak(s) in the Fourier spectrum of the f-waves that are found in the electrocardiogram of atrial fibrillation patients. The methods described above considered the dominant peak to be stationary, but in actuality, the peak(s) may fluctuate in regards to their central frequency and width. Therefore, the present invention contemplates the use of feedback and feedforward methods of control theory to adapt the stimulation parameters to changing characteristics of the patient's atrial electrocardiogram. Such control theory methods have been used in other neuromodulation applications, but have been not been described in connection with the measurement and control of f-waves. For example, U.S. Pat. No. 7,403,820, entitled Closed-loop feedback-driven neuromodulation, to DiLorenzo, discloses the use of feedback to construct neuromodulation parameters, but only for the treatment of neurological disorders. U.S. Pat. Nos. 5,690,681 and 5,916,239, both entitled Method and apparatus using vagal stimulation for control of ventricular rate during atrial fibrillation, to Geddes et al., describe closed-loop, variable-frequency, vagal-stimulation apparatus for control of ventricular rate during atrial fibrillation. TOSATO et al and ZHOU et al also describe closed-loop systems for control of the heart rate by stimulating a vagus nerve [TOSATO M, Yoshida K, Toft E, Nekrasas V, Struijk J J. Closed-loop control of the heart rate by electrical stimulation of the vagus nerve. Med Biol Eng Comput 44(3, 2006):161-9; Yuxuan ZHOU, Yuan Yuan, Juan Gao, Ling Yang, Feng Zhang, Guoqing Zhu, Xingya Gao. An Implanted Closed-loop Chip System for Heart Rate Control: System Design and Effects in Conscious Rats. Journal of Biomedical Research 24(2, 2010: 107-114]. However, they all differ from the closed-loop, variable frequency stimulation of the present invention in that the present invention monitors and controls atrial contractions (f-waves), not ventricular contraction. Furthermore, those investigators disclose implantable, not noninvasive devices.

For present purposes, no distinction is made between a system output variable and a variable representing the state of the system. Then, a state-space representation, or model, of the system consists of a set of first order differential equations of the form d $y_i$/dt=$F_i$(t,{$y_i$},{$u_j$},{$v_k$};{$r_i$}), where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form:

$$u(t) = K_p e(t) + K_i \int_0^t e(\tau) d\tau + K_d \frac{de}{dt}$$

where the parameters for the controller are the proportional gain ($K_p$), the integral gain ($K_i$) and the derivative gain ($K_d$). This type of controller, which forms a controlling input signal with feedback using the error e=r−y, is known as a PID controller (proportional-integral-derivative).

Although classical control theory works well for linear systems having one or only a few system variables, special methods have also been developed for systems in which the system is nonlinear (i.e., the state-space representation contains nonlinear differential equations), or multiple input/output variables. Such methods are important for the present invention because the physiological system to be controlled will be generally nonlinear, and there will generally be multiple output physiological signals. It is understood that those methods may also be implemented in the controller shown in FIG. 9 [Torkel GLAD and Lennart Ljung. Control Theory. Multivariable and Nonlinear Methods. New York: Taylor and Francis, 2000; Zdzislaw BUBNICKI. Modern Control Theory. Berlin: Springer, 2005].

Optimal selection of the parameters of a PID controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be made according to rules that were described initially by Ziegler and Nichols. There are also many improved versions of tuning rules, including some that can be implemented automatically by the controller [LI, Y., Ang, K. H. and Chong, G. C. Y. Patents, software and hardware for PID control: an overview and analysis of the current art. IEEE Control Systems Magazine, 26 (1, 2006): 42-54; Karl Johan Åström & Richard M. Murray. Feedback Systems: An Introduction for Scientists and Engineers. Princeton N.J.: Princeton University Press, 2008; Finn HAUGEN. Tuning of PID controllers (Chapter 10) In: Basic Dynamics and Control. 2009. ISBN 978-82-91748-13-9. TechTeach, Enggravhøgda 45, N-3711 Skien, Norway. http://techteach.no., pp. 129-155; Dingyu XUE, YangQuan Chen, Derek P. Atherton. PID controller design (Chapter 6), In: Linear Feedback Control: Analysis and Design with MATLAB. Society for Industrial and Applied Mathematics (SIAM). 3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998]. Commercial versions of PID controllers are available, and they are used in 90% of all control applications. In the present invention, PID control is generally not needed to adjust the stimulator's number of bursts per second, because the controller can simply measure the changing dominant frequency in the atrial electrocardiogram and immediately change the bursts per second of the stimulator accordingly. However, control of the width of the dominant peak in the atrial electrocardiogram would benefit from the use of a PID controller, wherein it is desired to maintain or decrease the width in an attempt to capture the dominant peak, the measured width being the y in the error e=r−y, and r being the desired width. In that case, the number of pulses per burst and/or the duration of a pulse, may be varied by the tuned PID controller in an attempt to minimize the error.

Performance of system control can be improved by combining the feedback closed-loop control of a PID controller with feed-forward control, wherein knowledge about the system's future behavior can be fed forward and combined with the output of the PID (or other type of feedback controller) to improve the overall system performance. For example, if the sensed environmental input in FIG. 9 is such the environmental input to the system will have a deleterious effect on the system after a delay, the controller may use this information to provide anticipatory control input to the system, so as to avert or mitigate the deleterious effects that would have been sensed only after-the-fact with a feedback-only controller. Thus, the controller shown in FIG. 9 will generally make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. It is a type of predictive controller, methods for which have been developed in many contexts, such as when a model of the system is used to calculate future outputs of the system, with the objective of choosing among possible inputs so as to optimize a criterion that is based on future values of the system's output variables.

The present invention is concerned with two types of forecasting (feed-forward) problems: (1) The patient is in AF and is being stimulated with the stimulator, and prediction of the termination of AF is made and/or prediction of the time-course of the f-wave is predicted; and (2) The patient is normal sinus rhythm, and prediction of imminent AF is made in order to avert its onset. The latter embodiment of the present invention comprises the following steps. Components of the device that are used to make the forecast of imminent AF are worn by the patient. Note that the forecasting task does not in general necessitate wearing the vagal nerve stimulator for a patient in normal sinus rhythm. The forecasting components of the device then predict the imminent onset of atrial fibrillation (using data obtained from an electrocardiogram plus accessory noninvasive data, e.g., respiration and motion), for example, as described in publications such as the ones cited below. When the device sounds the alarm, the patient or a caregiver then performs noninvasive vagal nerve stimulation to avert the AF. The prophylactic stimulation protocol comprises low-level right-side or both-side vagal stimulation. If the patient has been previously treated with the stimulator while in AF, parameters of the prophylactic stimulation may be set to their previously effective values. Otherwise, the stimulation parameters may be set to values that are motivated by measurements of characteristics of the patient's heart-rate variability or P-waves, as described below in connection with the forecasting of imminent AF.

A mathematical model of the system is needed in order to perform the predictions of system behavior. Models that are completely based upon physical first principles (white-box) are rare, especially in the case of physiological systems. Instead, most models that make use of prior structural and mechanistic understanding of the system are so-called grey-box models. Such grey-box models of atrial fibrillation exist [Elizabeth M. CHERRY, Fagen Xie, Zenaida Feliciano, Alan Garfinkel. Computer modeling of atrial fibrillation. Cardiac Electrophysiology Review 5 (2001):271-276; JACQUEMET, V., Kappenberger, L., Henriquez, C. S. Modeling atrial arrhythmias: Impact on clinical diagnosis and therapies. IEEE Reviews in Biomedical Engineering 1 (2008):94-114; HAISSAGUERRE M, Lim K T, Jacquemet V, Rotter M, Dang L, Hocini M, Matsuo S, Knecht S, Jaïs P, Virag N. Atrial fibrillatory cycle length: computer simulation and potential clinical importance. Europace 9 (Suppl 6, 2007):vi64-70]. However, currently available grey-box models need to be extended in order to accommodate predictions concerning the effects on AF by the vagus nerve stimulation of the present invention, as now described.

The grey-box models most closely related to present objectives are those described by VIGMOND et al. and by VALASCO. VIGMOND et al. constructed mathematical models of the effects of vagally induced heterogeneity of action potential duration on reentry initiated by an ectopic beat, in which the atrium was modeled in a morphologically realistic manner. For small vagal stimulation (acetylcholine release), the reentry was as a figure-of-8. For larger amplitude stimulation, rotor behavior was observed. For large amplitude vagus stimulation, reentry stabilized in the left atrium around the pulmonary veins; in the right atrium, it anchored to the caval veins. VIGMOND et al. noted, however, that their initial assumptions were ad hoc, because vagal mapping over the whole organ is not available [VIGMOND EJ, Tsoi V, Kuo S, Arevalo H, Kneller J, Nattel S, Trayanova N. The effect of vagally induced dispersion of action potential duration on atrial arrhythmogenesis. Heart Rhythm 1(3, 2004):334-44]. This work was expanded by VALASCO, but he too did not consider the effects of low-level vagus nerve stimulation in atria already experiencing AF [Mauricio Munoz VALASCO. Onset of atrial arrhythmias by autonomic neural stimulation and their termination—a simulation study. 2009 Thesis. University of Calgary. Calgary, Alberta]. These models were derived from one described by KNELLER et al, which in turn was derived from earlier ones that were inspired by one described by COURTEMANCHE et al [KNELLER J, Zou R, Vigmond E J, Wang Z, Leon U, Nattel S. Cholinergic atrial fibrillation in a computer model of a two-dimensional sheet of canine atrial cells with realistic ionic properties. Circ Res 90(9, 2002):E73-87; COURTEMANCHE M, Ramirez R J, Nattel S. Ionic mechanisms underlying human atrial action potential properties: insights from a mathematical model. Am J Physiol 275(1, Pt 2, 1998):H301-21].

The above-cited grey-box models describe the electrophysiology of only the atrium itself, so that additional calculation must be performed in order to obtain the corresponding surface atrial electrocardiogram, which is what is actually extracted from noninvasive ECG measurement. The atrial electrocardiogram may be construction from the above-cited grey-box models using known methods [JACQUEMET V, van Oosterom A, Vesin J M, Kappenberger L. Analysis of electrocardiograms during atrial fibrillation. A biophysical model approach. IEEE Eng Med Biol Mag 25(6, 2006):79-88].

For the present invention, the above-cited models may be used, or they may be adapted to make use of other computational platforms [Oleg V ASLANIDI, Michael A Colman, Jonathan Stott, Halina Dobrzynski, Mark R Boyett, Arun V Holden and Henggui Zhang. 3D virtual human atria: A computational platform for studying clinical atrial fibrillation. Prog Biophys Mol Biol 107(1, 2011): 156-168]. However, a major deficiency of those models is that they do not include a suitable representation of the spatial distribution within the atria of acetylcholine activity, which depends not only on the spatial distribution of projections of the vagus nerve to the atria, but also how the intrinsic cardiac autonomic nervous system will modulate that acetylcholine activity as a function of vagus nerve stimulation parameters (amplitude, burst frequency, sinusoidal pulses per burst, pulse width). Thus, let the symbol j index ganglionated plexi in the atria (or individual ganglia in an enlarged model), and let $A_j$ (j=1 to 5 if only the ganglionated plexi are modeled) denote the acetylcholine activity of the jth plexus. The variables $A_j$ may be inserted into the model of VIGMOND et al at their corresponding anatomical locations, but it remains to model how the $A_j$ of the different ganglionated plexi interact with one another. To that end, construct a general purpose representation such as $$\frac{dAj}{dt} = a_j + \sum_{k=1}^{S} b_{jk} A_k + \sum_{k=1}^{S}\sum_{l=1}^{S} c_{jkl} A_k A_l + \dots ,$$

where $a_j$, $b_{jk}$, and $c_{jkl}$ are model parameters that are functions of the vagus stimulation parameters. Thus, the present invention adds these parameters to the ones in the model of VIGMOND et al and to the parameters needed to extrapolate results of simulation of atrial electrophysiology to obtain the corresponding surface electrocardiogram. The parameters may also be made to be a function of the phase of respiration, or any other physiological variable that is measured in order to characterize the status of the autonomic nervous system.

Many of the values of the model's parameters may then be set to ones that were assigned by VIGMOND et al, but the others have to be estimated from data. Thus, for a given set of vagus stimulation parameter values, the electrocardiogram of a patient is measured, and the model's parameters are estimated from the electrocardiogram data using existing methods such as the multiple shooting and recursive (e.g., Kalman filter) approaches [Henning U. VOSS and Jens Timmer. Nonlinear dynamical system identification from uncertain and indirect measurements. International Journal of Bifurcation and Chaos 14(6, 2004):1905-1933], or synchronization methods [HDI ABARBANEL, DR Creveling, and J M Jeanne. Estimation of parameters in nonlinear systems using balanced synchronization. Physical Review E 77 (2008):016208, pp 1-14].

The process of estimating the model's parameters then has to be repeated for many other sets of stimulation parameters, so as to complete the identification of the system. Once the model's parameters have been so estimated, the electrophysiological state of the atria may be forecast from the model by calculation, and the electrocardiogram corresponding to that forecasted state would also be calculated. In fact, the forecast may be made with many different sets of potential stimulation parameter values, in an attempt to find the set of parameter values that would terminate the AF, or at least reduce the fibrillatory frequency. Thus, by using such feedforward methods, the controller shown in FIG. 9 may achieve therapeutic results superior to the use of feedback alone. Note that such a model would also be useful for diagnostic purposes, because after fitting the model's parameters, calculating the state of the atrium as a function of time will reveal the number and location of reentrant wavelets and ectopic foci, which is not currently possible using available diagnostic tools.

If the physiological mechanisms are not sufficiently validated to use a grey-box model, a black-box or ad hoc forecasting model may be used instead. Ad hoc methods include those cited above in connection with the clinical decision regarding whether AF will self-terminate, except that for the present invention, the methods would be applied to training sets of electrocardiograms that had been collected while vagus nerve stimulation was in progress. Black-box models also comprise autoregressive models [Tim BOLLERSLEV. Generalized autoregressive condiditional heteroskedasticity. Journal of Econometrics 31 (1986):307-327], or those that make use of principal components [James H. STOCK, Mark W. Watson. Forecasting with Many Predictors, In: Handbook of Economic Forecasting. Volume 1, G. Elliott, C. W. J. Granger and A. Timmermann, eds (2006) Amsterdam: Elsevier B. V, pp 515-554], Kalman filters [Eric A. WAN and Rudolph van der Merwe. The unscented Kalman filter for nonlinear estimation, In: Proceedings of Symposium 2000 on Adaptive Systems for Signal Processing, Communication and Control (AS-SPCC), IEEE, Lake Louise, Alberta, Canada, October, 2000, pp 153-158], wavelet transforms [O. RENAUD, J.-L. Stark, F. Murtagh. Wavelet-based forecasting of short and long memory time series. Signal Processing 48 (1996):51-65], hidden Markov models [Sam ROWEIS and Zoubin Ghahramani. A Unifying Review of Linear Gaussian Models. Neural Computation 11(2, 1999): 305-345], or artificial neural networks [Guoquiang ZHANG, B. Eddy Patuwo, Michael Y. Hu. Forecasting with artificial neural networks: the state of the art. International Journal of Forecasting 14 (1998): 35-62].

For the present invention, a grey-box model is preferred, but if a black-box model must be used instead, the preferred model will be one that makes use of support vector machines. A support vector machine (SVM) is an algorithmic approach to the problem of classification within the larger context of supervised learning. In the present context, a training set of physiological data will have been acquired that includes whether or not the patient is experiencing AF. Thus, the classification of the patient's state is whether or not the AF is in progress, and the data used to make the classification consist of the remaining acquired physiological data (ECG, along with simultaneous data from other sensors such as for respiration and accelerometry for motion artifact), as well as parameters of the stimulator device (if it is currently being used on a patient in AF), evaluated at $\Delta$ time units prior to the time at which the binary AF (yes/no) data are acquired. Thus, for a patient who is in AF, the SVM is trained to forecast the termination of AF, $\Delta$ time units into the future, and the training set includes the time-course of features extracted from the ECG, including the atrial fibrillatory waveform and features extracted from it, such as the dominant peak frequency and its width, as described above. For a patient who is not in AF, the SVM is trained to forecast the imminence of AF, $\Delta$ time units into the future, and the training set includes the time-course of features extracted from the ECG, including heart rate variability indices of autonomic balance, P-wave duration and morphology, and the frequency of atrial premature beats, as described below. After training the SVM, it is implemented as part of the controller. For patients in normal sinus rhythm, the controller may sound an alarm and advise the use of vagal nerve stimulation, whenever there is a forecast of imminent AF [Christopher J. C. BURGES. A tutorial on support vector machines for pattern recognition. Data Mining and Knowledge Discovery 2 (1998), 121-167; J. A. K. Suykens, J. Vandewalle, B. De Moor. Optimal Control by Least Squares Support Vector Machines. Neural Networks 14 (2001):23-35; Sapankevych, N. and Sankar, R. Time Series Prediction Using Support Vector Machines: A Survey. IEEE Computational Intelligence Magazine 4(2, 2009): 24-38; Press, W H; Teukolsky, S A; Vetterling, W T; Flannery, BP (2007). Section 16.5. Support Vector Machines. In: Numerical Recipes: The Art of Scientific Computing (3rd ed.). New York: Cambridge University Press].

Several methods have been proposed to predict the imminent onset of atrial fibrillation in a patient who is currently in sinus rhythm [G B MOODY, A L Goldberger, S McClennen, S P Swiryn. Predicting the onset of paroxysmal atrial fibrillation: the Computers in Cardiology Challenge 2001. Computers in Cardiology 28 (2001):113-116]. Note that predictions according to the present invention may be better than previous ones, because they may be based on the analysis of many simultaneous physiological signals. At a minimum, the prediction is made from an analysis of an electrocardiogram of the patient over an extended period of time, which requires the patient to have attached monitoring devices or wear them in sports watches or special clothing, even though the patient is not necessarily wearing the vagal nerve stimulator. Measurement of respiration using noninvasive inductive plethysmography, mercury in silastic strain gauges or impedance pneumography is also advised, in order to account for the effects of respiration on the heart rate. A noninvasive accelerometer may also be included among the ambulatory sensors in order to account for motion artifacts, and although AF can be detected from the ECG alone, an event marker may also be included in order for the patient to mark relevant circumstances and sensations.

Many onset-of-AF prediction methods involve an analysis of heart rate variability, particularly the high frequency component of heart rate variability as an indicator of vagal tone [VIKMAN S, Mäkikallio TH, Yli-Mäyry S, Pikkujämsä S, Koivisto A M, Reinikainen P, Airaksinen K E, Huikuri H V. Altered complexity and correlation properties of R-R interval dynamics before the spontaneous onset of paroxysmal atrial fibrillation. Circulation 100(20, 1999):2079-84; FIORANELLI M, Piccoli M, Mileto G M, Sgreccia F, Azzolini P, Risa M P, Francardelli R L, Venturini E, Puglisi A. Analysis of heart rate variability five minutes before the onset of paroxysmal atrial fibrillation. Pacing Clin Electrophysiol 22(5, 1999):743-9; BETTONI M, Zimmermann M. Autonomic tone variations before the onset of paroxysmal atrial fibrillation. Circulation 105(23, 2002):2753-9; VIKMAN S, Lindgren K, Mäkikallio T H, Yli-Mäyry S, Airaksinen K E, Huikuri H V. Heart rate turbulence after atrial premature beats before spontaneous onset of atrial fibrillation. J Am Coll Cardiol. 45(2, 2005):278-84; SUGIURA H, Chinushi M, Komura S, Hirono T, Aizawa Y. Heart rate variability is a useful parameter for evaluation of anticholinergic effect associated with inducibility of atrial fibrillation. Pacing Clin Electrophysiol 28(11, 2005):1208-14]. U.S. Pat. No. 5,749,900, entitled Implantable medical device responsive to heart rate variability analysis, to Schroeppel et al, describe invasive methods for forecasting and responding to cardiac events, but does not mention atrial fibrillation. Some onset-of-AF prediction methods evaluate rates of atrial and ventricular depolarization [Patent application US20040148109, entitled Method and apparatus for prediction of cardiac dysfunction, to Fischer], and others take into account the effects of circadian rhythm on the onset of AF [Patent application US20100145208, entitled Device For Predicting Tachyarrhythmias And/Or Atrial Arrhythmias, to Schirdewan].

Before the onset of atrial fibrillation, the frequency of atrial premature beats also increases, and the dispersion and morphology of the corresponding P-waves change [HAYN D, Kollmann A, Schreier G. Predicting initiation and termination of atrial fibrillation from the ECG. Biomed Tech 52(1, 2007):5-10; VINCENTI A, Brambilla R, Fumagalli M G, Merola R, Pedretti S. Onset mechanism of paroxysmal atrial fibrillation detected by ambulatory Holter monitoring. Europace 8(3, 2006):204-10; MAGNANI J W, Williamson M A, Ellinor P T, Monahan K M, Benjamin E J. P wave indices: current status and future directions in epidemiology, clinical, and research applications. Circ Arrhythm Electrophysiol 2(1, 2009):72-9]. In regards validation of P-wave analysis algorithms, it is understood that P-wave changes can be measured with the aid of ultrasound more accurately than from the ECG alone [MERCKX K L, De Vos C B, Palmans A, Habets J, Cheriex E C, Crijns H J, Tieleman R G. Atrial activation time determined by transthoracic Doppler tissue imaging can be used as an estimate of the total duration of atrial electrical activation. J Am Soc Echocardiogr. 18(9, 2005):940-4; DEVOS C B, Weijs B, Crijns H J, Cheriex E C, Palmans A, Habets J, Prins M H, Pisters R, Nieuwlaat R, Tieleman R G. Atrial tissue Doppler imaging for prediction of new-onset atrial fibrillation. Heart 95(10, 2009):835-40].

If the patient in normal sinus rhythm has been previously treated with the stimulator while in AF, parameters of the prophylactic stimulation may be set to their previously effective values. Otherwise, the stimulation parameters may be set to values that are motivated by measurements of characteristics of the patient's heart-rate variability, P-waves, or atrial premature beat frequency. According to the above-cited methods, the forecast of imminent AF may be triggered because sympathetic versus parasympathetic tone is unbalanced, as evidenced by analysis of heart rate variability, which involves the measurement of low versus high frequency components of the fourier transform of heart rate, as determined from measured R-R intervals [e.g., BETTONI M, Zimmermann M. Autonomic tone variations before the onset of paroxysmal atrial fibrillation. Circulation 105(23, 2002): 2753-9]. The forecast of imminent AF may also be triggered because the frequency of atrial premature beats also increases, and/or the dispersion and morphology of the corresponding P-waves change [e.g., HAYN D, Kollmann A, Schreier G. Predicting initiation and termination of atrial fibrillation from the ECG. Biomed Tech 52(1, 2007):5-10]. Normal (setpoint) values for indices concerning the balance of sympathetic and parasympathetic tone, atrial premature beat frequency, and P-wave morphology and duration may be assumed from values found in the literature, or they may be measured for each patient while the patient is in normal sinus rhythm. The controller with vagus nerve stimulator attached may be tuned by preliminarily stimulating the patient to determine the effect that the stimulation has on the values of those indices, for given sets of stimulator parameter values. Such indices will normally fluctuate, so after tuning, the stimulator may then be used to continuously and automatically stimulate the patient to minimize the error between the fluctuating index values and their setpoints. The invention contemplates that such feedback control could involve variation in any of the stimulator's parameters, including the amplitude of the stimulation signal, although the maximum allowed amplitude would generally be constrained not to decrease the heart rate of an individual in normal sinus rhythm.

However, in the preferred embodiment of the invention for averting AF, the nerve stimulator would not be used continuously to maintain the fluctuating index values to within a range about the setpoints. Instead, in preferred embodiments, the patient would not continuously wear the vagus nerve stimulator. The patient would instead use vagus nerve stimulator only when imminent AF was forecasted during continuous monitoring of the patient's physiological signals by the controller. After the controller sounds the alarm, the patient or a caregiver would then apply the vagus nerve stimulator to the patient's neck, using stimulation parameters that had already been selected by tuning the controller, as described above. The stimulation would then be maintained until the controller no longer forecasts imminent AF, or until the physiological indices were within acceptable limits, or until a predetermined session-duration has elapsed.

A different strategy for selecting the stimulator's parameters may also be used, in which several alternate sets of stimulator values are available for use. This strategy would be used when properties of the patient's normal P-wave, heart rate variability, and atrial premature beat frequency indices are not stationary. For example, the normal index values may at one time have certain normal semi-stationary characteristics, but at a later time, they may have different semi-stationary characteristics, for example because of circadian rhythms. In each epoch, the controller may be tuned in accordance with the normal P-wave morphology, heart rate variability, and atrial premature beat frequency indices that characterize that epoch. Default stimulation parameter values may be different, depending on which semi-stationary epoch obtained at the time of controller tuning. Accordingly, when the stimulator is eventually used for prophylactic treatment of a patient, the stimulator should be set to parameter values that are selected to correspond to the semi-stationary epoch that obtains immediately before stimulation is used for the prophylactic therapy.

The vagus nerve is not the only nerve or tissue that may be stimulated as a countermeasure against sympathetic/parasympathetic imbalance that may contribute to the onset or persistence of atrial fibrillation (see FIG. 8). Commonly assigned co-pending patent applications US20070106338, entitled Direct and Indirect Control of Muscle for the Treatment of Pathologies, to ERRICO, and US20100249873, entitled Direct and Indirect Control of Muscle for the Treatment of Pathologies, to ERRICO, contemplate the electrical stimulation of nerves emanating from a patient's sympathetic nerve chain, as well as stimulation of the nerve plexus of fibers emanating from both the sympathetic nerve chain and the vagus nerve, such as the hepatic plexus. U.S. Pat. No. 7,418,292 to SHAFER also relates to electrical stimulation of neurons of the sympathetic nervous system. U.S. Pat. No. 7,877,146, entitled Methods of treating medical conditions by neuromodulation of the sympathetic nervous system, to REZAI et al is concerned with the neuromodulation of the sympathetic nervous system to treat a long list of diseases. The stimulation of a branch of the greater splanchnic nerve also causes release of catecholamines from the adrenal gland, in addition to direct electrical stimulation of that gland [Xi GUO and Arun R. Wakade. Differential secretion of catecholamines in response to peptidergic and cholinergic transmitters in rat adrenals. Journal of Physiology 475(3, 1994): 539-545]. Therefore, devices and methods of the present invention might be applied to other nerves and tissues to treat or avert atrial fibrillation, particularly if stimulation of such a non-vagus nerve lies reasonably close to the surface of the skin, for example, as evidenced by the fact that it had previously been stimulated by percutaneous methods.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating atrial fibrillation in a patient, comprising:
    positioning a device in contact with an outer skin surface of a neck of the patient;
    generating an electric current within the device, wherein the electric current comprises bursts of pulses with each burst having a frequency of about 15 to about 50 Hz and each pulse having a pulse duration of about 50 to about 1000 microseconds; and
    transmitting the electric current through an electrically conductive fluid within the device transcutaneously through the neck of the patient to a vagus nerve in the patient, wherein the electric current is sufficient to terminate an episode of atrial fibrillation.

2. The method of claim 1 wherein the generating step is carried out with a pulse generator coupled to one or more electrodes.

3. The method of claim 1 further comprising generating an electrical field at or near the device and shaping the electrical field such that the electrical field is sufficient to modulate the vagus nerve; and wherein the electrical field is not sufficient to substantially modulate a nerve or muscle between the outer skin surface and the vagus nerve.

4. The method of claim 1 wherein the electric current is transmitted to the right vagus nerve of the patient.

5. The method of claim 1 wherein each burst of pulses contains from 2 to 20 pulses.

6. The method of claim 1 wherein the pulses are full sinusoidal waves.

* * * * *